US011369801B2

(12) United States Patent
Malekkhosravi et al.

(10) Patent No.: US 11,369,801 B2
(45) Date of Patent: Jun. 28, 2022

(54) ASSEMBLIES AND HEADGEAR THEREOF FOR RECHARGING IMPLANTABLE MEDICAL ELECTRICAL SYSTEMS

(71) Applicant: Medtronic, Inc., Minneapolis, MN (US)

(72) Inventors: Shahram Malekkhosravi, Maple Grove, MN (US); Venkat R. Gaddam, Plymouth, MN (US); Rebecca J. S. Haag, Fridley, MN (US); Eric R. Schleppenbach, St. Louis Park, MN (US); Brendan J. Young-Dixon, St. Paul, MN (US); Marshall S. Comisar, Minneapolis, MN (US); Zane K. Thimmesch-Gill, Minneapolis, MN (US); Brent P. Johnson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 662 days.

(21) Appl. No.: 15/946,370

(22) Filed: Apr. 5, 2018

(65) Prior Publication Data
US 2018/0289969 A1    Oct. 11, 2018

Related U.S. Application Data

(60) Provisional application No. 62/481,937, filed on Apr. 5, 2017.

(51) Int. Cl.
*A61N 1/378*    (2006.01)
*A61N 1/372*    (2006.01)
(Continued)

(52) U.S. Cl.
CPC .......... *A61N 1/3787* (2013.01); *A61N 1/0484* (2013.01); *A61N 1/0529* (2013.01);
(Continued)

(58) Field of Classification Search
CPC .. A61N 1/3787; A61N 1/0484; A61N 1/0529; A61N 1/37223; A61N 1/37514; A61N 1/37276; H02J 50/10; H02J 7/025
See application file for complete search history.

(56) References Cited

U.S. PATENT DOCUMENTS 7,003,353 B1 * 2/2006 Parkhouse ........... A61N 1/3787
                                                          607/45
7,651,506 B2   1/2010 Bova et al.
(Continued)

FOREIGN PATENT DOCUMENTS

WO      2004103465 A1   12/2004
WO   WO2007123147 A1    9/2009
WO      2009131723 A1   10/2009

OTHER PUBLICATIONS

International Preliminary Report on Patentability from International Application No. PCT/US2018/026325, dated Oct. 17, 2019, 9 pp.
(Continued)

*Primary Examiner* — Lynsey C Eiseman
*Assistant Examiner* — Jessandra F Hough
(74) *Attorney, Agent, or Firm* — Shumaker & Sieffert, P.A.

(57) ABSTRACT

Devices, systems, and techniques are described for use in recharging a power source of a cranially mounted implantable medical device. In one example, a wearable medical device includes a flexible body configured to cover at least a portion of a scalp of a head of a patient. A securing member is connected to the flexible body and configured to extend around a circumference of the head to stabilize the flexible body with respect to the scalp of the patient. A fixation member is configured to mount to a location of the flexible body and couple the flexible body to a recharge coil that is
(Continued)

configured to recharge the power source of the cranially-mountable implantable medical device.

36 Claims, 35 Drawing Sheets

(51) Int. Cl.
*A61N 1/05* (2006.01)
*A61N 1/04* (2006.01)
*H02J 7/02* (2016.01)
*H02J 50/10* (2016.01)
*A61N 1/375* (2006.01)

(52) U.S. Cl.
CPC ...... *A61N 1/37223* (2013.01); *A61N 1/37276* (2013.01); *A61N 1/37514* (2017.08); *H02J 7/025* (2013.01); *H02J 50/10* (2016.02)

(56) References Cited

U.S. PATENT DOCUMENTS

| | | | |
|---|---|---|---|
| 2008/0164844 A1* | 7/2008 | Kato | H02J 50/60 320/114 |
| 2009/0187062 A1 | 7/2009 | Saitoh | |
| 2009/0270951 A1* | 10/2009 | Kallmyer | A61N 1/3787 607/61 |
| 2010/0331918 A1 | 12/2010 | DiGiore et al. | |
| 2014/0025140 A1 | 1/2014 | Lui et al. | |
| 2014/0084860 A1 | 3/2014 | Jaax et al. | |
| 2017/0290389 A1* | 10/2017 | Copeland | A42B 3/32 |

OTHER PUBLICATIONS

International Search Report and Written Opinion of International Application No. PCT/US2018/026325, dated Jun. 14, 2018, 15 pp.
Communication pursuant to Article 94(3) EPC from counterpart European Application No. 18720858.2 dated Oct. 21, 2021, 5 pp.
Reasons for Rejection, and translation thereof, from counterpart Japanese Application No. 2019-55377, dated Jan. 5, 2022, 5 pp.

* cited by examiner

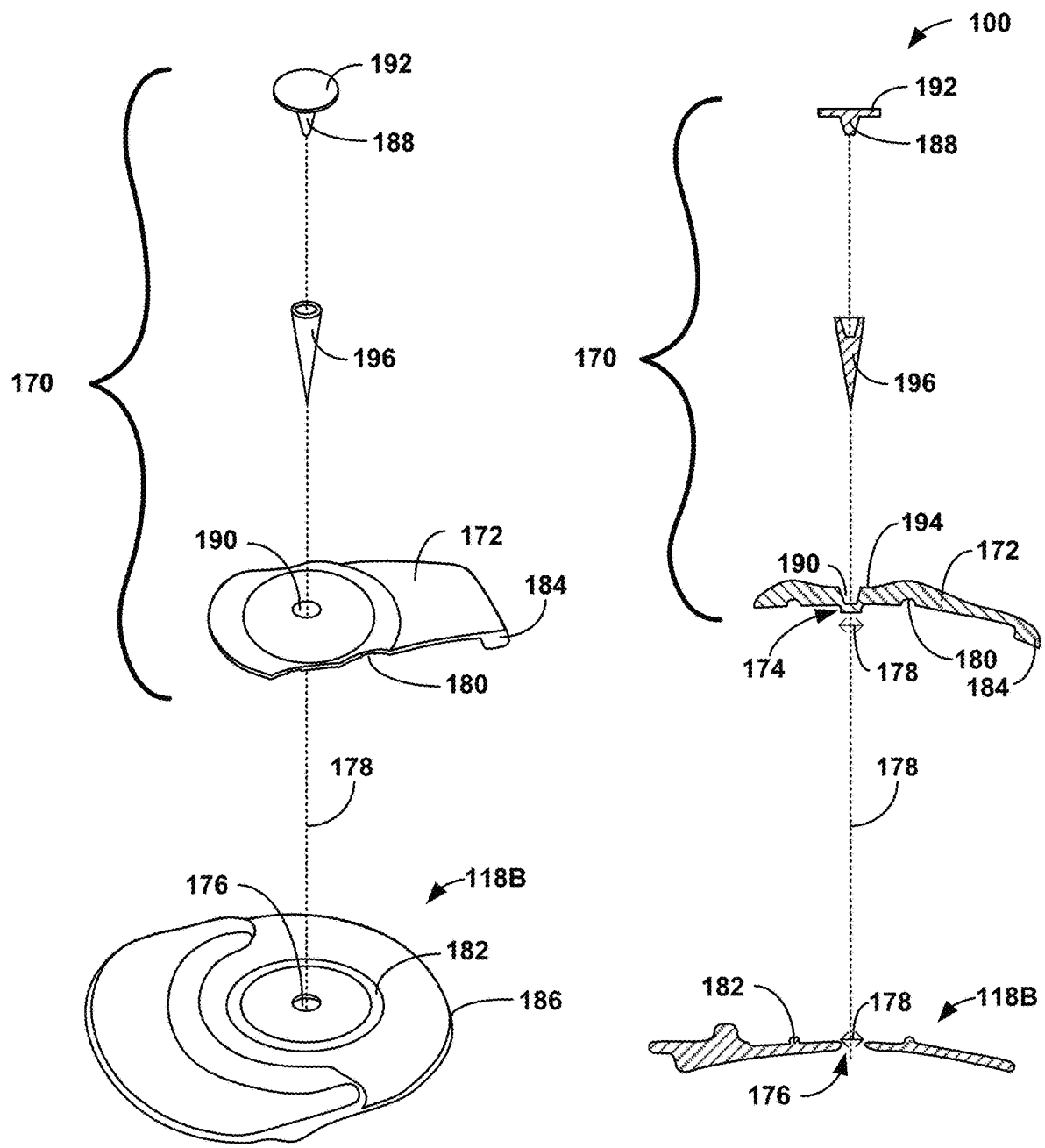
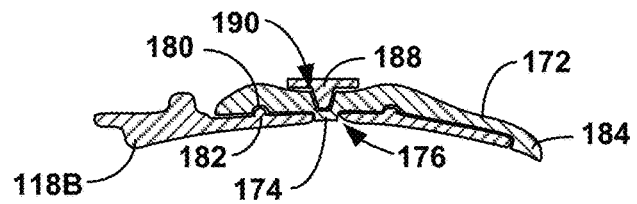
FIG. 6A  FIG. 6B
FIG. 6C

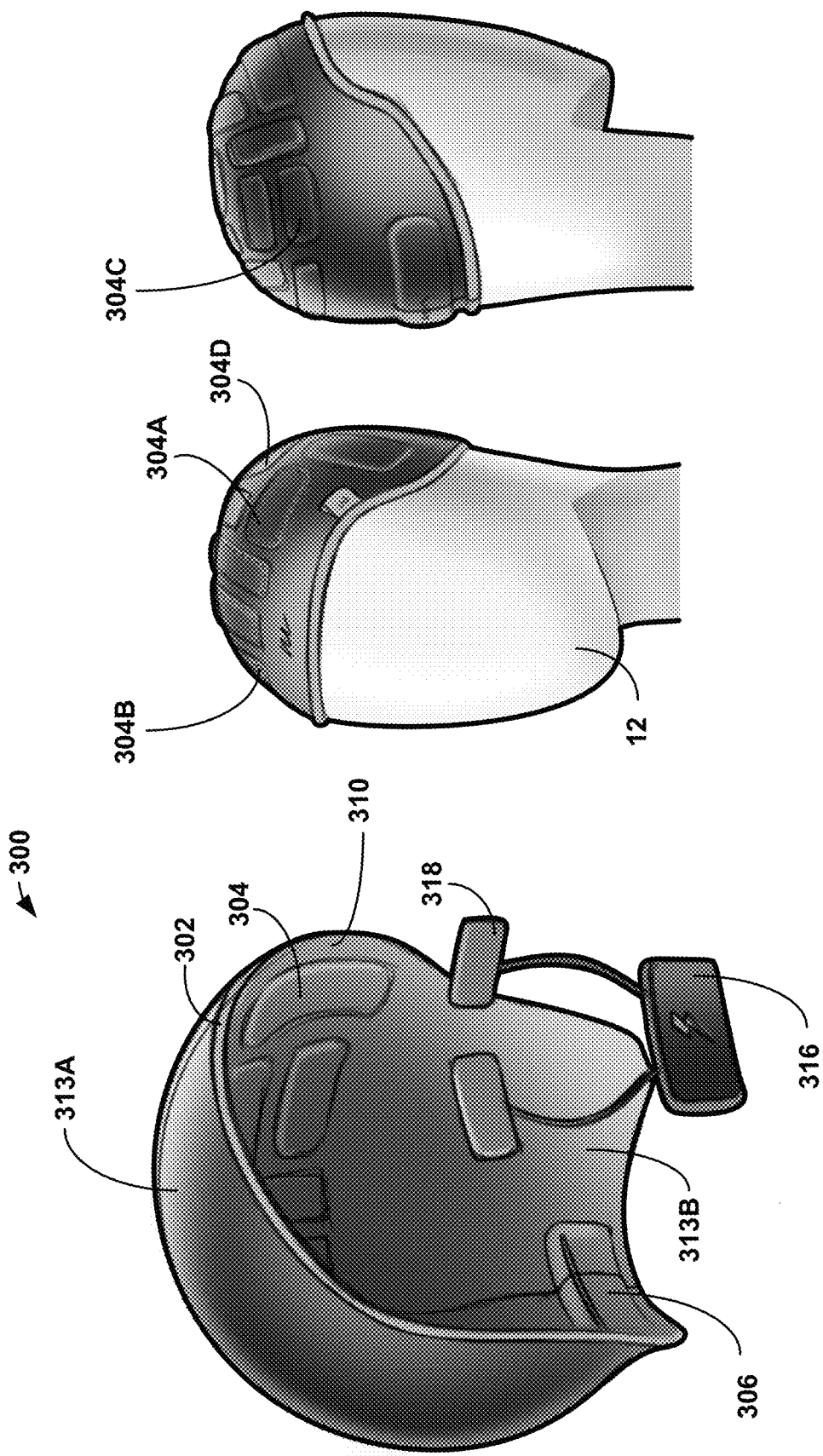

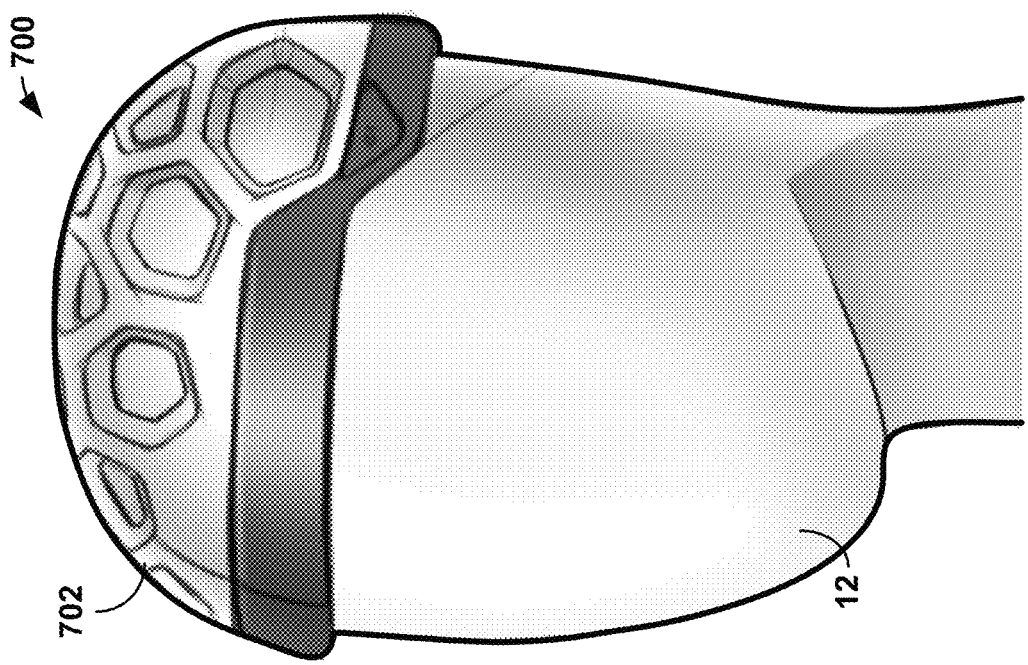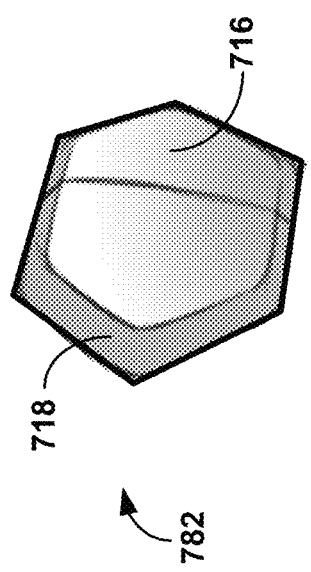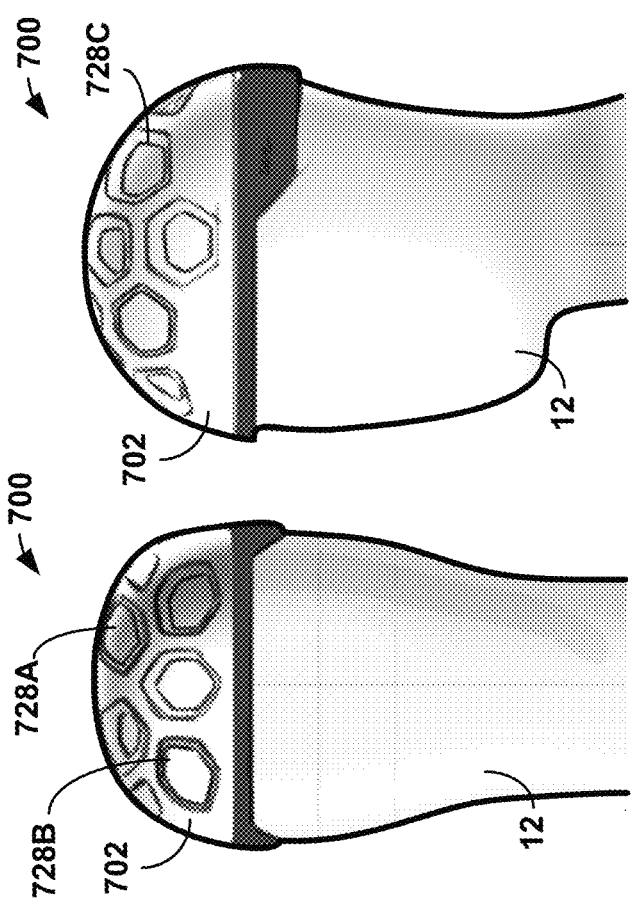

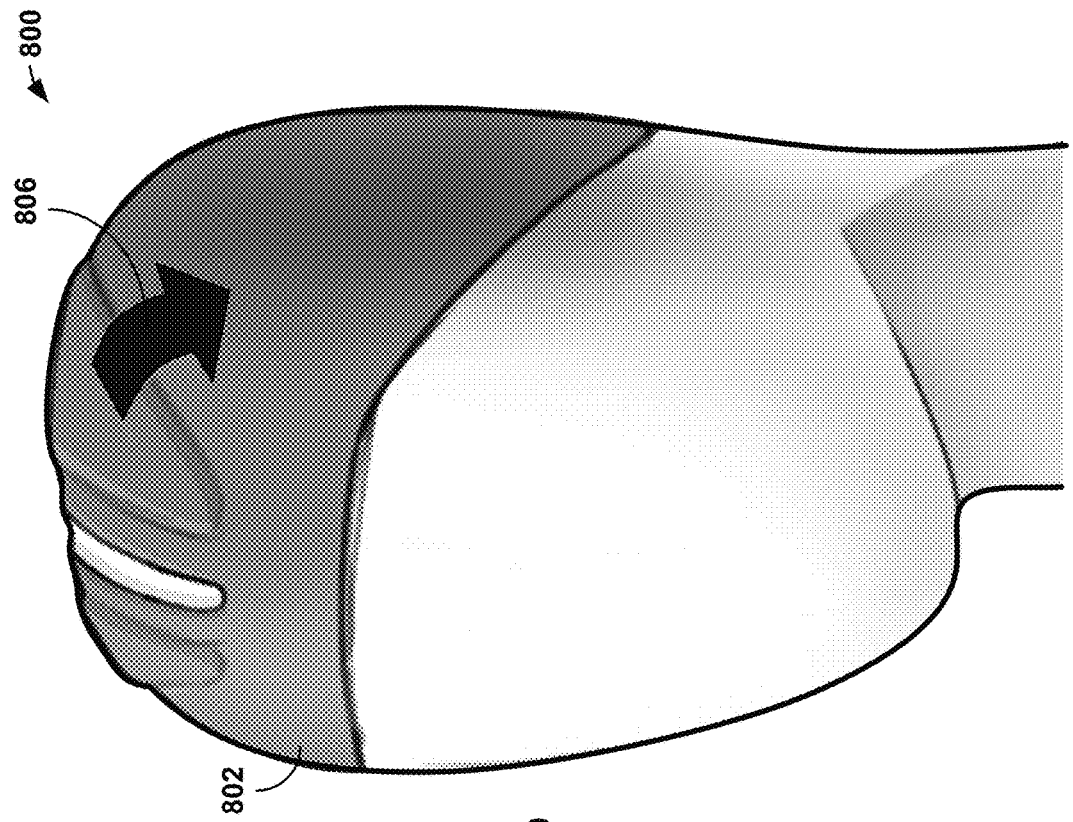
FIG. 15C
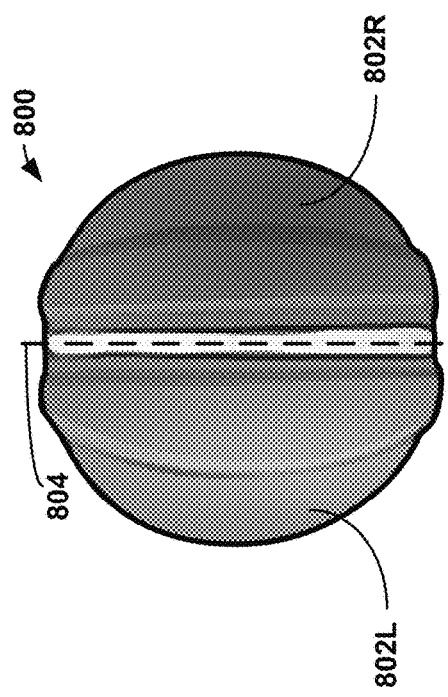
FIG. 15D
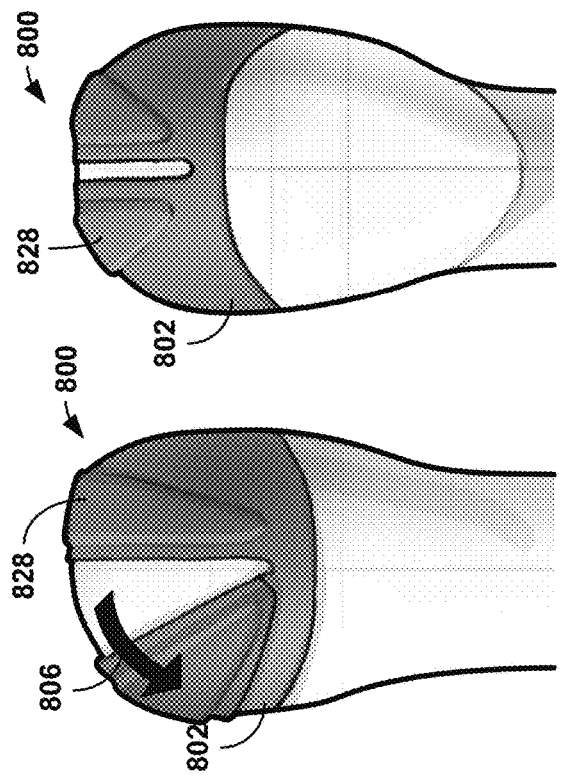
FIG. 15B
FIG. 15A

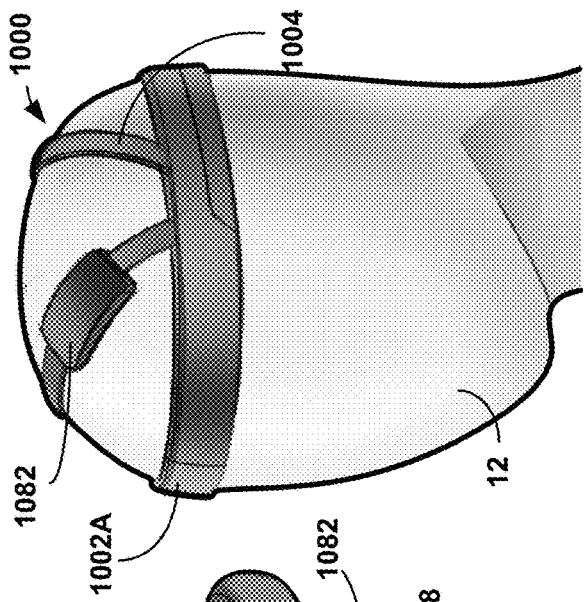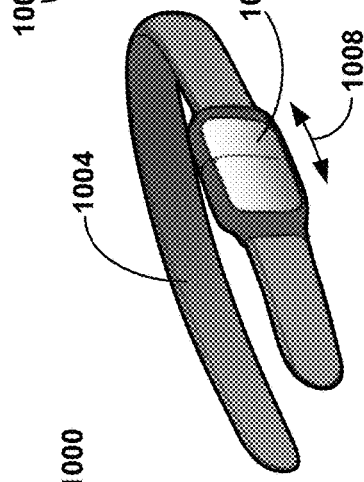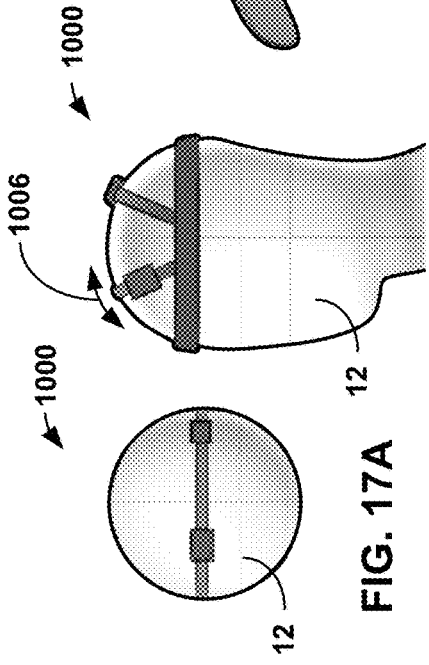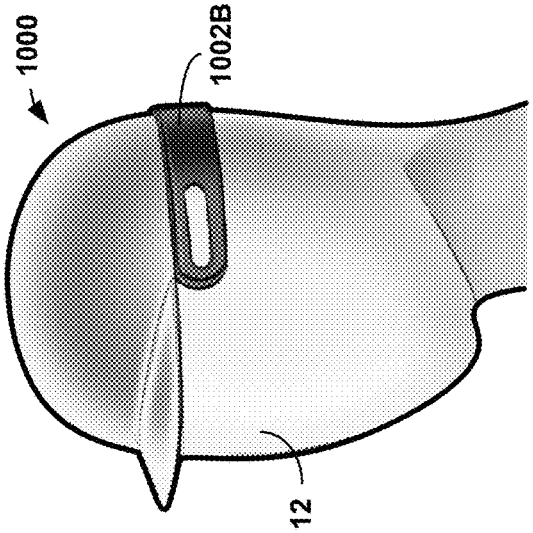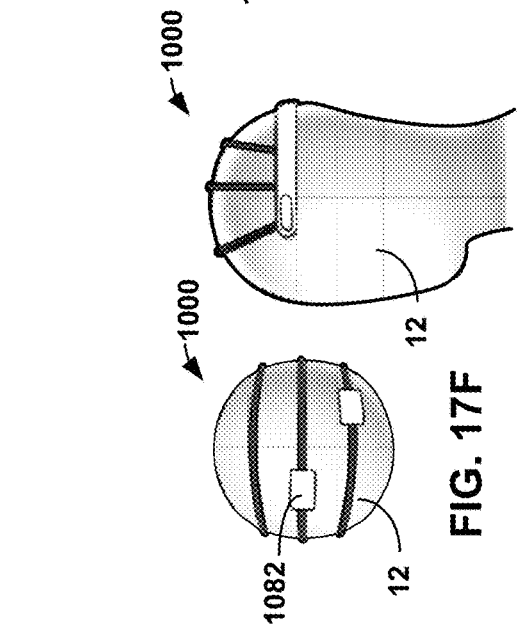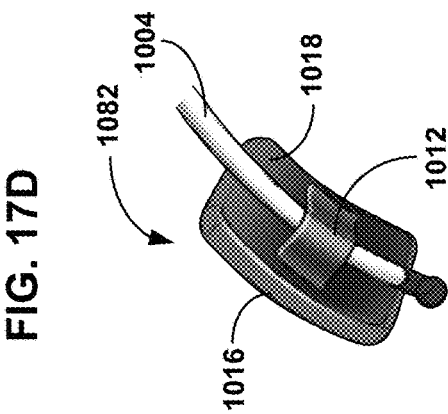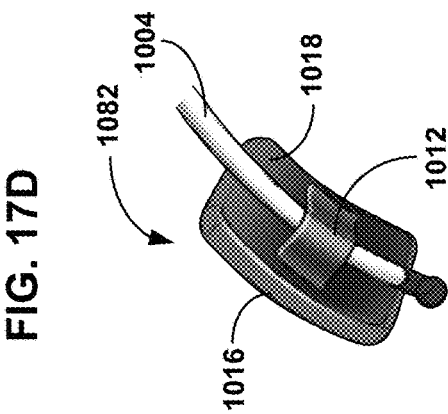

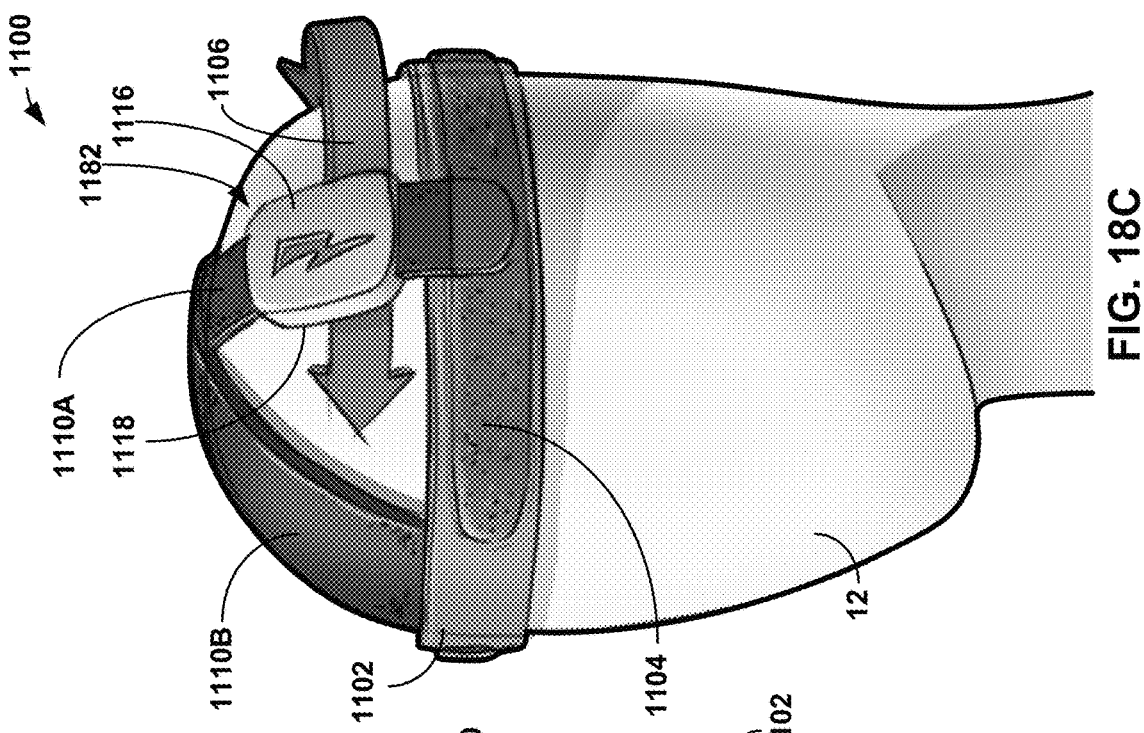
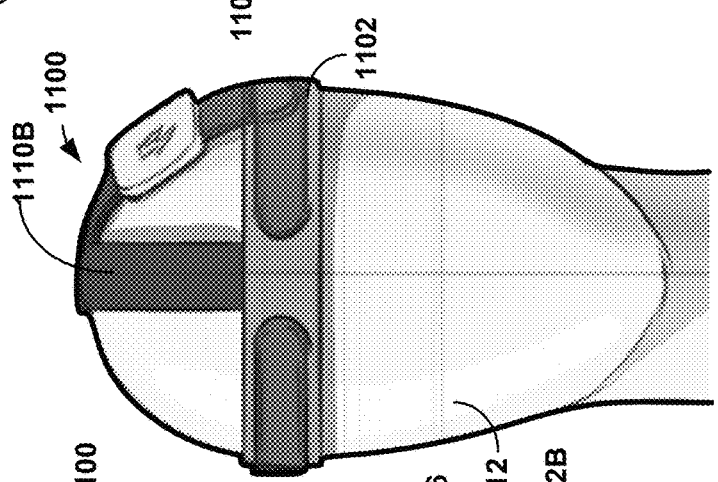
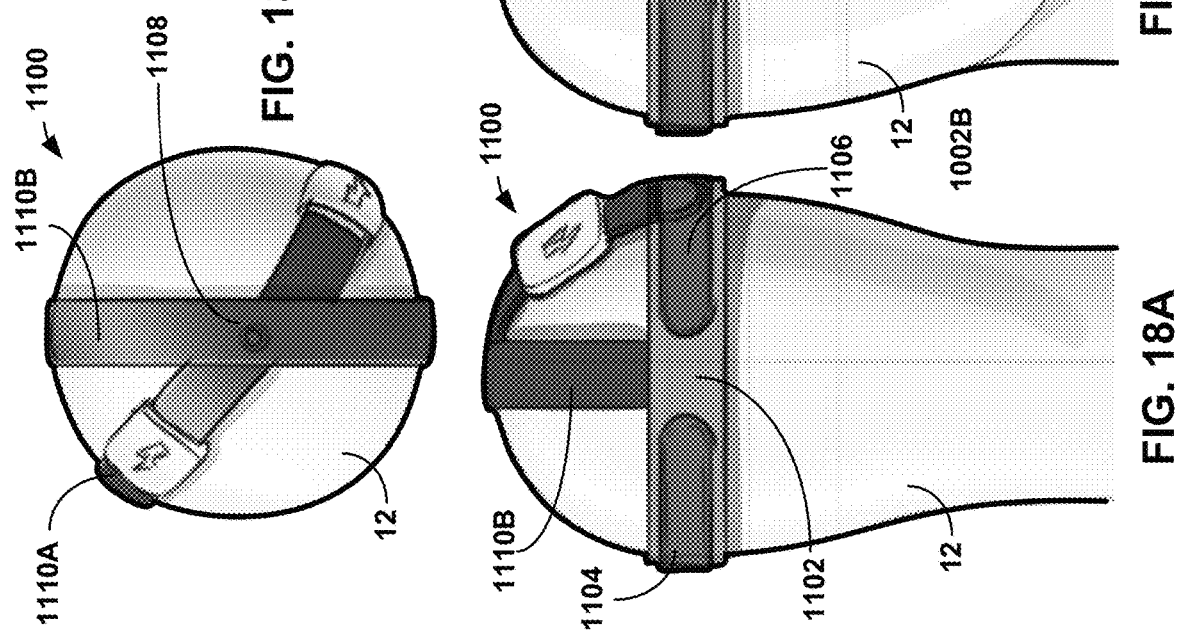
FIG. 18A   FIG. 18B   FIG. 18C   FIG. 18D

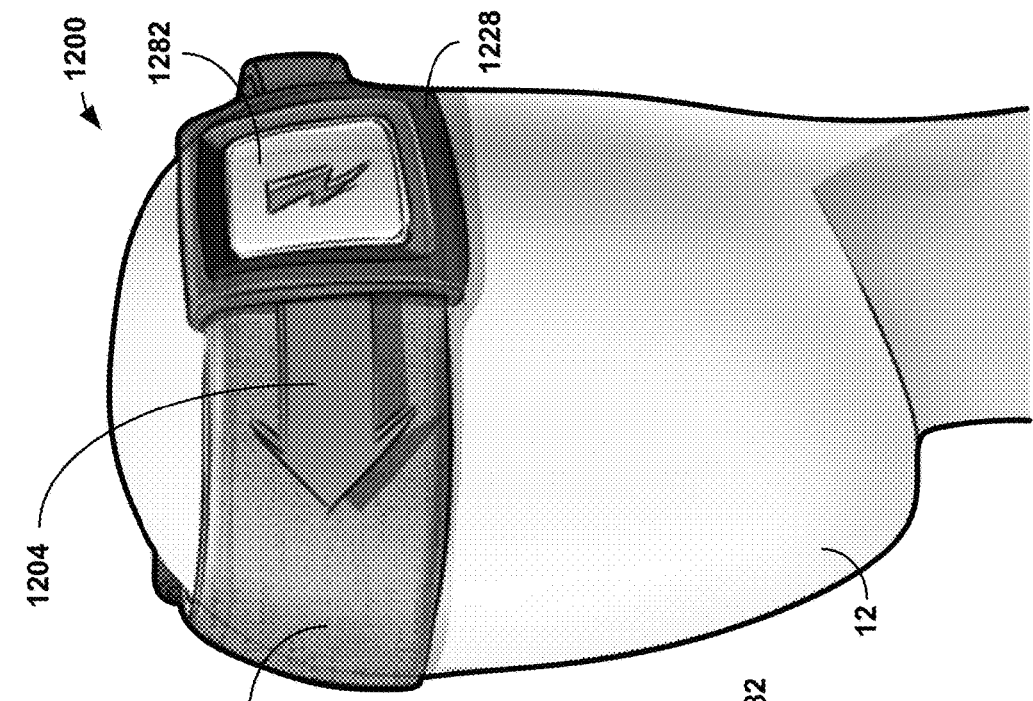
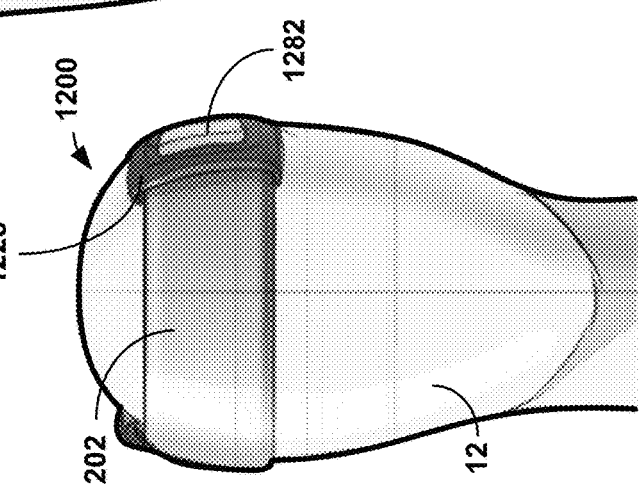
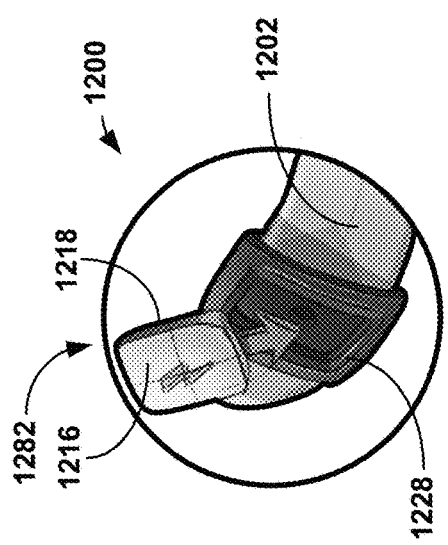
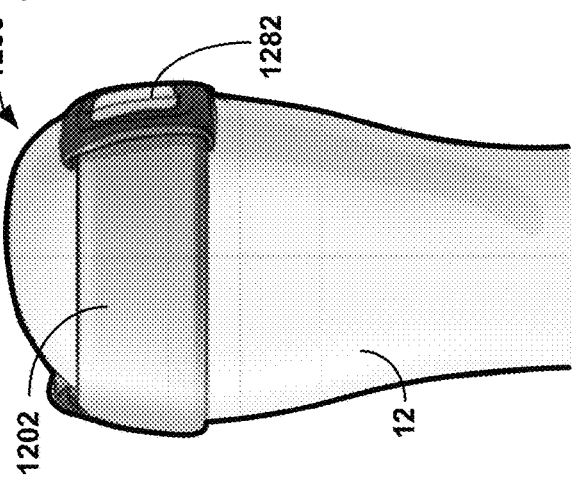
FIG. 19C
FIG. 19B
FIG. 19D
FIG. 19A

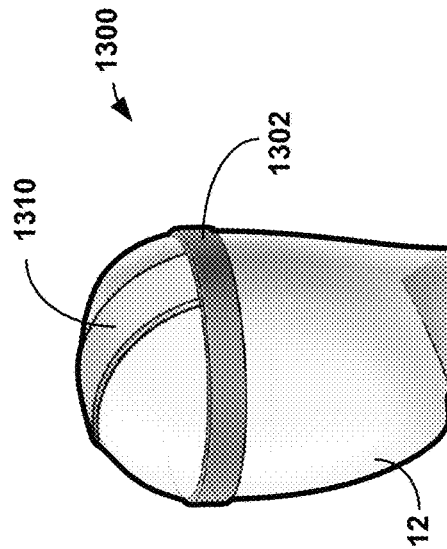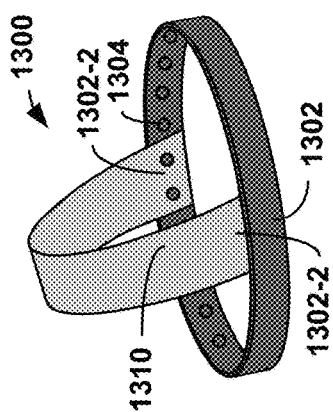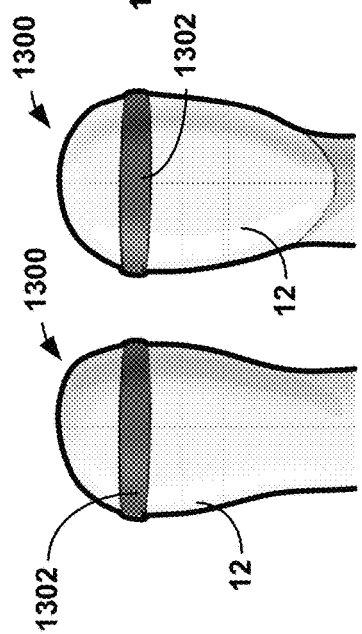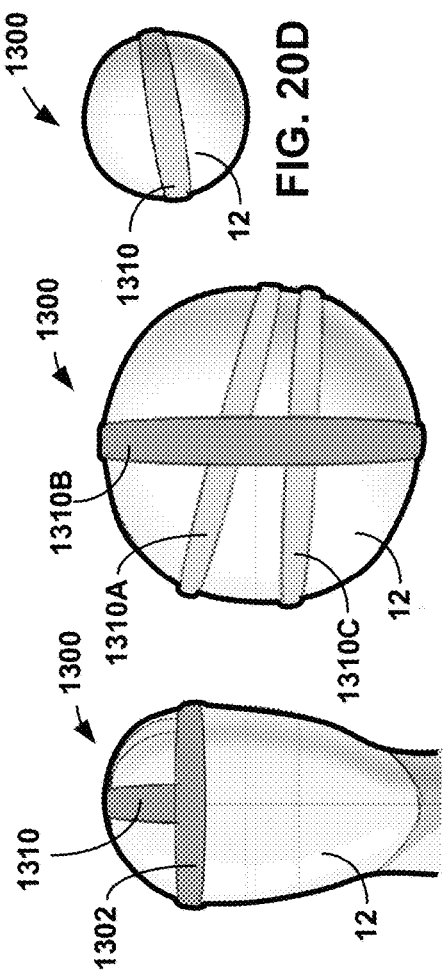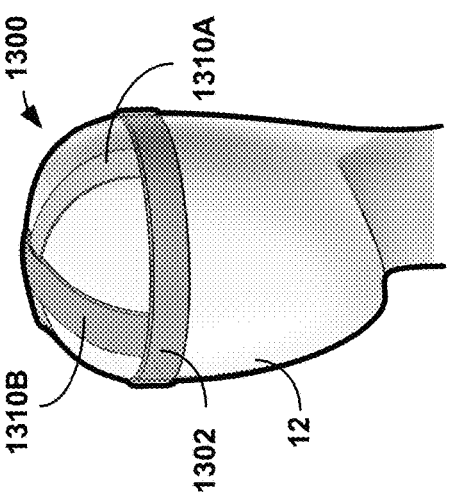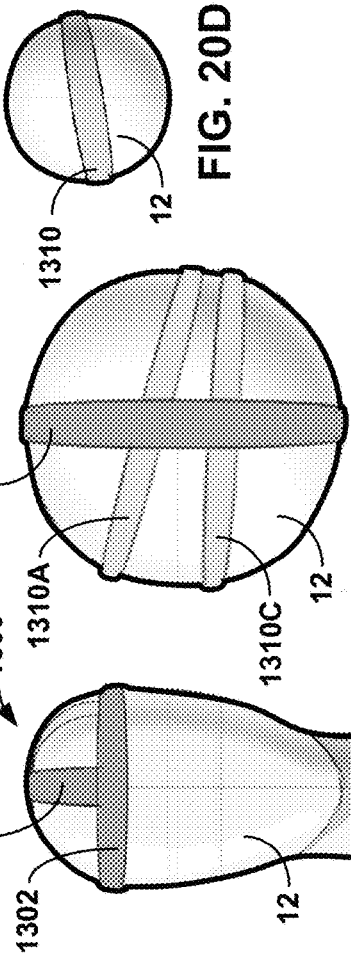

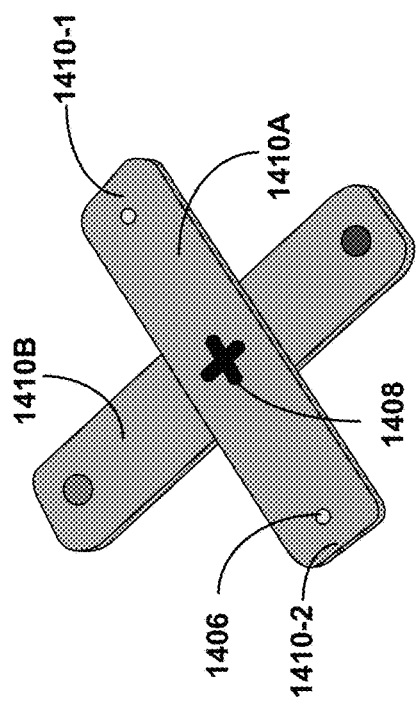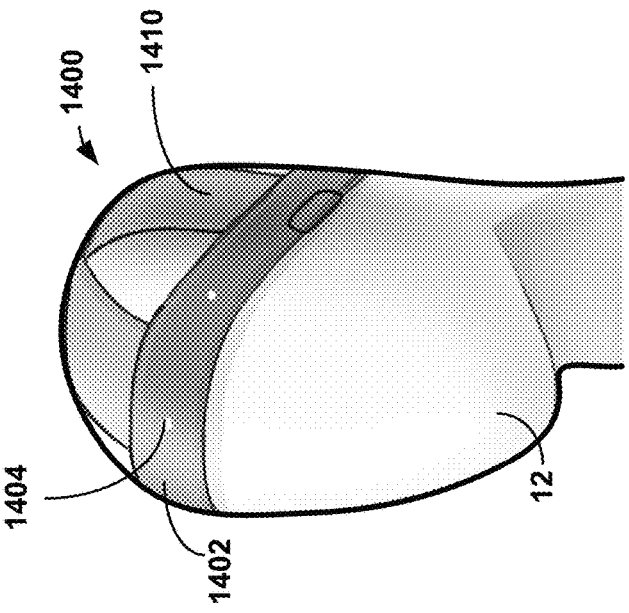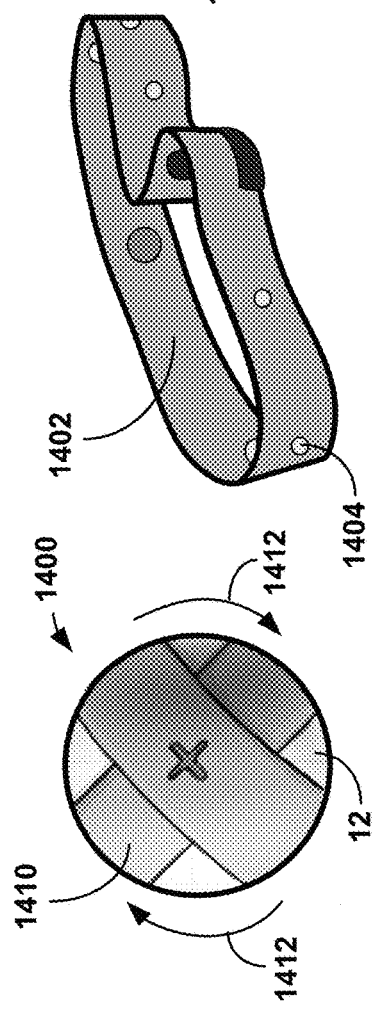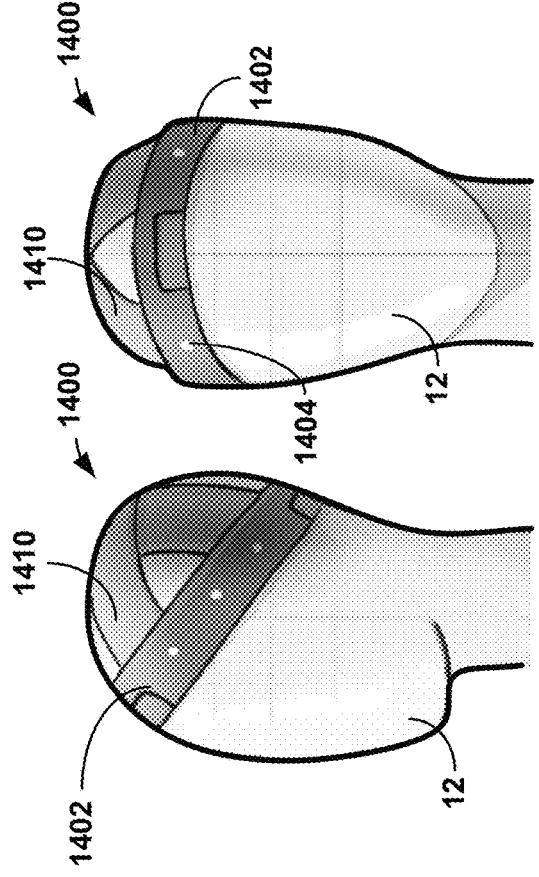

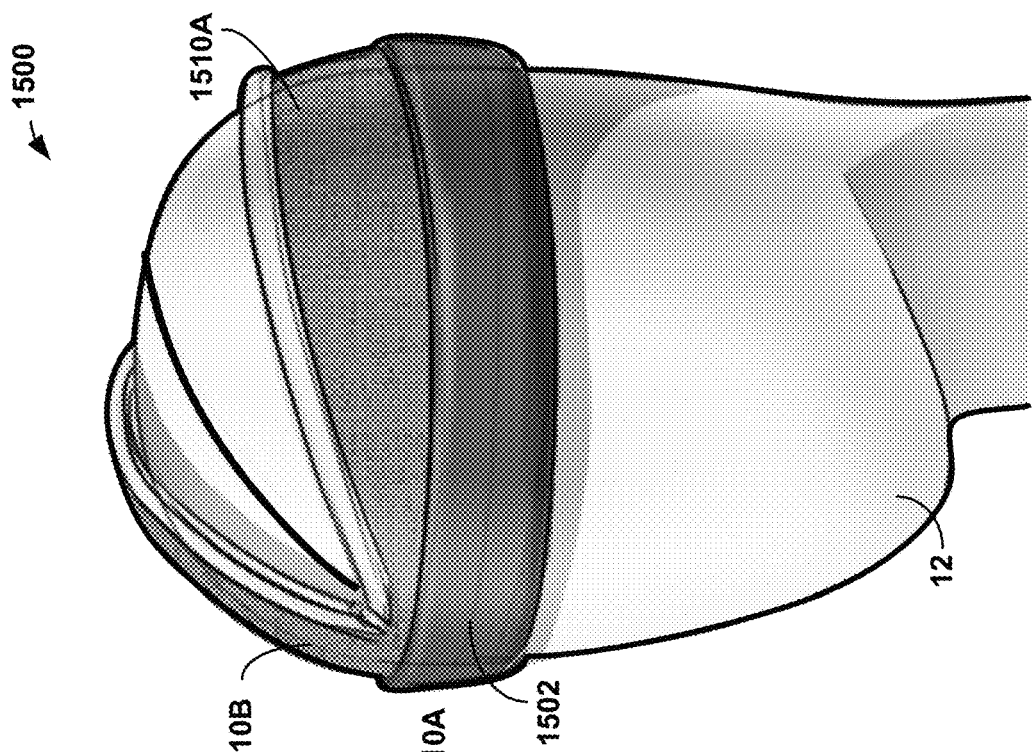
FIG. 22C
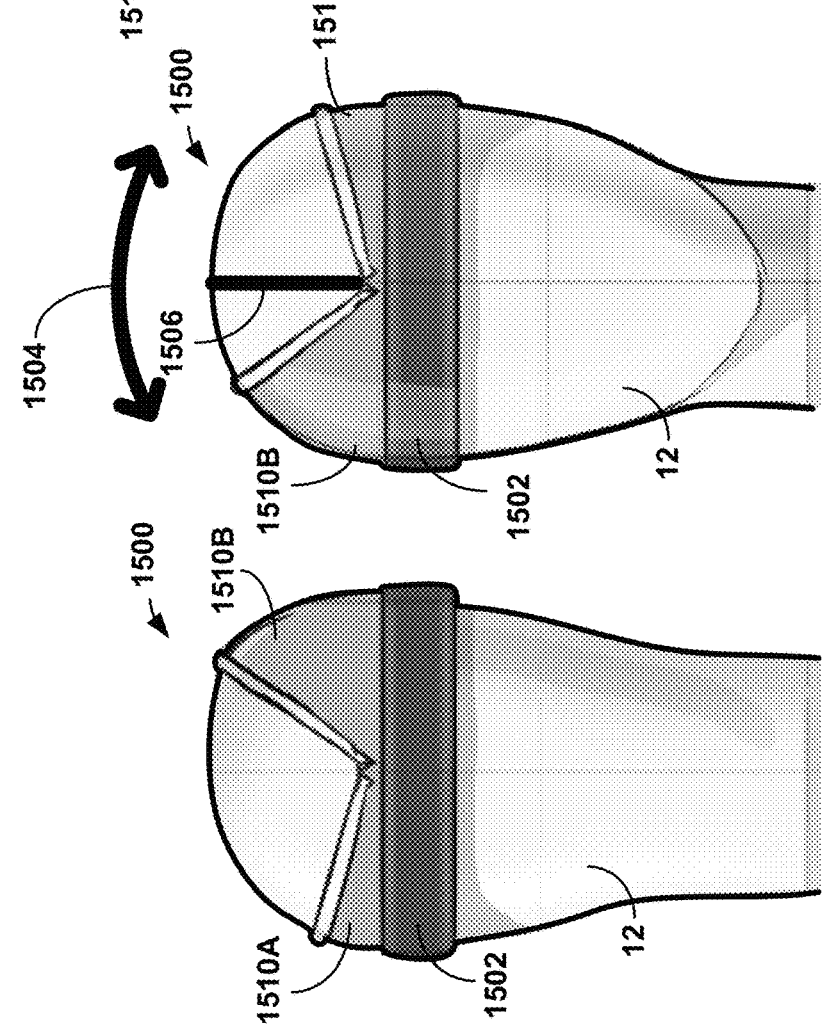
FIG. 22B
FIG. 22A

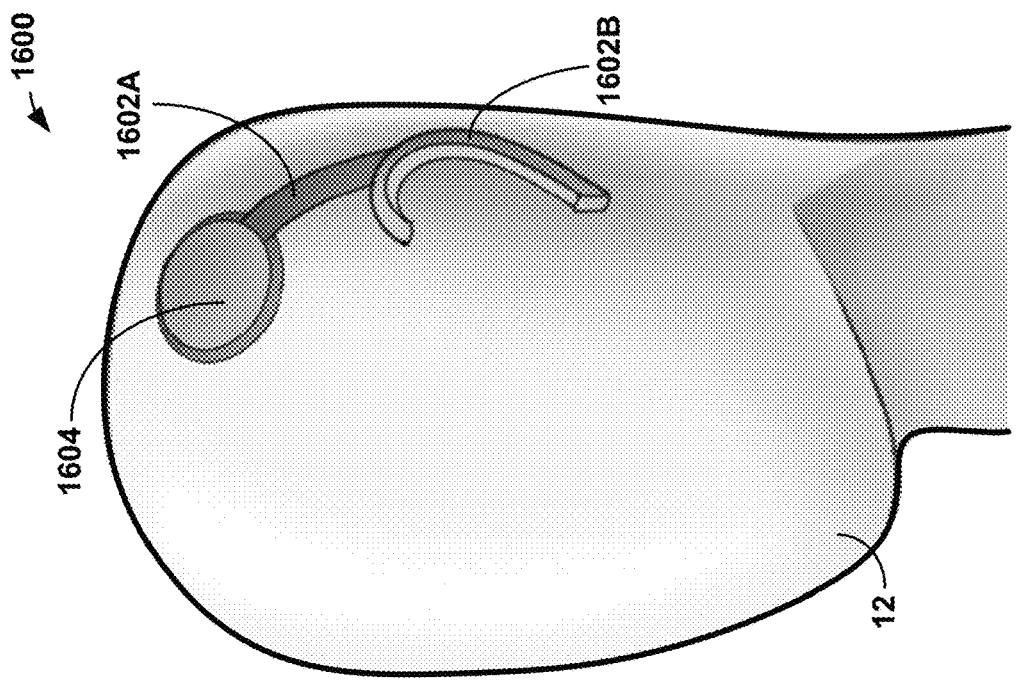
FIG. 23C
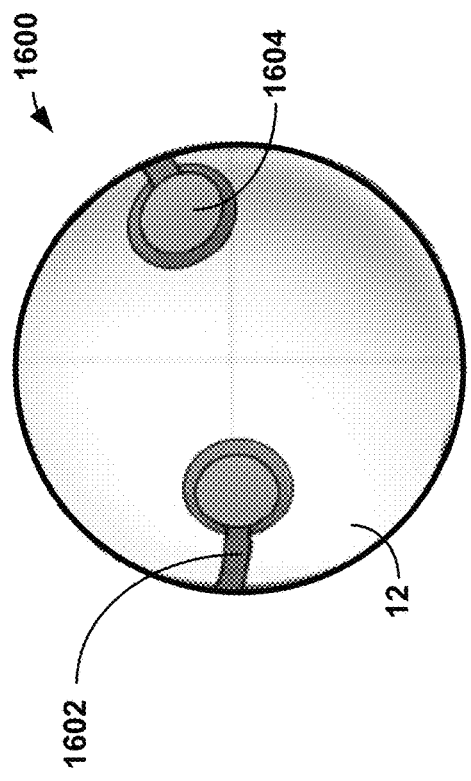
FIG. 23D
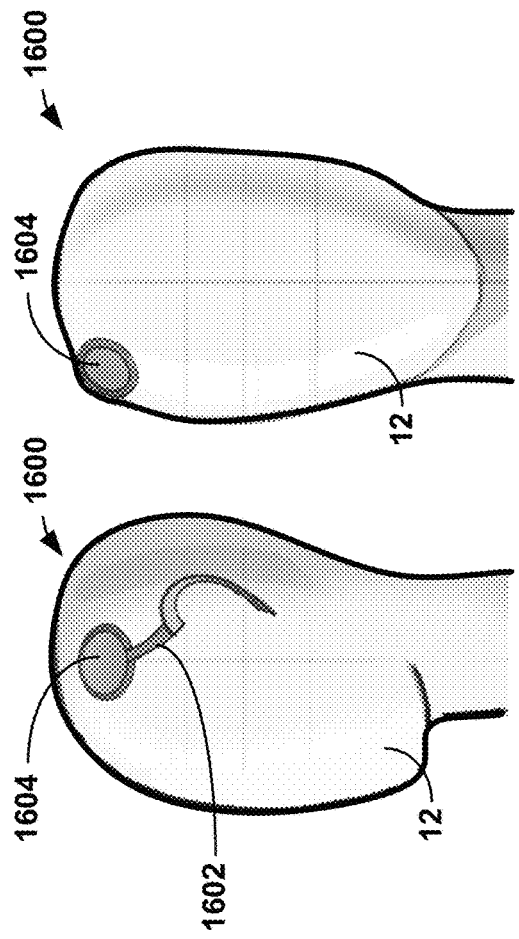
FIG. 23B
FIG. 23A

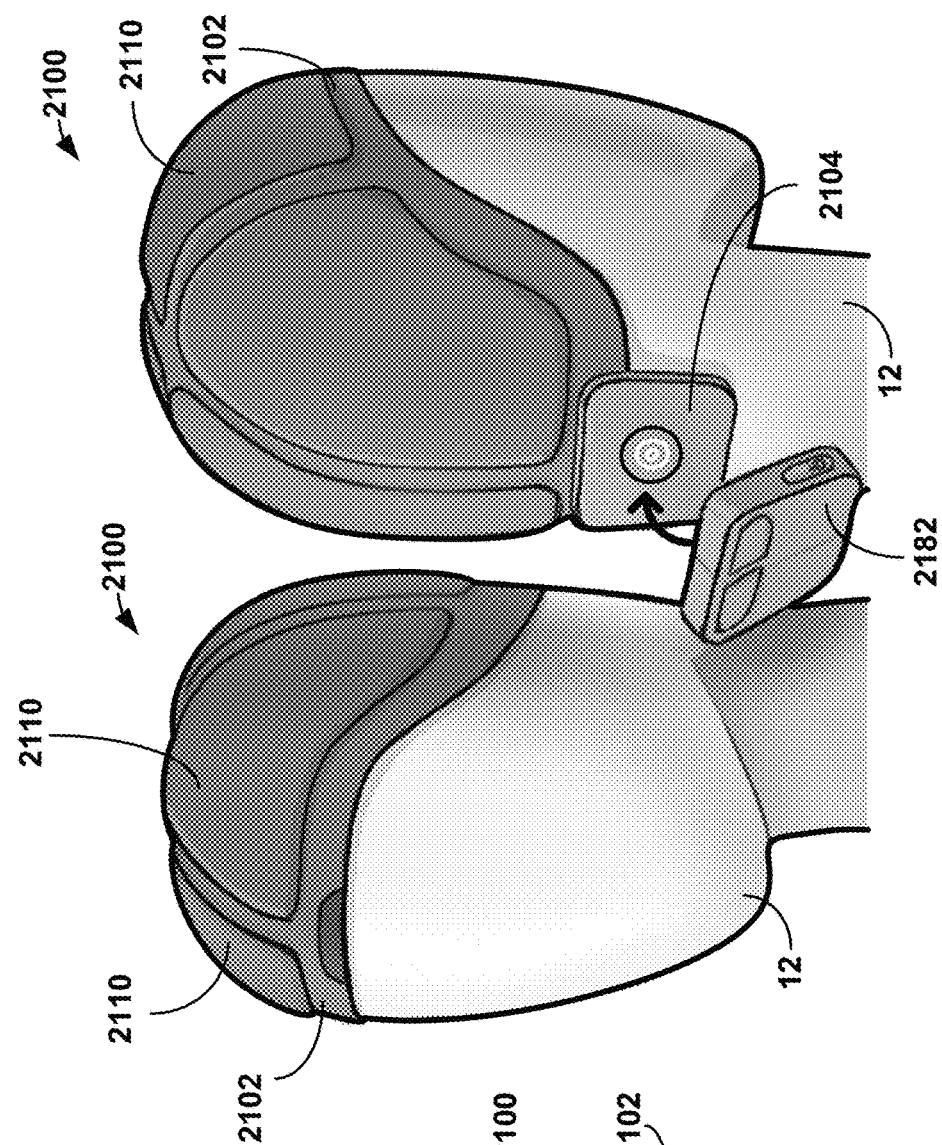
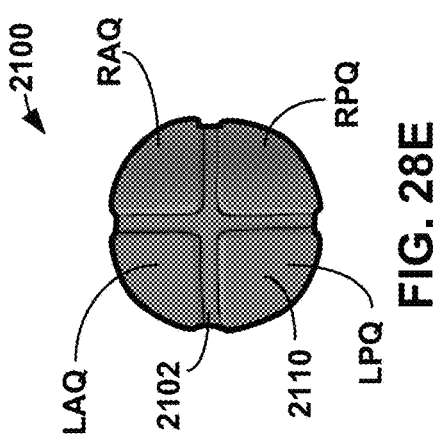
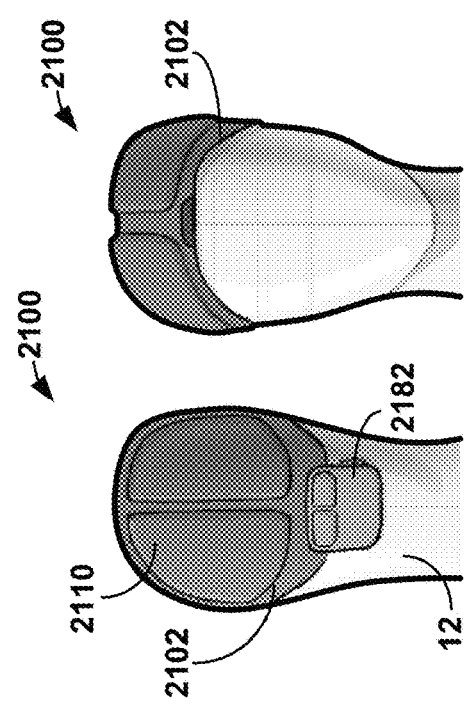
FIG. 28A  FIG. 28B  FIG. 28C  FIG. 28D  FIG. 28E

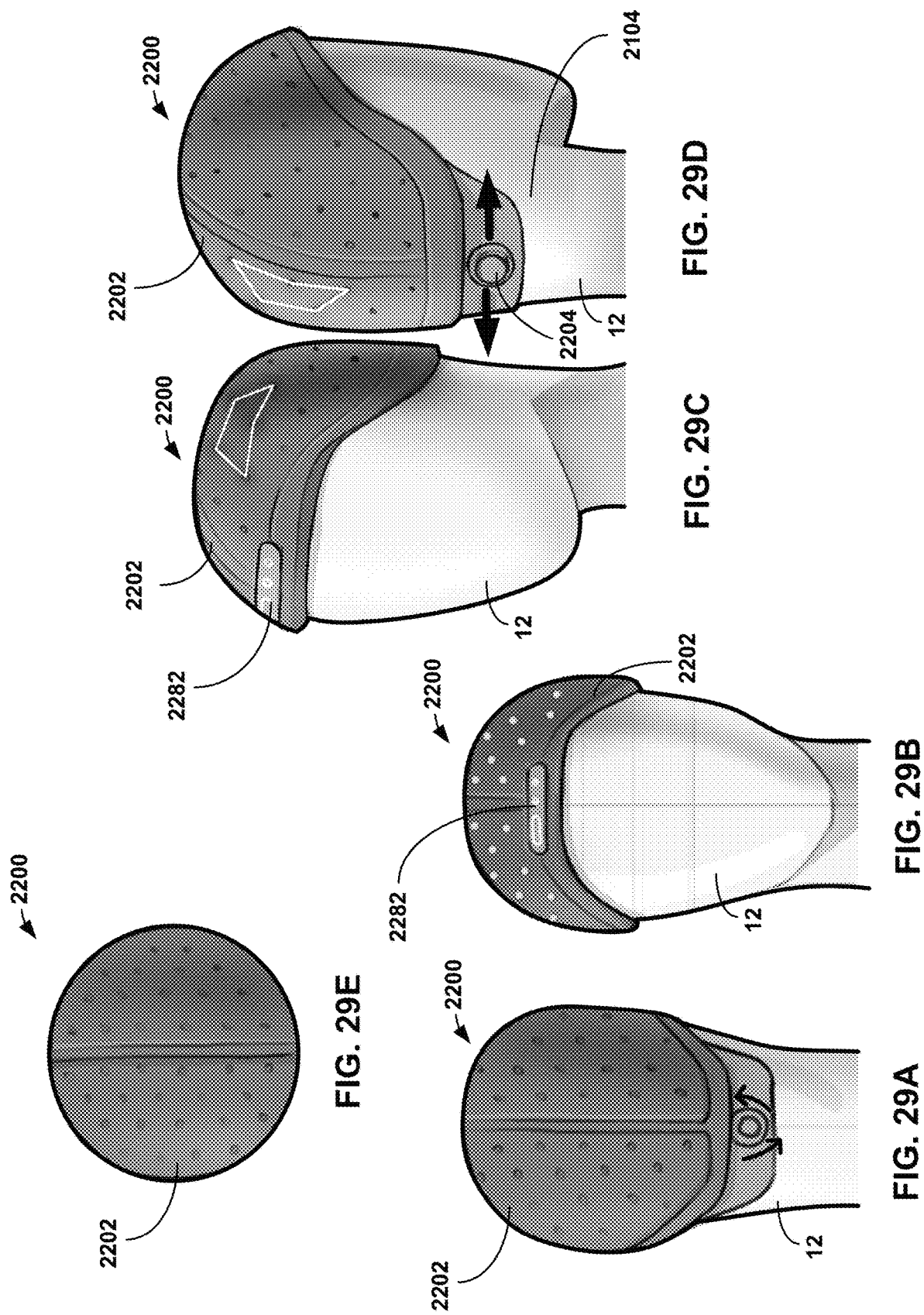

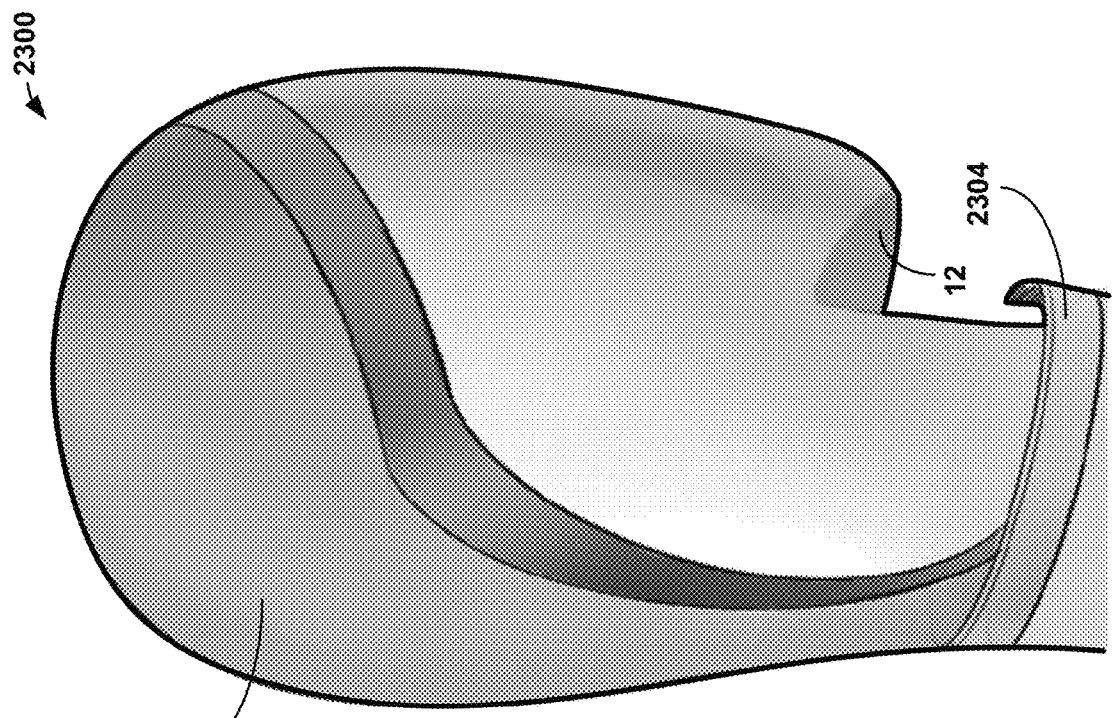
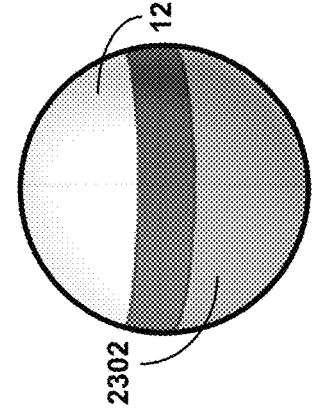
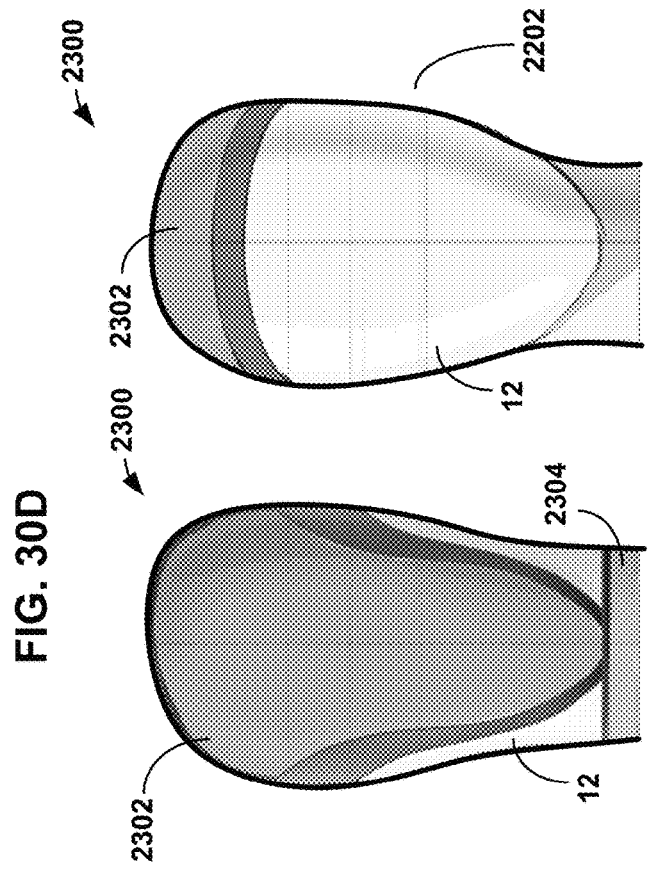
FIG. 30A
FIG. 30B
FIG. 30C
FIG. 30D

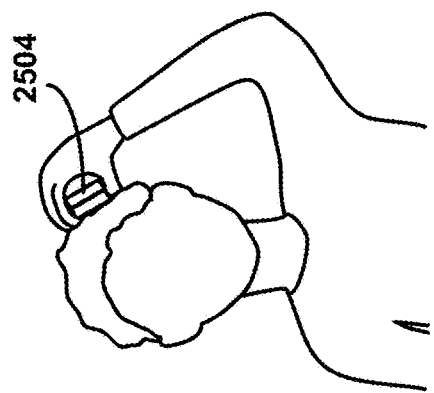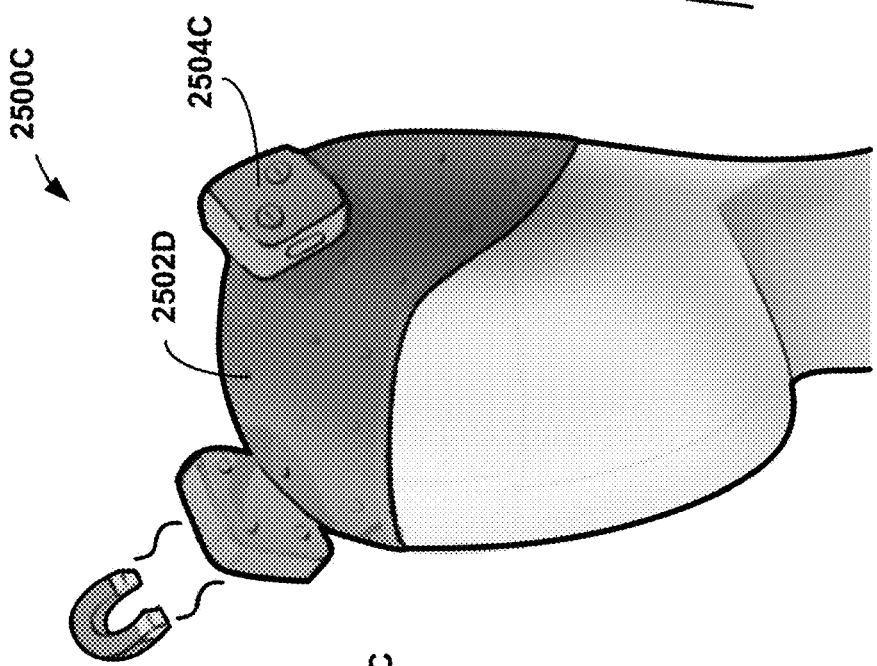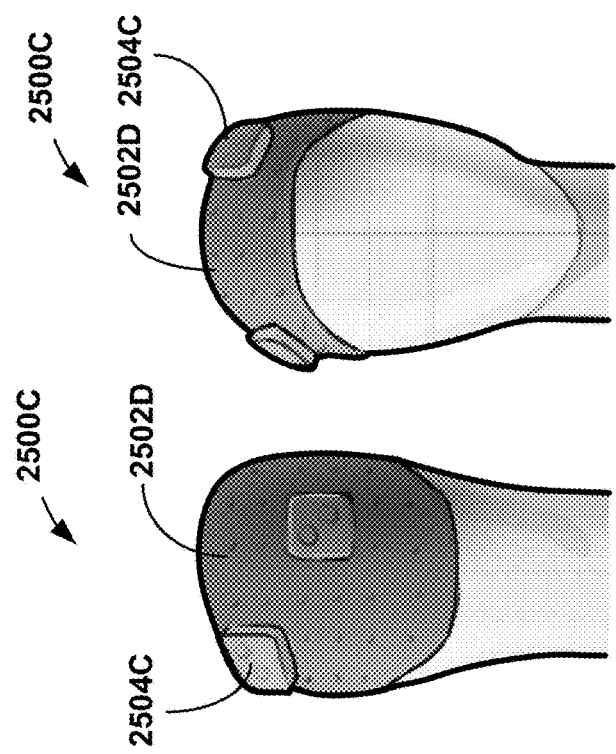
FIG. 33D
FIG. 33C
FIG. 33B
FIG. 33A

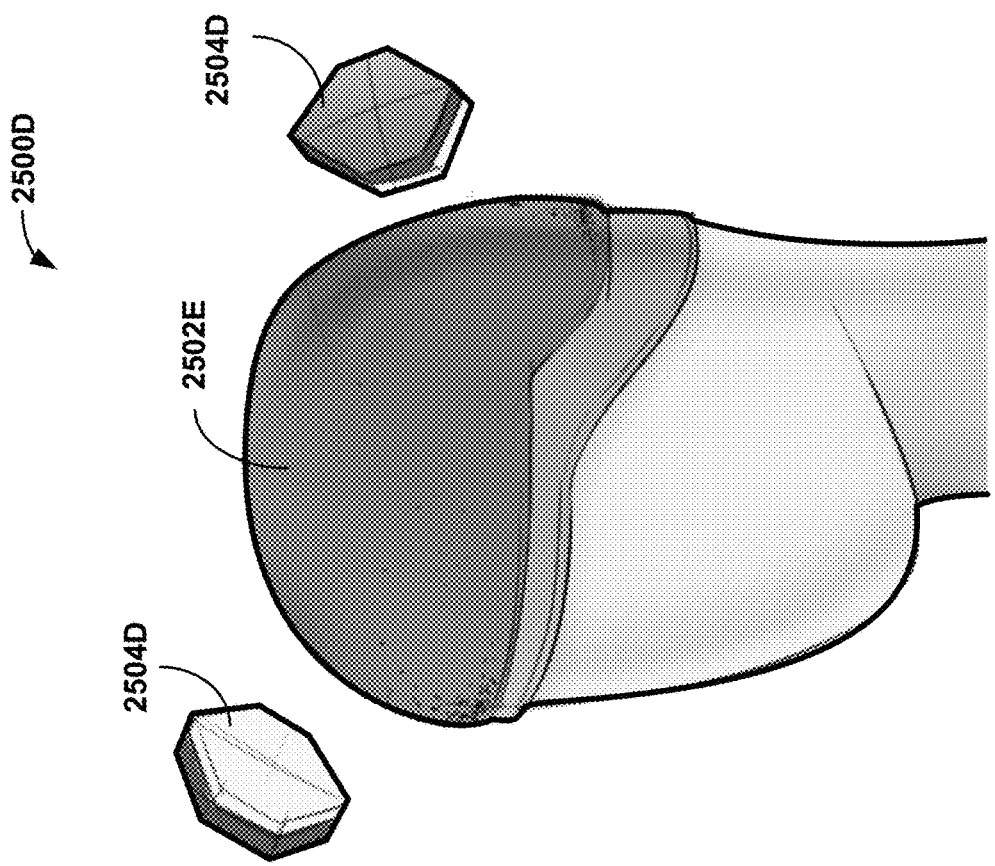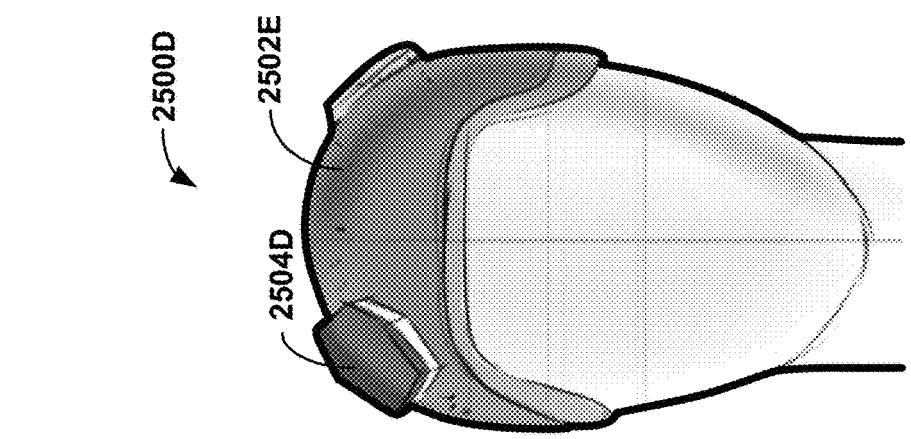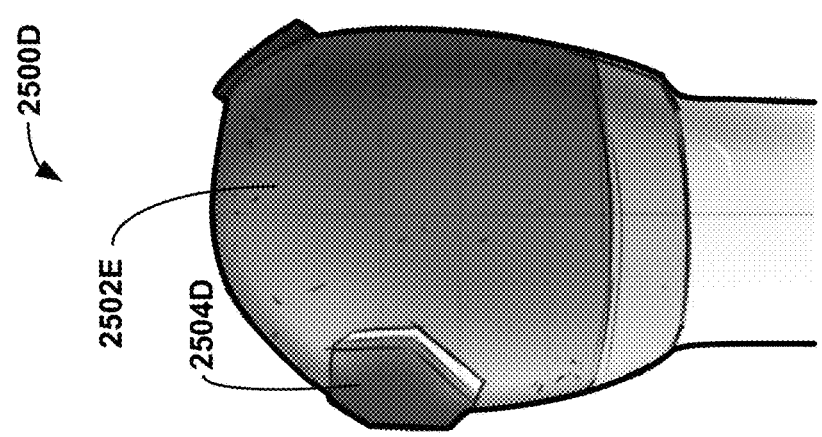

ASSEMBLIES AND HEADGEAR THEREOF FOR RECHARGING IMPLANTABLE MEDICAL ELECTRICAL SYSTEMS

This application claims the benefit of, and priority to, U.S. Provisional Patent Application Ser. No. 62/481,937, filed on Apr. 5, 2017, the entire content of which is incorporated by reference herein.

TECHNICAL FIELD

This disclosure is related to medical devices, and, more particularly, to assemblies and headgear associated with recharging a power source of one or more of the medical devices.

BACKGROUND

Medical devices may be configured to be external, partially implanted, or fully implanted at a plurality of locations within a patient to provide various functionality such as monitoring the patient and/or providing therapy to the patient. Examples of locations at which implantable medical devices (IMDs) may be implanted include on the cranium, at a substernal location, or near the hip of a patient, though IMDs may be implanted at other locations in other examples. IMDs may include one or more processing circuits and one or more electrical components that require power in order to provide the intended functionality. Often, a power source is housed within the IMD or otherwise also implanted to provide this functionality to the IMD. An IMD may include recharging components, such as recharging coils for inductive coupling, that are capable of recharging the embedded power source by, e.g., generating and directing current from an electromagnetic field to the power source of the IMD.

SUMMARY

This disclosure is related to devices, systems, and techniques related to recharging power sources of cranially mounted medical devices (e.g., one or more implantable medical devices (IMDs)). A wearable medical device may retain one or more recharging coils at a predetermined location appropriate for delivering charging power to one or more IMDs of the patient. For example, a wearable medical device may include a fixation member (e.g., an attachment assembly) configured to couple a recharging coil to a flexible body of the wearable medical device. A second fixation member may couple a second recharging coil to the flexible body. Since the patient may wear the wearable medical device over a portion of their head, the flexible body and the fixation members may retain the recharging coils at respective locations on the head that align with respective IMDs implanted on the cranium of the patient. In this manner, the patient may place the wearable medical device on their head to reproducibly align the recharging coils with the IMDs for recharging and/or communication functionality between the coils and the IMDs. The flexible body may have shape similar to a hat in some examples.

In some examples, the wearable medical device may include a recharging device, or recharging system, that is configured to be removably secured to the wearable medical device for use on the head of the patient. In this manner, the recharging device may be repeatably removed and secured to the head of the patient at reproducible locations with respect to the head. The recharging device may include one or more recharging coils and, in some examples, may also include a power source configured to supply power to the recharging coils. In some examples, the recharging coils may be secured to the flexible body, and the power source may be coupled to a securing member that extends around the circumference of the head and is more rigid than the flexible body.

In one example, a wearable medical system includes a flexible body that is configured to cover at least a portion of each of a left anterior quadrant, a left posterior quadrant, a right posterior quadrant, and a right anterior quadrant of a scalp of a head of a patient. The wearable medical system also includes a securing member connected to the flexible body and configured to extend around a circumference of the head and stabilize the flexible body with respect to the scalp of the patient. The wearable medical system also includes a fixation member configured to mount to a location of the flexible body and configured to couple the flexible body to a recharge coil configured to recharge an implantable power source of a cranially-mountable implantable medical device.

In another example, a wearable medical system includes a flexible body configured to cover at least a portion of each of a left anterior quadrant, a left posterior quadrant, a right posterior quadrant, and a right anterior quadrant of a scalp of a head of a patient. The wearable medical system also includes a securing member connected to the flexible body and configured to extend around a circumference of the head and stabilize the flexible body with respect to the scalp of the patient. The wearable medical system also includes an external power source secured to at least one of the flexible body or the securing member. The wearable medical system also includes a first recharge coil removably configured to transmit energy from the power source to recharge a first implantable power source of a first cranially-mountable implantable medical device. The wearable medical system also includes a second recharge coil removably configured to transmit energy from the power source to recharge a second implantable power source of a second cranially-mountable implantable medical device. The wearable medical system also includes one or more cables coupling the external power source to the first and second recharge coils. The wearable medical system also includes a first fixation member configured to mount to a first location of the flexible body and configured to securely attach the first recharge coil to the flexible body. The wearable medical system also includes a second fixation member configured to mount to a second location of the flexible body. The second fixation member is configured to securely attach the second recharge coil to the flexible body.

In another example, a wearable medical system includes a curved container that is configured to house a recharge coil and defines a concave first main surface and a convex second main surface that each approximate a curvature of a scalp of a head of a patient. The first main surface is configured to interface with the scalp of the patient and the second main surface is on an opposite side of the curved container of the first main surface. The second main surface defines a ridge that extends out away from the second main surface and a bore that extends through the curved container. The wearable medical system also includes a bracket defining a cylindrical recess configured to be received by the bore and a channel that is configured to receive the ridge of the second main surface to securely attach the bracket to the curved container. The wearable medical system also includes a pin configured to extend into the cylindrical recess of the bracket to be securely received by the bracket. The pin includes a plate configured to press a mouth of the cylindrical recess when the pin is received by the recess of the bracket.

More examples are set forth in the accompanying drawings and the description below. Other features, objects, and advantages of the disclosure will be apparent from the description and drawings, and from the claims.

BRIEF DESCRIPTION OF THE DRAWINGS

FIGS. 6A, 6B, and 6C are conceptual diagrams illustrating an exploded view, a cross-sectional exploded view, and a cross-sectional assembled view, respectively, of an example attachment assembly of the wearable medical device for securing components of the recharging device of FIG. 4A.

FIGS. 10A, 10B, and 10C are conceptual diagrams illustrating an example wearable medical device that may be used to recharge a power source of the IMD of FIG. 1A.

FIGS. 14A, 14B, 14C, and 14D are conceptual diagrams illustrating an example wearable medical device that may be used to recharge a power source of the IMD of FIG. 1A.

FIGS. 15A, 15B, 15C, and 15D are conceptual diagrams illustrating an example wearable medical device that may be used to recharge a power source of the IMD of FIG. 1A.

FIGS. 17A, 17B, 17C, 17D, 17E, 17F, 17G, and 17H are conceptual diagrams illustrating an example wearable medical device that may be used to recharge a power source of the IMD of FIG. 1A.

FIGS. 18A, 18B, 18C, and 18D are conceptual diagrams illustrating an example wearable medical device that may be used to recharge a power source of the IMD of FIG. 1A.

FIGS. 19A, 19B, 19C, and 19D are conceptual diagrams illustrating an example wearable medical device that may be used to recharge a power source of the IMD of FIG. 1A.

FIGS. 20A, 20B, 20C, 20D, 20E, 20F, 20G, 20H are conceptual diagrams illustrating an example wearable medical device that may be used to recharge a power source of the IMD of FIG. 1A.

FIGS. 21A, 21B, 21C, 21D, 21E, and 21F are conceptual diagrams illustrating an example wearable medical device that may be used to recharge a power source of the IMD of FIG. 1A.

FIGS. 22A, 22B, and 22C are conceptual diagrams illustrating an example wearable medical device that may be used to recharge a power source of the IMD of FIG. 1A.

FIGS. 23A, 23B, 23C, and 23D are conceptual diagrams illustrating an example wearable medical device that may be used to recharge a power source of the IMD of FIG. 1A.

FIGS. 28A, 28B, 28C, 28D, and 28E are conceptual diagrams illustrating an example wearable medical device that may be used to recharge a power source of the IMD of FIG. 1A.

FIGS. 29A, 29B, 29C, 29D, and 29E are conceptual diagrams illustrating an example wearable medical device that may be used to recharge a power source of the IMD of FIG. 1A.

FIGS. 30A, 30B, 30C, and 30D are conceptual diagrams illustrating an example wearable medical device that may be used to recharge a power source of the IMD of FIG. 1A.

FIGS. 33A, 33B, and 33C are conceptual diagrams illustrating an example recharge module that may be used with any of the example wearable medical devices of FIGS. 4A-31C.

FIG. 33D is a conceptual diagram illustrating the example recharge modules of FIGS. 33A-33C being used to recharge a power source of the IMD of FIG. 1A.

FIGS. 34A, 34B, and 34C are conceptual diagrams illustrating an example recharge module that may be used to recharge a power source of an IMD using the example wearable medical devices of any of FIGS. 4A-31C.

DETAILED DESCRIPTION

Figure 1A:
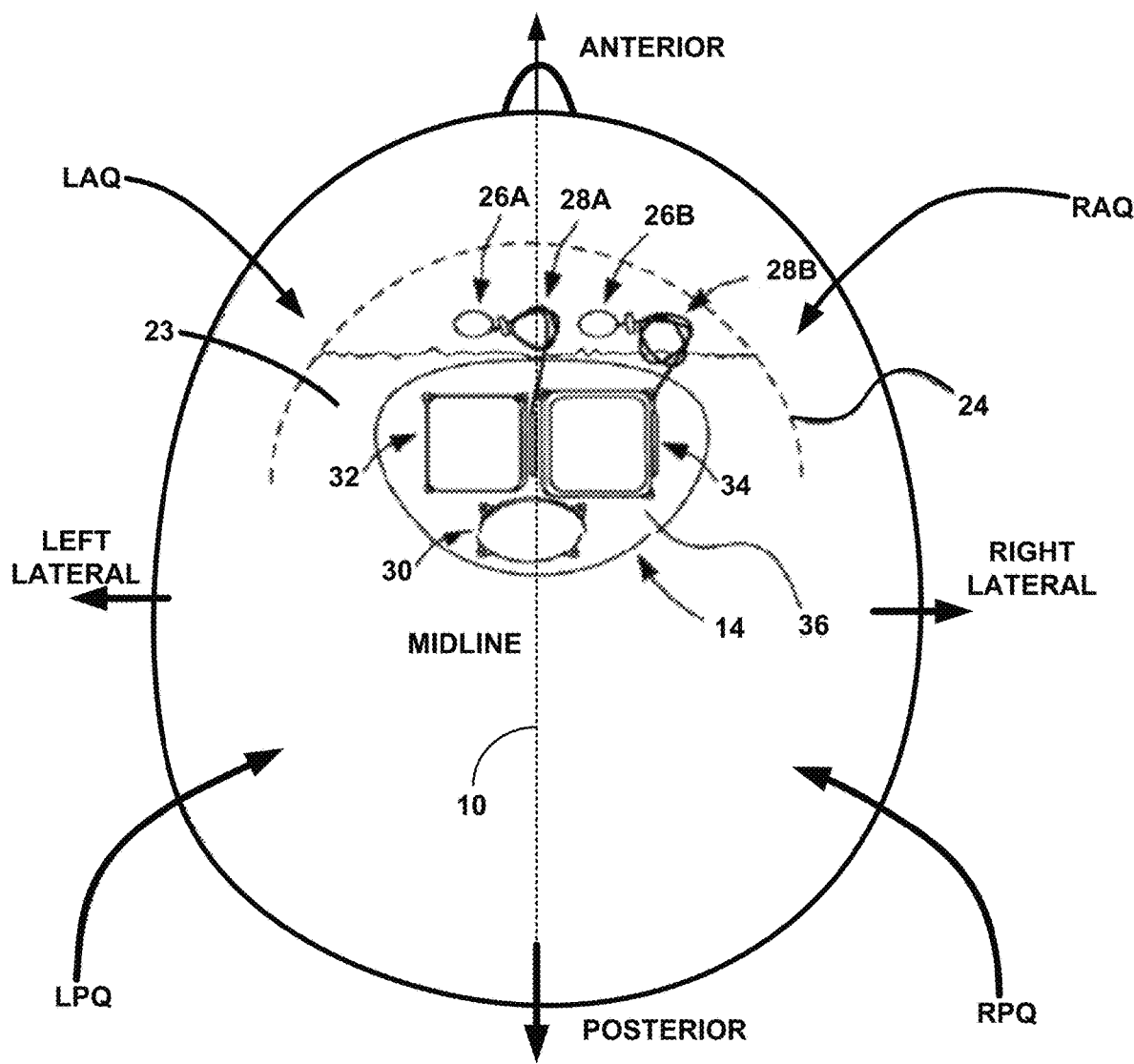
FIG. 1A is a conceptual diagram illustrating an example implantable medical devices (IMDs) that have been implanted on the cranium of a patient.

This disclosure is directed to devices, systems, and methods related to recharging power supplies of cranially mounted medical devices, such as implantable medical devices (IMDs). A patient may be monitored and/or treated using one or more medical devices that are located on or near the head of the patient. The medical devices may be completely external to the patient, partially implanted within the patient, or fully implanted within the patient. For example, a patient may have two cranially mounted IMDs coupled to respective electrical leads disposed within the brain, each IMD being configured to provide functionality such as monitoring or providing therapy to the brain patient (e.g., monitoring neurological signals and/or delivering deep brain stimulation to treat one or more symptoms of a brain disorder).

Each of these cranially-mounted IMDs may include a rechargeable power source that is configured to provide the power necessary to execute functionality of the IMD. The IMDs may each include a recharging coil configured to generate an electrical current to recharge the respective power sources in response to being exposed to an electromagnetic field from an external recharging coil (e.g., via inductive coupling). In addition, or alternatively, the IMD may receive communications from an external device via a coil. The efficiency, and speed, of energy transferred between the external recharging coil and the coils of the IMDs may be related to an alignment of the external recharging coil to the respective coil of the IMDs. Recharging sessions may take several minutes to over an hour. However, it may be difficult for a patient to manually hold the recharging coils to their head for the duration of the recharging session, difficult to maintain the appropriate positions of the external recharging coils for the duration of the recharging session, and/or difficult for the patient to initially find the correct position of each recharging coil with respect to the coils of the IMDs.

Aspects of this disclosure relate to removably securing a recharging device to the head of a patient via a wearable medical device, such that the wearable medical device, and the recharging device, may be repeatably secured to and removed from the head of the patient. The recharging device may be configured to create an electromagnetic field that is aligned with each recharging coil of each cranially mounted IMD each time that the charging device is secured to the head of the patient. For example, the recharging device may be attached to a wearable medical device which secured to the head of the patient. Once the wearable medical device is in place on the patient's head, the recharging coils of the recharging device can operate to create respective electromagnetic fields that are aligned with respective recharging coils of the IMDs, such that both power sources of both IMDs are simultaneously charged. In this manner, the wearable medical device may be configured to secure the recharging coils to respective locations of the wearable medical device, such that the wearable medical device assists the patient in reproducible placement of the recharging coils and maintaining the placement of the recharging coils with respect to the head of the patient for the duration of a recharging session. In some examples, the recharging coils may be removably attached to the wearable medical device using a fixation member such as an attachment assembly that may include a bracket or other structure configured to interface with the one or more recharging coils.

Examples disclosed herein are directed toward wearable medical devices and recharging devices configured to be removably secured to the head of a patient. The recharging devices are configured to facilitate the recharging of power source 56 in an implantable medical electrical system, such as that described above in conjunction with FIG. 1A when secured to the head of the patient via a wearable medical device. Examples of the wearable medical devices disclosed herein may be configured to hold a recharge coil of a recharging device or recharging system in place outside scalp 16 of the patient and in proximity to a rechargeable device of the medical device disposed outside of, at least partially within, or fully implanted beneath the scalp, for example, IMD 14. With further reference to FIG. 1A, it should be appreciated that the location along the skull of an implant site for IMD 14 can vary from patient to patient, for example, depending on the type of stimulation therapy or monitoring required. Further, in some cases, a patient may require more than one IMD 14, either of which may or may not be at the location depicted in FIG. 1A. Furthermore, IMD 14 recharging may be needed more than once per day in some examples, and the time required to recharge IMD 14 may be on the order of minutes, tens of minutes, greater than an hour, or at least several hours.

The following detailed description is exemplary in nature and is not intended to limit the scope, applicability, or configuration of inventive embodiments disclosed herein in any way. Rather, the following description provides practical examples, and those skilled in the art will recognize that some of the examples may have suitable alternatives. Examples will hereinafter be described in conjunction with the appended drawings, which are not to scale (unless so stated), wherein like numerals/letters denote like elements. Annotations of exemplary additional description included in the drawings are not intended to limit the scope of the illustrated embodiments. Examples of constructions, materials, dimensions and fabrication processes are provided for select elements and all other elements employ that which is known by those skilled in the art.

Certain types of implantable medical electrical systems are employed to treat nervous system conditions such as pain and/or psychological, sleep, or movement disorders. In some examples, these systems include at least one elongate implantable medical electrical lead electrically connected to an implantable pulse generator device (e.g., an IMD that includes a pulse generator), wherein the lead includes one or more electrodes that deliver electrical stimulation therapy to the patient from the generator device. For example, the electrodes may delivery deep brain stimulation, cortical stimulation, occipital nerve stimulation, or any other type of therapy. In other examples, the IMD may monitor brain activity or the activity of other anatomical structures. In other examples, the IMD may deliver drug therapy to the brain or other structure associated with the head of the patient.

FIG. 1A is a conceptual diagram of such an exemplary system implanted, from a superior view of a scalp 16 of the patient. The example of FIG. 1A illustrates an example implantable medical device (IMD) 14, to which leads 28A, 28B (collectively, "leads 28") are connected, wherein IMD 14 is implanted beneath a scalp 16 of the patient in a hollowed-out, or recessed, area of the patient's skull 23. IMD 14 may be an implantable pulse generator from which leads 28A, 28B extend to the brain of the patient through burr holes 26A, 26B (collectively, "holes 26") that have been drilled through the skull 23. Access to skull 23 of the patient for the implant may have been gained via a "C-flap" incision 24 formed through scalp 16 of the patient. "Hollowed out" may refer to any area where a portion or all of the skull was removed to make any room for IMD 14, either to partially or wholly fit device within that hollowed out area.

FIG. 1A further illustrates IMD 14 including housing 36, for example, formed from a relatively soft biocompatible material that contains and/or encapsulates electronic portions of IMD 14. For example, IMD 14 may include control module 34, power module 32, and recharge module 30 as depicted in FIG. 1A. Power module 32 includes a rechargeable power source, for example, a rechargeable battery. Recharge module 30 may be coupled to power module 32 and include a secondary coil configured to receive energy via transcutaneous inductive energy transmission (e.g., inductive coupling).

A wearable medical device and recharging device as described herein may be removably secured to scalp 16 of the patient such that when secured one or more recharge coils of the recharge device are located at a predetermined location relative to the scalp, and the implanted IMDs, of the patient. The predetermined location may be a location at which an electromagnetic field created by the recharge coils of the recharge device are relatively aligned with one or more secondary coils of recharge module 30 of IMD 14. The location may be aided by defining scalp 16 as different predetermined regions, such as the left anterior quadrant (LAQ), the right anterior quadrant (RAQ), the left posterior quadrant (LPQ) and the right posterior quadrant (RPQ) as labelled in FIG. 1. A "left" and "right" side of the head of the patient as per the LAQ, LPQ, RAQ, and RPQ may be divided along a longitudinal midline 10 of the head of the patient. In some examples, LAQ, LPQ, RAQ, and RPQ may extend across a scalp of the patient. Reference to each quadrant associated with a respective IMD may help to locate the recharge coils to the wearable medical device.

Figure 1B:
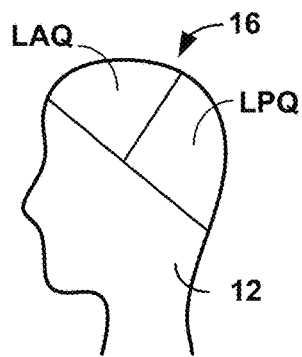
FIGS. 1B and 1C are side views from both sides of the example cranium in FIG. 1A.
Figure 1C:
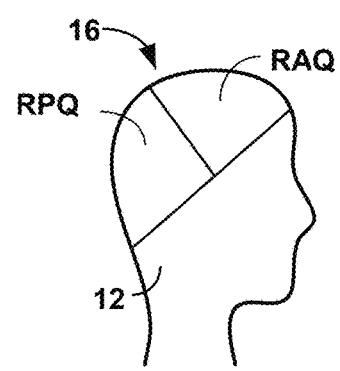

For example, FIGS. 1B and 1C depict conceptual diagrams illustrating head 12 of patient as viewed from left lateral side of the patient and viewed from the right lateral side of the patient, respectively. As depicted in FIG. 1B, LAQ and LPQ together extend from an anterior side of head 12 of patient to a posterior side of head 12 of patient to define a generally diagonal bottom interface that extends from a forehead of the patient to a location near the neck of the patient. Similarly, as depicted in FIG. 1C, RAQ and RPQ together extend from an anterior side of head 12 of patient to a posterior side of head 12. In this way, LAQ, LPQ, RAQ, and RPQ may generally cover scalp 16 of patient. Although four quadrants are described herein, Fewer or more sections may be used to describe various locations of scalp 16 for the appropriate placement of recharge coils of the recharging device.

Figure 1D:
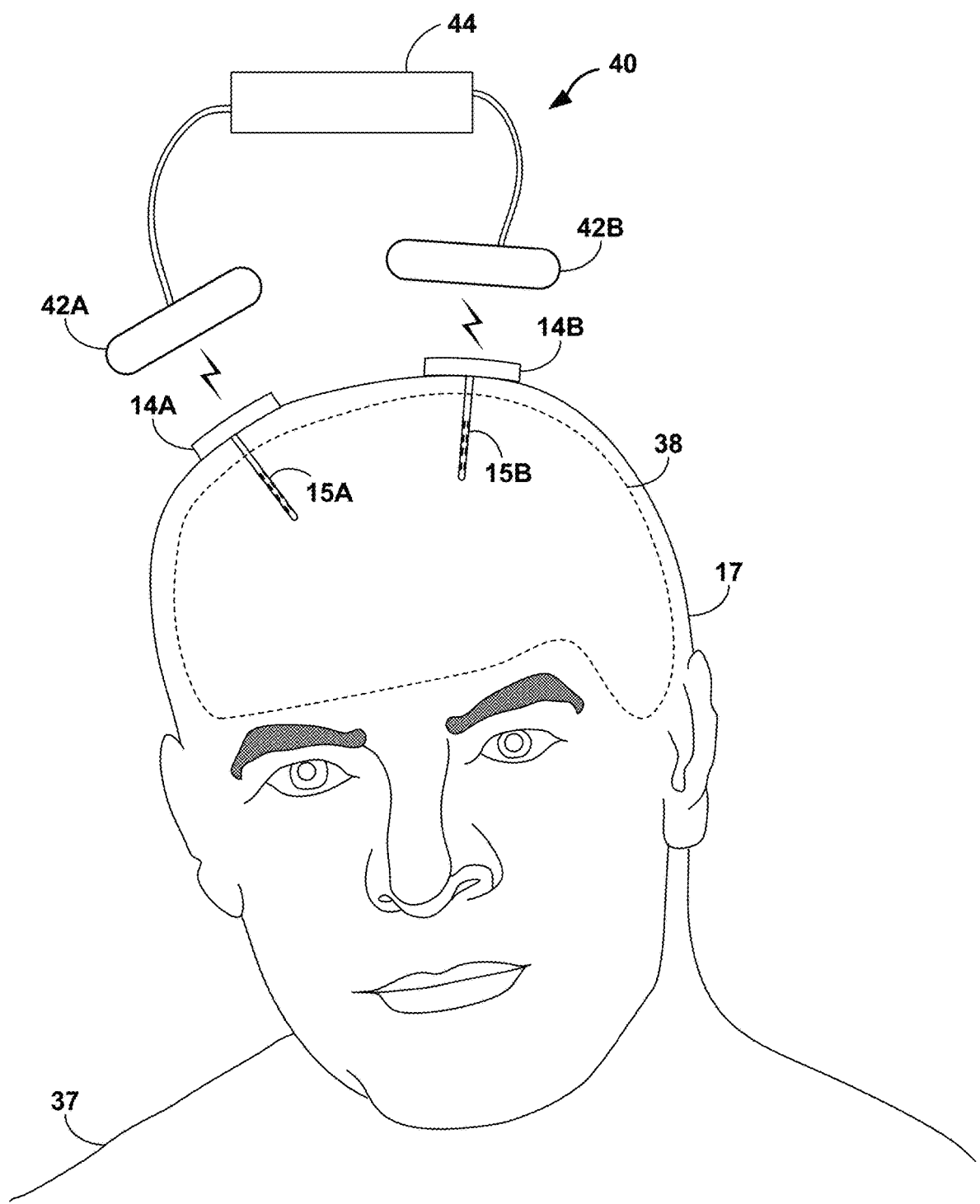
FIG. 1D is a conceptual diagram illustrating an example patient with two IMDs disposed on a cranium of a patient and a recharging device configured to recharge the power sources of the IMDs.

FIG. 1D is a conceptual diagram illustrating an example patient with two IMDs 14A and 14B (hereinafter "IMDs 14") disposed on a cranium of a patient and a recharging device 40 configured to recharge the power sources of the IMDs 14. IMDs 14 may be coupled to respective electrical stimulation leads 15A and 15B, which dispose respective electrodes within brain 38 of patient 37. Leads 15A and 15B may, for example, be implanted to treat the right and left hemispheres of patient 37. In other examples, three or more IMDs may be implanted in the cranium 17 of patient 37.

In the example of FIG. 1D, recharging device 40 includes power unit 44 coupled to recharge coils 42A and 42B via respective cables. Each of recharge coils 42A and 42B may be configured to provide charging power to respective IMDs 14A and 14B. For example, recharge coil 42A may be able to provide charging power concurrently with or independently of recharge coil 42B, and vice versa. In some examples, recharge coil 42A may provide a first amount of power to IMD 14A simultaneously with recharge coil 42B providing a second amount of power to IMD 14B, while the first amount of power is different than the second amount of power as a result of different parameters of respective IMDs 14 (e.g., parameters being a power level of a power source of the respective IMD 14 or a temperature of the IMD 14 as a result of the received power or the like).

As discussed herein, recharging device 40 may be recharge power sources of both IMDs 14 more efficiently when recharging coils 42A, 42B of recharging device 40 are physically aligned with IMDs 14. For example, recharging device 40 may provide more power per second to IMDs 14 when respective recharge coils 42A, 42B are aligned with recharge coils housed within or otherwise secured to respective IMDs 14. Given that recharging device 40 is configured to provide power to both IMDs simultaneously, it may be advantageous to thusly align both recharging coils simultaneously. Similarly, as discussed herein, given the relatively frequent (e.g., once a day) and prolonged (e.g., up to an hour) nature of charging, it may be advantageous for recharging device 40 to be fixedly securable to a wearable medical device that is configured to reliably align recharge coils 42A, 42B with respective recharge coils of each IMD 14 when the wearable medical device is worn (e.g., secured to patient 36).

Figure 2:
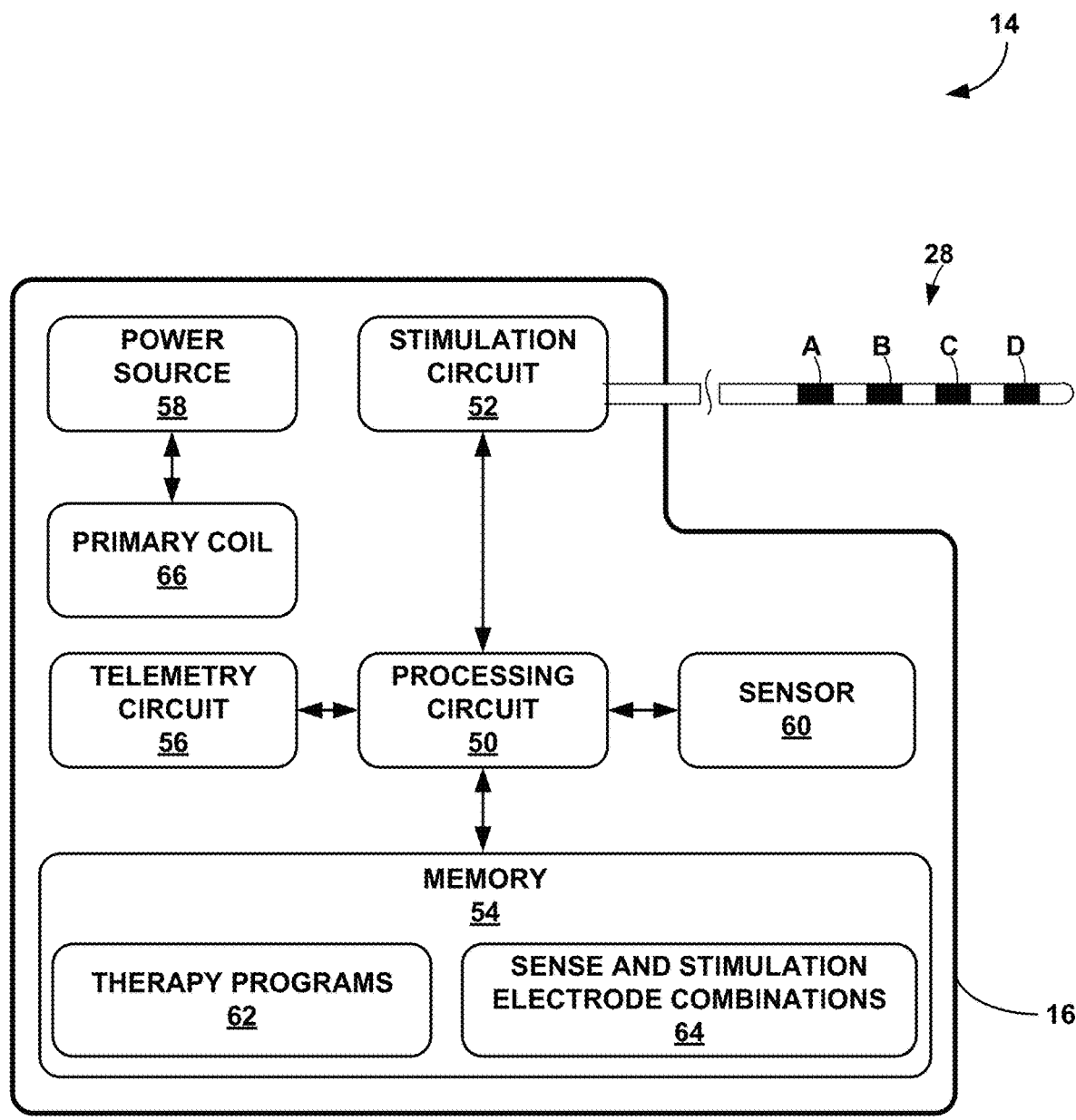
FIG. 2 is a block diagram illustrating example components of the IMD of FIG. 1A.

FIG. 2 is a block diagram illustrating example components of IMD 14. In the example of FIG. 2, IMD 14 includes processing circuitry 50, stimulation circuitry 52, memory 54, telemetry circuitry 56, power source 58, sensor 60, and secondary coil 66. In other examples, IMD 14 may include a greater or fewer number of components. For one example, in some instances IMD 14 may not include sensor 60. While in FIG. 2 most components of IMD 14 are depicted as contained within in a single substantially contiguous compartment of housing 16, in other examples components of IMD 14 may be contained within IMD 14 in other configurations. For example, in some instances components of IMD may be contained within a plurality of housings of IMD 14, or some components may be secured partially or fully outside of an internal hermetically sealed compartment of housing 16 and electrically coupled to other components within a compartment of housing 16 as described herein.

In general, IMD 14 may comprise any suitable arrangement of hardware, alone or in combination with software and/or firmware, to perform the various techniques described herein attributed to IMD 14 and processing circuitry 50. In various examples, processing circuitry 50 of IMD 14 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include memory 54, such as random-access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Memory 54 may store therapy programs 62, sense or stimulation electrode combinations 64, or other instructions that specify therapy parameter values for the therapy provided by stimulation circuitry 52 and IMD 14. Moreover, although processing circuitry 50, stimulation circuitry 52, and telemetry circuitry 56 are described as separate portions of circuitry, in some examples processing circuitry 50, stimulation circuitry 52, and/or telemetry circuitry 56 may be fully or partially integrated with each other. In some examples, processing circuitry 50, stimulation circuitry 52, and/or telemetry circuitry 56 correspond to individual hardware units, such as ASICs, DSPs, FPGAs, or other hardware units.

Stimulation circuitry 52 may generate and deliver electrical stimulation under the control of processing circuitry 50. In some examples, processing circuitry 50 controls stimulation circuitry 52 by accessing memory 54 to selectively access and load at least one therapy programs 62 to stimulation circuitry 52. For example, in operation, processing circuitry 50 may access memory 54 to load one therapy programs 62 to stimulation circuitry 52. In such examples, relevant stimulation parameters may include a voltage amplitude, a current amplitude, a pulse rate, a pulse width, a duty cycle, or the combination of electrodes 28A, 28B, 28C, and 28D as stored in stimulation electrode combinations 64 that stimulation circuitry 52 uses to deliver the electrical stimulation signal. Although stimulation circuitry 52 may be configured to generate and deliver electrical stimulation therapy via one or more of electrodes 28A, 28B, 28C, and 28D of lead 28, stimulation circuitry 52 may be configured to provide different therapy to patient. For example, stimulation circuitry 52 may be configured to deliver drug delivery therapy via a catheter. These and other therapies may be provided by IMD 14.

Power source 58 may be rechargeable through the use of secondary coil 66. Secondary coil 66, which may be a coil of wire or other device capable of inductive coupling with a primary coil disposed external to the patient, such as a coil secured to a wearable medical device and mounted to head 12 of patient as described herein. Secondary coil 66 may include a winding of wire configured such that an electrical current can be induced within the wire when subjected to (e.g., physically exposed to) an electromagnetic field from an external primary coil. The induced electrical current may then be used to recharge power source 58. In this manner, the electrical current may be induced in secondary coil 66 associated with power source 58. The induction may be caused by electrical current generated in the primary coil of an external charging device and based on the selected power level. The coupling between secondary coil 66 and the external primary coil may be dependent upon the alignment of the two coils. In some examples, the coupling efficiency increases when the two coils share a common axis and are in close proximity to each other. The external charging device and/or IMD 14 may provide one or more audible tones, visual indications, haptic feedback, or the like that indicates an assessment of the alignment (e.g., providing more/less/different audible tones/visual indications/haptic feedback in response to an improving or diminishing alignment).

Although inductive coupling is generally described as the method for recharging rechargeable power source 58, other wireless energy transfer techniques may alternatively be used. Any of these techniques may generate heat in IMD 14 such that the charging process can be controlled using the calculated cumulative thermal dose as feedback.

IMD 14 may include one or more circuits that filter and/or transform the electrical signal induced in secondary coil 66 to an electrical signal capable of recharging power source 58. For example, in alternating current induction, IMD 14 may include a half-wave rectifier circuit and/or a full-wave rectifier circuit configured to convert alternating current from the induction to a direct current for power source 58. The full-wave rectifier circuit may be more efficient at converting the induced energy for power source 58. However, a half-wave rectifier circuit may be used to store energy in power source 58 at a slower rate. In some examples, IMD 14 may include both a full-wave rectifier circuit and a half-wave rectifier circuit such that IMD 14 may switch between each circuit to control the charging rate of power source 58 and temperature of IMD 14.

In some examples, IMD 14 may include a measurement circuit configured to measure the current and/or voltage induced during inductive coupling. This measurement may be used to measure or calculate the power transmitted to IMD 14 from an external charging device. In some examples, the transmitted power may be used to approximate the temperature of IMD 14 and that of the surrounding tissue. This method may be used to indirectly measure the temperature of tissue in contact with the housing of IMD 14. In other examples, IMD 14 may estimate the transmitted power using the measured voltage or current.

Power source 58 may include one or more capacitors, batteries, or other energy storage devices. Power source 58 may then deliver operating power to the components of IMD 14. In some examples, power source 58 may include a power generation circuit to produce the operating power. Power source 58 may be configured to operate through hundreds or thousands of discharge and recharge cycles. Power source 58 may also be configured to provide operational power to IMD 14 during the recharge process. In some examples, power source 58 may be constructed with materials to reduce the amount of heat generated during charging. In other examples, IMD 14 may be constructed of materials that may help dissipate generated heat at power source 58 and/or secondary coil 66 over a larger surface area of the housing of IMD 14.

IMD 14 include one or more sensors 60. Sensor 60 may include one or more sensing elements that sense values of a respective patient or IMD 14 parameter. For example, sensor 60 may include one or more accelerometers, optical sensors, chemical sensors, temperature sensors, pressure sensors, or any other types of sensors. IMD 14 may include additional sensors within the housing of IMD 14 and/or coupled via one of leads 28 or other leads. For example, IMD 14 may receive sensor signals wirelessly from remote sensors via telemetry circuitry 56. In some examples, one or more of these remote sensors may be external to patient (e.g., carried on the external surface of the skin, attached to clothing, or otherwise positioned external to the patient). Sensor 60 may output patient or IMD parameter values that may be used as feedback to control delivery of therapy or to otherwise manage IMD.

For example, sensor 60 may be a temperature sensor that sensing temperatures during recharging. As a temperature sensor, sensor 60 may include one or more temperature sensors (e.g., thermocouples or thermistors) configured to measure the temperature of IMD 14. As described herein, temperature sensor 60 may be used to directly measure the temperature of IMD 14 and/or tissue surrounding and/or contacting the housing of IMD 14. Processing circuitry 50 (or an external charging device) may use this temperature measurement as the tissue temperature feedback to determine the cumulative thermal dose provided to tissue during charging of power source 58. Although a single temperature sensor may be adequate, multiple temperature sensors may provide a better temperature gradient or average temperature of IMD 14. The various temperatures of IMD 14 may also be modeled and provided to determine the cumulative thermal dose. Although processing circuitry 50 may continually measure temperature using sensor 60, processing circuitry 50 may conserve energy by only measuring temperature during recharge sessions. Further, temperature may be sampled at a rate necessary to calculate the cumulative thermal dose, but the sampling rate may be reduced to conserve power as appropriate.

Processing circuitry 50 may also control the exchange of information with a charging device mounted to head 12 of patient and/or an external programmer using telemetry circuitry 56. Telemetry circuitry 56 may be configured for wireless communication using radio frequency protocols or inductive communication protocols. Telemetry circuitry 56 may include one or more antennas configured to communicate with the programmer, for example. Processing circuitry 50 may transmit operational information and receive therapy programs 62 or therapy parameter adjustments via telemetry circuitry 56. Also, in some examples, IMD 14 may communicate with other implanted devices, such as stimulators, control devices, or sensors, via telemetry circuitry 56. In addition, telemetry circuitry 56 may be configured to transmit the measured values from sensor 60. In other examples, processing circuitry 50 may transmit additional information to an external charging device related to the operation of power source 58. For example, processing circuitry 50 may use telemetry circuitry 56 to transmit indications that power source 58 is completely charged, power source 58 is fully discharged, or any other charge status of power source 58. Processing circuitry 50 may also transmit information to the external charging device that indicates any problems or errors with power source 58 that may prevent power source 58 from providing operational power to the components of IMD 14.

Examples of local wireless communication techniques that may be employed to facilitate communication between an external device and IMD 14 include RF communication according to the 802.11 or Bluetooth specification sets or other standard or proprietary telemetry protocols. In this manner, other external devices may be capable of communicating with an external charging device without needing to establish a secure wireless connection. As described herein, telemetry circuitry 56 may be configured to receive a measured tissue temperature from IMD 14. The tissue temperature may be measured adjacent to rechargeable power source 58, such as near the housing of IMD 14 or external of the housing. Although IMD 14 may measure the tissue temperature, one or more different implantable temperature sensors (e.g., standalone implantable temperature sensing devices) may independently measure the tissue temperature at different positions and transmit the temperature to an external charging device. In some examples, multiple temperature readings by IMD 14 may be averaged or otherwise used to produce a single temperature value that is transmitted to an external charging device. The temperature may be sampled and/or transmitted at different rates, e.g., on the order of microseconds, milliseconds, seconds, minutes, or even hours. Processing circuitry 50 may then use the received tissue temperature to calculate the cumulative thermal dose. Processing circuitry 50 may transmit feedback information to an external charging device (e.g., charging device 40) regarding the alignment of external primary coil to secondary coil 66. This alignment information may be used by charging device 40 or other device to provide feedback to the user when determining the location on the wearable medical device to position the external charging coil (e.g., the primary coil). Therefore, in some examples, IMD 14 may provide data that aids in the determination of the location at which the charging coil should be located with respect to the scalp of the patient. While the wearable medical device is located on the scalp of the patient, the location of the external recharging coils with respect to the wearable medical device may be determined for attachment of the recharging coils at the respective locations.

Aspects of the disclosure relate to wearable medical devices that are configured to secure a recharging device (e.g., one or more recharging coils) to a plurality of locations relative to scalp 16 of patient. Configuring the wearable medical device to secure recharging coils at a plurality of locations may improve an ability of the patient to repeatedly align the recharging coils of the recharging device with secondary coil 66 of IMD 14. In this manner, for each recharge session, the wearable medical device may enable consistent locating of the recharge coils and relatively high efficiency with which the recharging device may recharge power source 58 of IMD 14.

Further, as discussed herein, the wearable medical device may be removably securable to a predetermined location on head 12 of the patient, such that when secured the recharge coils of the recharge device may be reliably located at respective predetermined locations relative to scalp 16 of the patient. In some examples, the wearable medical device may be configured such that it secures to head 12 substantially only at the predetermined location in the predetermined manner (e.g., such that it is difficult, impossible, and/or uncomfortable to secure the wearable medical device to head 12 at a location other than the predetermined location). Further, the wearable medical device may be relatively easy to secure to head 12 of patient, such that it may require only a single hand and a minimum amount of motion to secure the wearable medical device to head 12. Further, while secured, the wearable medical device may be relatively stable on head 12 of patient, such that wearable medical device may be configured to avoid being unintentionally unsecured from head 12. The wearable medical device may be configured to stay secured to head 12 for a substantially indefinite period of time until a specific removal force is applied to the wearable medical device to remove the wearable medical device from head 12. The wearable medical device may be configured to be relatively comfortable as secured to head 12. In some examples, the wearable medical device may include one or more adjustment mechanisms that are configured to adjust a fit of the wearable medical device to specifically fit head 12 of patient.

Depending upon a shape of the wearable medical device, the recharging device may utilize different sets of coils. FIGS. 3A-D illustrate conceptual forms of example recharging coil components that can be held by example wearable medical devices disclosed herein. Coil components may be formed by wound wire or a printed circuit board (PCB) type metal trace adhered to either a rigid or a flexible substrate, such as Kapton. Coil component may be part of a charge module that also includes recharge circuitry (e.g. as depicted in FIG. 5). The recharging coils of FIGS. 3A-3D may be employed, for example, by wearable medical devices described herein, such as wearable medical devices of FIGS. 4A, 4C, 5-6C, 8A, 8B, and 10A-34C FIG. 3A depicts a conceptual diagram illustrating a variety of shapes for relatively compact recharging coil components 80A-80F (collectively, "coil components 80"), which may be employed by wearable medical devices discussed and depicted herein. Coil components 80 may either be relatively rigid or relatively flexible, and may either be relatively flat or have a pre-formed curvature.

Figure 3A:
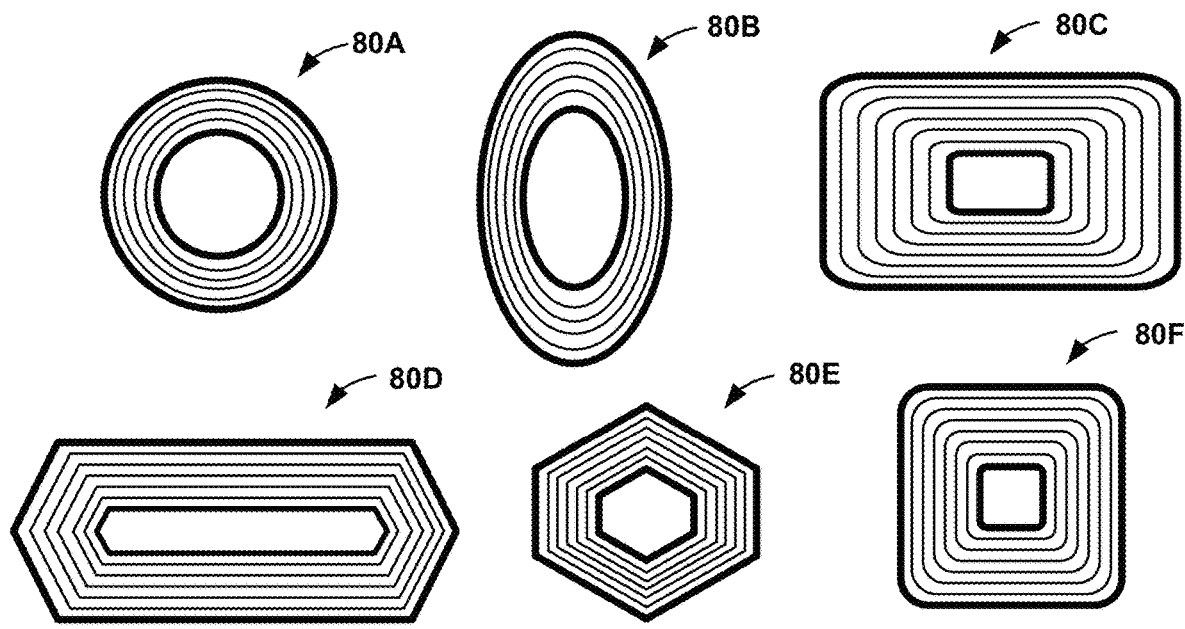
FIGS. 3A, 3B, 3C, and 3D are conceptual diagrams illustrating example recharge coils that may be used to recharge the IMD of FIG. 1A
Figure 3B:
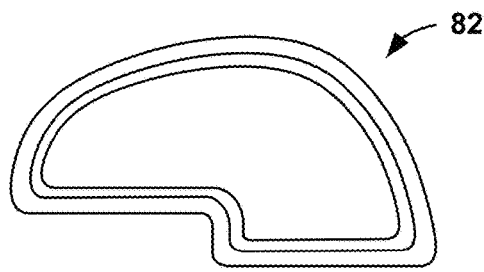
Figures 3C, 3D:
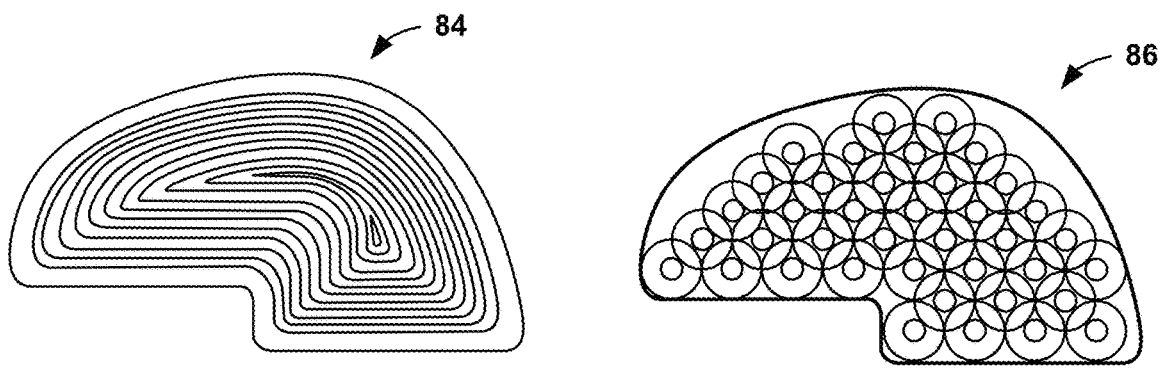

FIGS. 3B-3D depict a conceptual diagram illustrating example shapes for three more types of coil components 82, 84, 86, respectively, which may be employed by wearable medical devices discussed and depicted herein. With reference to FIG. 3B, component 82 has a recharging coil extending just around a perimeter of the substrate. With reference to FIG. 3C, component 84 has either a single recharging coil extending around the perimeter of the substrate and in concentric turns within the perimeter, or has multiple concentric recharging coils. In examples of component 84 with multiple recharging coils, the coils may be individually turned on. With reference to FIG. 3D, component 86 has multiple, relatively smaller, coils distributed across the substrate, wherein the coils may be individually turned on or turned on in groups. Each of coil components 82, 84, 86 may either be relatively rigid or relatively flexible, and may either be relatively flat or have a pre-formed curvature.

Figure 4A:
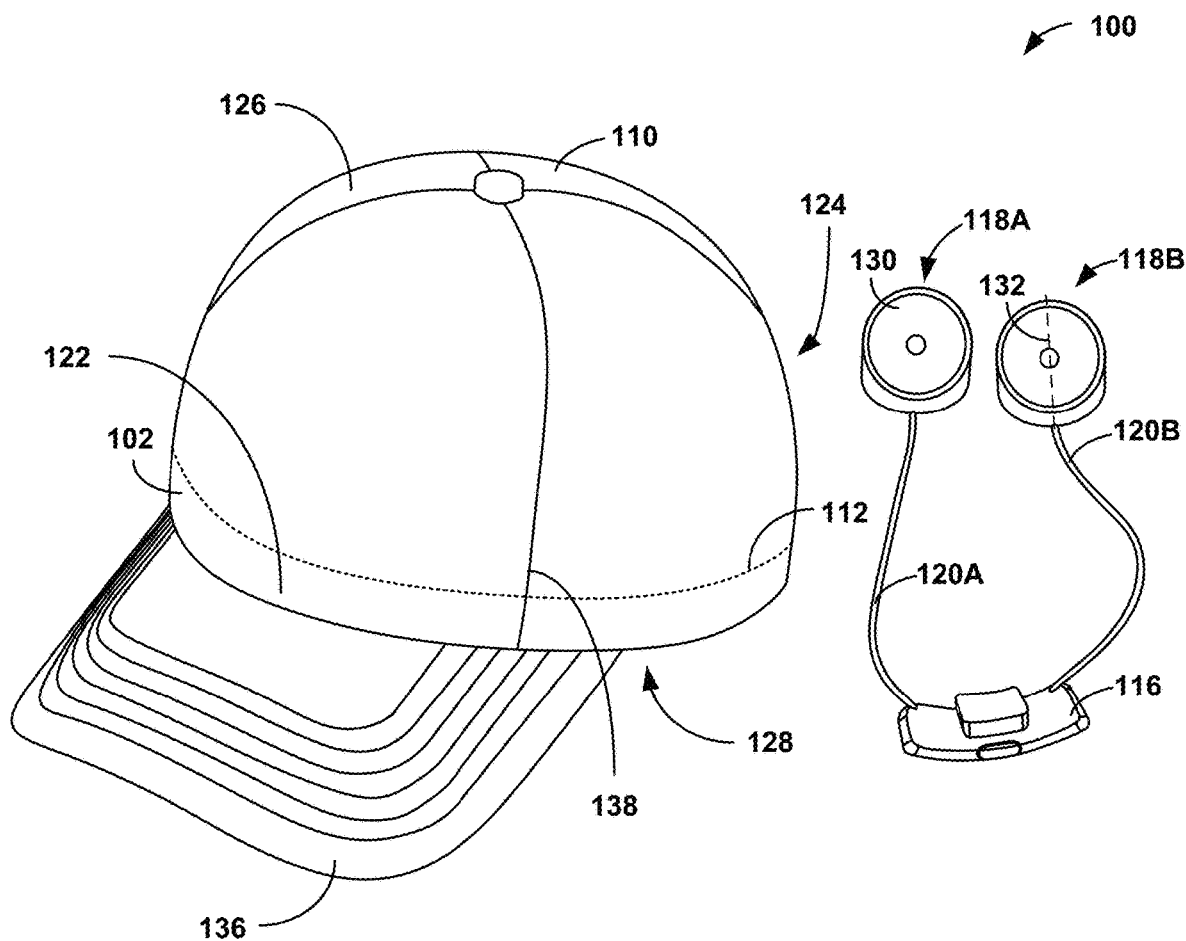
FIG. 4A is a conceptual diagram illustrating a first example wearable medical device and recharging device that may be used to recharge a power source of the IMD of FIG. 1A.
Figure 4B:
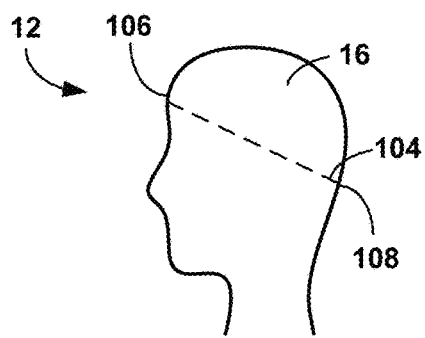
FIG. 4B is a side view of a head to which the wearable medical device of FIG. 4A may be mounted.
Figure 5:
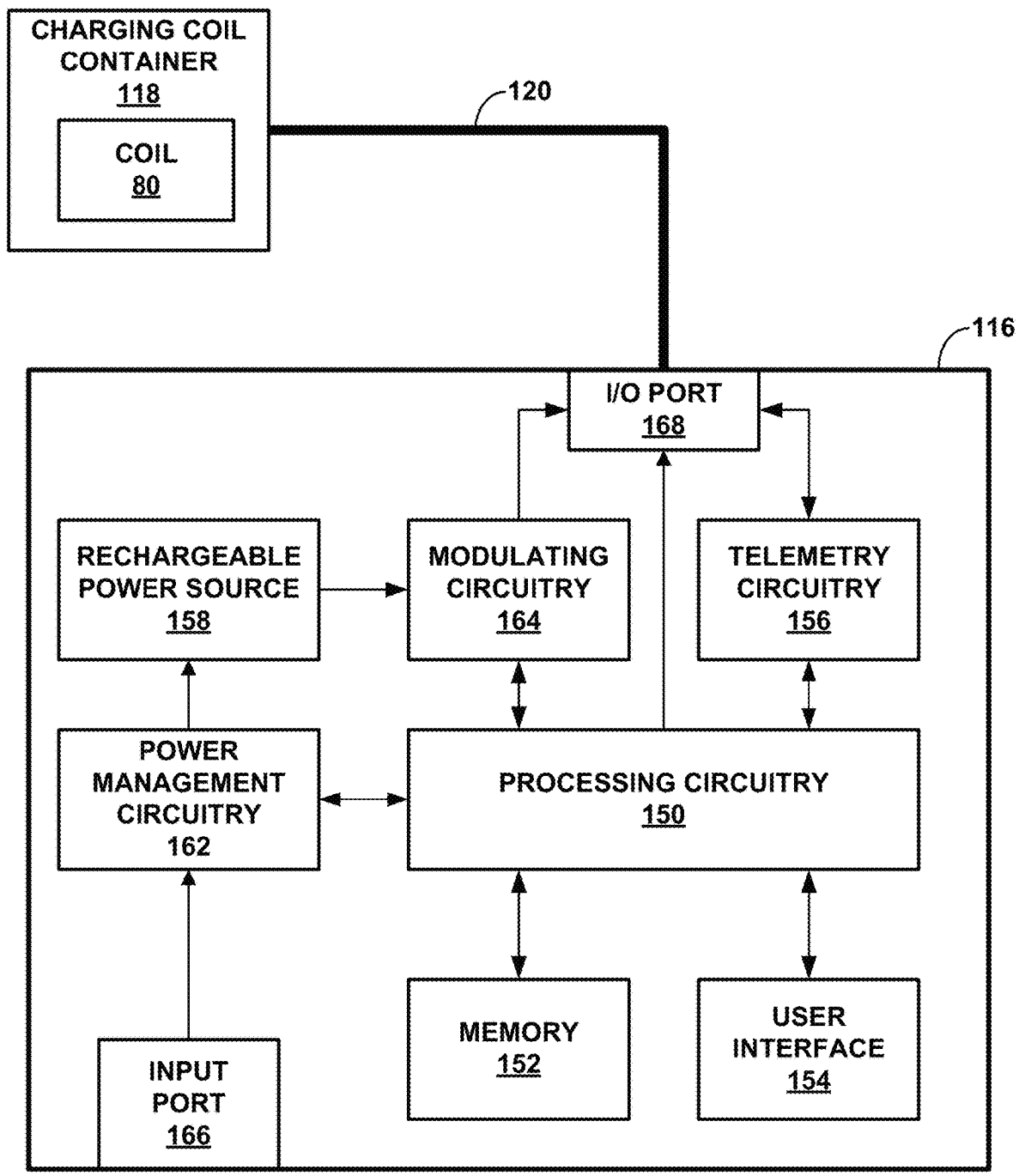
FIG. 5 is a block diagram illustrating example components of power unit and charging coil container of the recharging device of FIG. 4A.

FIG. 4A depicts a conceptual diagram illustrating an unassembled view of recharging system 100, which may include wearable medical device 101 and recharging device 103, to be secured to head 12 of a patient. Wearable medical device 101 may include securing member 102 that is configured to extend around at least a portion of circumference of scalp 16 to secure wearable medical device 101, and recharging device 103 when attached, to head 12. Securing member 102 may be a band that is configured to extend substantially fully around an outer perimeter of scalp 16 along one relatively flat plane. For example, looking to FIG. 4B which depicts a conceptual diagram illustrating a side view of head 12 of a patient, securing member 102 may be secured to head 12 along relatively flat plane 104 that extends from forehead 106 of head 12 to anterior middle 108 of the back of head 12. In some examples, securing member 102 may be configured to secure to head 12 substantially only along plane 104, such that it may be difficult or impossible or otherwise uncomfortable for securing member 102 to be secured to head 12 along a plane other than plane 104. However, plane 104 upon which securing member 102 is secured to head 12 may be modifiable, such that recharging device 100 may be configured in different ways to identify or select different plane 104.

In some examples, securing member 102 may be relatively inelastic, or stiff, such that securing member 102 may be configured to maintain a general shape in response to normal operating forces. For example, securing member 102 may be configured to define a relatively circular shape that generally matches the cross-sectional shape of scalp 16 along plane 104 upon which securing member 102 is secured to head 12. Securing member 102 may be configured to define a circumference that is slightly smaller than the circumference of scalp 16 along plane 104, such that securing member 102 stretches slightly (e.g., stretches an amount equal to the differences in cross-section) to fit on head 12. In some examples, securing member 102 may secure wearable medical device 101 to head 12 as a result of this interference fit between head 12 and securing member 102. The securing member 102 may have a cross-sectional shape of an oval, rectangle, rounded rectangle, or any other shape that promotes securing wearable medical device 101 to head 12. A relative inelastic material of securing member 102 may include polyethylene, high-density polyethylene, nylon, or the like.

In other examples, securing member 102 may be relatively flexible, such that securing member 102 does not substantially hold a predetermined shape. In such examples, securing member 102 may define a relatively smaller circumferential length of diameter and/or be made of a relatively material that stretches more than in examples where securing member 102 is relatively inelastic, or stiff. A relatively more flexible securing member 102 may be secured to head 12 as a result of relatively smaller circumference and a more elastic construction in comparison to a relatively stiff securing member 102. As such, securing member 102 may be configured to be secured to head 12 as a result of an interference fit relationship between a relative stiffness, a relative circumference, and a relative elasticity of securing member 102.

Securing member 102 may be made of an elastic material that is configured to stretch to match the contours of skull 23 as securing member 102 as secured to head. For example, securing member 102 may be made of a fabric such as a micro-polyester and/or spandex material, or materials such as poly propylene, polyethylene, silicone, polycarbonate, acrylic, acrylonitrile butadiene styrene, polystyrene, styrene acrylonitrile, whether alone or in a combination with each other, or other similar materials. In some examples securing member 102 may extend to an outer surface of wearable medical device 101. In other examples, securing member 102 may be an internal component, such that securing member 102 is enclosed within a pocket of flexible body 110.

Flexible body 110 may be a component of recharging device 100. Flexible body 104 may be a relatively flexible stitched or woven fabric or sheet. Flexible body 104 may be fixedly secured to securing member 102, such that it may be difficult to remove flexible body 104 from securing member 102 without damaging one or both of flexible body 110 and securing member 102. For example, securing member 102 may be disposed within a pocket created by folding over and stitching a portion of flexible body 110 to itself, or securing member 102 may be stitched or bonded or otherwise directly connected to flexible body 110.

Flexible body 110 may be configured to extend radially in from top edge 112 of securing member 102, where top edge 112 is an edge of securing member 102 that extends around perimeter of securing member 102. As secured to head 12, top edge 112 may be portion of securing member 102 that is furthest from a face of head 12 (e.g., such that top edge 112 is near a "top" of head 12 of a patient as secured to head 12). Flexible body 110 may be configured to conform to contour of at least some of each of the left anterior quadrant, the left posterior quadrant, the right posterior quadrant, and the right anterior quadrant of scalp 16 of the patient when securing member 102 is stably mounted to head 12. For example, securing member 102 may be configured to be secured to an outer boundary of scalp 16 as scalp 16 extends around head 12, and flexible body 110 may be configured to substantially cover most or all of scalp 16 as flexible body 110 extends radially in from the stably mounted securing member 102.

Recharging device 103 of recharging system 100 may include power source compartment 116 (e.g., a power unit that contains electrical components such as a power source, processing circuitry, and/or other functional components). Recharging device 103 may be similar to recharging device 40 of FIG. 1D. Power source compartment 116 may be coupled to one or more recharge coil containers 118A, 118B (collectively, "recharge coil containers 118") that may each contain a respective recharge coil 80, 82, 84, 86, where recharging device 103 includes the power source compartment 116, recharge coil containers 118, and respective recharge coils 80, 82, 84, 86. Recharge coil containers 118 may be similar to recharge coils 42A and 42B of FIG. 1D, and power source compartment 116 may be similar to power unit 42 of FIG. 1D. Power source compartment 116 may be coupled to recharge coils 80, 82, 84, 86 housed within recharge coil containers 118 through one or more cables 120A, 120B (collectively, "cables 120"). Power source compartment 116 may include a power source and may be configured to provide current to recharge coils of recharge coil containers 118 so that these recharge coils may create an electromagnetic field from which a secondary coil of a respective charging module of an implanted cranially-mounted medical device (e.g., secondary coil 66 of IMD 14 from FIG. 2) may draw current to recharge a power supply (e.g., power source 56) of the implanted medical device.

Power source compartment 116 may be configured to be secured to the wearable medical system 101. Power source compartment 116 may be configured to be secured in a stable but temporary manner, such that power source compartment 116 may be attached and removed to the wearable medical system 101 numerous times. In some examples, wearable medical device 101 may define front side 122 and back side 124 that are on opposite sides of wearable medical device 101, where front side 122 is configured to be secured to head 122 such that front side 122 is aligned with anterior of head 12, and back side 124 is configured to be aligned with posterior of head 12. In such examples, power source compartment 116 may be configured to be clipped or otherwise attached to securing mechanism 102 at back end 124 of wearable medical device 101.

In some examples, cables 120 may be substantially permanently coupled between power source compartment 116 and one or more recharge coil containers 118, such that it may be difficult or impossible to remove cables 120 from power source compartment 116 and/or recharge coil containers 118 without damaging cables 120, power source compartment 116, and/or recharge coil containers 118. In other examples, cables 120 may be configured to be inserted into power source compartment 116 and/or recharge coil containers 118 to couple power source compartment 116 to recharge coil containers 118. For example, cables 120 may utilize micro universal serial bus (USB) formats to plug into one or both of power source compartment 116 and recharge coil containers 118.

Recharge coil containers 118 may include a housing that encapsulates coil components such as coil component 80A of FIG. 3A. Recharge coil containers 118 may be configured to be secured to flexible body 110. Recharge coil containers 118 may be configured to be secured to a main surface of flexible body 110 such that recharge coil containers 118 contact scalp 16. For example, flexible body 110 may define first main surface 126 on an external face of recharging device 100 and second main surface 128 on an opposite side of first main surface, wherein second main surface 128 is configured to contact scalp 16 once securing member 102 is secured to head 12. In this example, recharge coil containers 118 may be configured to be secured to second main surface 128 of flexible body 110.

Figure 4C:
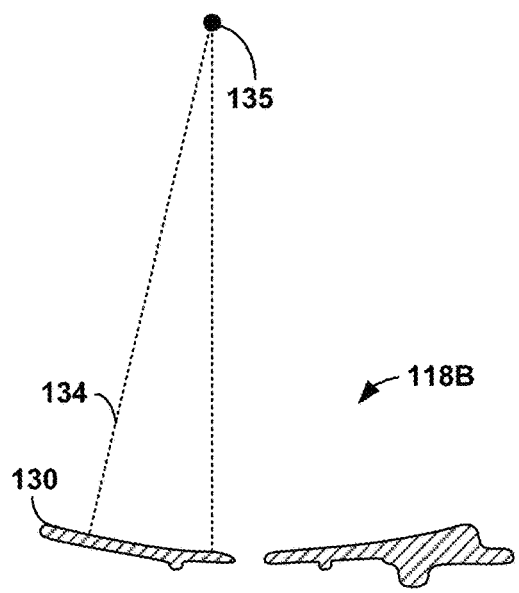
FIG. 4C is a cross-sectional view of an example recharge coil container of the recharging device of FIG. 4A.

Recharge coil containers 118 may define main surface 130 that is configured to contact scalp 16 as secured to second main surface 128 of flexible body 110. Main surface 130 of recharge coil containers 118 may define a curvature that approximates a curvature of scalp 16. For example, FIG. 4C depicts a conceptual diagram illustrating a cross sectional view of recharge coil container 118B as taken along plane 132 shown in FIG. 4A. As depicted in FIG. 4C, main surface 130 of recharge coil container 118B defines curvature that with radius 134 to a center point 135 that is generally at a center point of head 12 of the patient. In this way, radius 134 of a curvature of main surface 130 may be substantially similar to curvature of scalp 16 of patient. In some examples, main surface 130 may define a changing radius 134 across different portions of main surface 130 to better approximate a curvature of scalp 16 of patient (e.g., since head 12 of patient are not perfectly spherical). Configuring recharge coil containers 118 to define main surface 130 that contacts scalp 16 and approximates curvature of scalp 16 may improve comfort and/or alignment of the recharge coils and wearable medical device 100 when recharge coil containers 118 are disposed against scalp 16.'

In some examples, wearable medical device 101 may include bill 136 configured to extend out from front 122 of securing member 102 and flexible body 110. For example, when wearable medical device 101 is secured to head 12 of a patient, bill 136 may be configured to extend out over forehead 106 of patient and/or shade eyes of the patient (e.g., from the sun, when recharging device 100 is worn outside). Bill 136 may be made of a relatively stiff material such as a polymer such as high-density polyethylene or the like, such that bill 136 maintains its shape and the shape of flexible body 110 when maneuvering wearable medical device 101 to head 12 in order to locate recharge coil containers 118 to the one or more predetermined locations. Bill 136 may include a relatively compliant, or soft, material (e.g., such as a micro-polyester spandex material) covering the relatively stiff material to increase a comfort of bill 136 and wearable medical device 101 as wearable medical device 101 is secured to head 12. In some examples, bill 136 may be configured to be bendable into a static "U" shape as bill 136 extends away from securing member 102 and flexible body 110. In other examples, bill 136 may additionally or alternatively be configured to define a relatively flat plate as bill 136 extends away from securing member 102 and flexible body 110. An amount that bill 136 extends away from securing member 102 and flexible body 110 is depicted for purposes of illustration only, as bill 136 may extend different lengths in different examples. In some examples, an amount of quality of material of bill 136 may provide a counterweight to power source compartment 116 when power source compartment 116 is secured to posterior 124 of wearable medical device 101.

In some example, flexible body 110 may include a plurality of seams 138 that extend at least from securing member 102 to a central spot in flexible body 110. Seams 138 may provide structural support, e.g., a stiffness, to flexible body 110. As a result of seams 138 providing a stiffness to flexible body 110, wearable medical device 101 may improve an ability of recharge coil containers 118 to be aligned with recharge coils of devices 14 implanted on head 12 of patient, therein improving an efficiency with which wearable medical device 101 and recharging device 103 may recharge power sources of devices 14 implanted on head 12 of the patient. Seams 138 may divide flexible body 110 into four relatively equal quadrants, though in other examples seams 138 may divide flexible body 110 into more (e.g., six) or less (e.g., two) subsections.

In some examples, power source compartment 116 may include a functional electrical recharging control unit to control the electrical current to the recharging coils of charging coil container 118. For example, power source compartment 116 may include circuitry, coils, memory, or the like in order to provide functionality of recharging device 103. For example, FIG. 5 is a block diagram of components of recharging device 103, which may include power source compartment 116 coupled to recharge coil container 118.

Though FIG. 5 is depicted with coil 80 housed within charging coil container 118 for purposes of clarity, it is to be understood that coil 82, 84, 86 or other types of coils may be housed within charging coil container 118 in other examples. Power source compartment 116 of FIG. 5 may include a housing that houses processing circuitry 150 that controls delivery of energy from rechargeable power source 158 by sending control signals to components such as power management circuitry 162 and modulating circuitry 164. Each of these components, or circuitry, may include electrical circuitry that is configured to perform some or all of the functionality described herein. As shown, power source compartment 116 may include any suitable arrangement of hardware, alone or in combination with software and/or firmware, to perform the techniques attributed to recharging device 101. Processing circuitry 150 may include one or more processors, such as one or more microprocessors, DSPs, ASICs, FPGAs, or any other equivalent integrated or discrete logic circuitry, as well as any combinations of such components. For example, processing circuitry 150 may include one or more processors configured to perform the processes discussed with respect to telemetry circuitry 156.

Power management circuitry 162 recharges rechargeable power source 158 using an AC voltage received from an input port 166 of power source compartment 116. Modulating circuitry 164 converts DC voltage provided by power source 158 into an AC voltage at a desired amplitude and frequency for delivery to charging coil 80 via cable 120, which may be coupled to charging coil container 118 and therein coil 80 via an input/output port 168. Although only a single coil 80 is shown as coupled to power source compartment 116 via cable 120, two or more coils may be coupled to I/O port 168 of power source compartment 116 via the same or different respective cables 120.

The example of FIG. 5 further illustrates power source compartment 116 including a telemetry circuitry 156. Telemetry circuitry 156 may support wireless communication between IMD 14 and recharging device 100 under the control of processing circuitry 150. Telemetry circuitry 156 may also be configured to communicate with another computing device via wireless communication techniques, or direct communication through a wired connection. In some examples, telemetry circuitry 156 may provide wireless communication via coil 80 and/or via another coil and/or other dedicated telemetry antenna (e.g., via radio frequency telemetry). For example, telemetry circuitry 156 may receive a signal from one or more IMDs 14 that indicates that a temperature of a respective IMD 14 exceeds a threshold as a result of an induced current, and in response to which recharging device 103 may reduce the power of the electromagnetic field for the respective IMD 14 to reduce current inducted in IMD 14. Processing circuitry 150 may receive recharge status information via telemetry and present the information to the patient via user interface 154, which may include a display, one or more buttons or dials, and/or one or more speakers. Processing circuitry 150 may also be configured to receive user input via user interface 154.

Memory 152 may store information received via telemetry and may also store program instructions to be executed by processing circuitry 150. Memory 152 may include RAM, ROM, PROM, EPROM, EEPROM, flash memory, a hard disk, a CD-ROM, or the like. Further, memory 152 may store executable instructions that, when executed by processing circuitry 150, cause processing circuitry 150 and recharging device 100 to provide the functionality ascribed to recharging device 100 throughout this disclosure. For example, memory 152 may include instructions that cause processing circuitry 150 to send current to coils 80 of one or more recharge coil containers 118 in response to a received user input.

Although processing circuitry 150, telemetry circuitry 156, power management circuitry 162, and modulating circuitry 164 are described as separate circuits, in some examples, processing circuitry 150, telemetry circuitry 156, power management circuitry 162, and/or modulating circuitry 164 may be functionally integrated. In some examples, processing circuitry 150, telemetry circuitry 156, power management circuitry 162, and/or modulating circuitry 164 may correspond to individual hardware units, such as ASICs, DSPs, FPGAs, or other hardware units.

FIGS. 6A-6C depict conceptual diagrams of recharge coil container 118B and attachment assembly in an exploded perspective view, an exploded cross-sectional view, and an assembled cross-sectional view, respectively. Cross sectional views of FIGS. 6B and 6C are taken along cut plane 171 of FIG. 6A. Attachment assembly 170 includes bracket 172 configured to interconnect with recharge coil container 118B. For example, bracket 172 may define cylindrical protrusion 174 that is configured to be received by bore 176 of recharge coil container 118 when bore cylindrical protrusion 178 is moved toward bore 176 along common axis 178. Cylindrical protrusion 174 and bore 176 may define a snap fit or interference fit, where outer diameter 178 of cylindrical protrusion 174 is substantially similar or slightly larger than inner diameter 178 of bore 176.

Further, bracket 172 may define channel 180 that is configured to receive ridge 182 of recharge coil container 118B. Channel 180 may be disposed around a portion of, or completely around, cylindrical protrusion 178, while ridge 182 is disposed partially or completely around bore 176. In other examples, channel 180 may extend around cylindrical protrusion 178 (and therein ridge 182 may extend around bore 176) in a shape other than a circle (e.g., a square, rectangle, or at multiple locations in a pattern). Channel 180 and ridge 182 may define a snap fit or interference fit such that outer dimensions of ridge 182 are at equal or bigger than respective inner dimensions of channel 180.

Bracket 172 may define lip 184 that is configured to extend around outer edge 186 of coil container 118B. As a result of interference fits between ridge 182 and channel 180 as well as between cylindrical protrusion 174 and bore 176, lip 184 press against outer edge 186 to secure bracket 172 to coil container 118B. One or more of these interference fits may be configured to secure bracket 172 to coil container 118B in such a way that bracket 172 and coil container 118B are unlikely to uncouple absent a user purposefully prying apart bracket 172 and coil container 118B.

Attachment assembly 170 may include pin 188. Pin 188 may be configured to be received by cylindrical recess 190. Pin 188 may be received with a press/interference fit or the like (though interference fit is discussed below for purposes of clarity). In some examples, pin 188 may be configured such that pin 188, by itself, does not define a press fit with cylindrical recess 190, but rather pin 188 is received by cylindrical recess 190 as a result of a material of flexible body 110 occupying some space between pin 188 and cylindrical recess 190. In other examples, a hole may be created in flexible body 110 as described below through which pin 188 extends unencumbered to be securely received by cylindrical recess 190 with an interference fit. Cylindrical recess 190 may be centered on assembly axis 178. Cylindrical recess 190 may extend into cylindrical protrusion 174 that extends from opposite side of bracket 172. In other examples, cylindrical recess 190 may include or be replaced with a bore that extends through bracket 172. Plate 192 at end of pin 188 may be nearly flush with surface 194 of bracket 172 when pin 188 is received by cylindrical recess 190. Pin 188 may be configured to extend from outer major surface (e.g., first major surface 126 of FIG. 4A) of flexible body 100 to inner major surface (e.g., second major surface 128 of FIG. 4A), such that plate 192 presses against the outer major surface and surface 194 of bracket 172 presses against inner major surface.

In some examples, attachment assembly 170 may include piercing component 196 configured to receive pin 188. Piercing component 196 may include a sharp tip that is sharp enough to pierce flexible body 110. Piercing component 196 may be configured to be received by pin 188 such that piercing component 196 may create a hole through which pin 188 may then extend to secure bracket 172 and therein coil container 118B to flexible body 110. For example, Coil container 118B may be navigated to a specific predetermined location on inner major surface (e.g., second major surface 128 of FIG. 4A), in response to which a user may use piercing component 196 as secured to pin 188 to create a hole in flexible body 110 by pushing piercing component 196 through bore 176. Once the hole is created in flexible body 110, piercing component 196 may be discarded because piercing component is not part of the completed attachment assembly 170. Then, bracket 172 may be secured to coil container 118B and pin may be pushed through the hole (which is in correct spot as a result of piercing component 196 making hole when coil container 118B is held at the predetermined location) and secured to bracket 172.

Figure 7A:
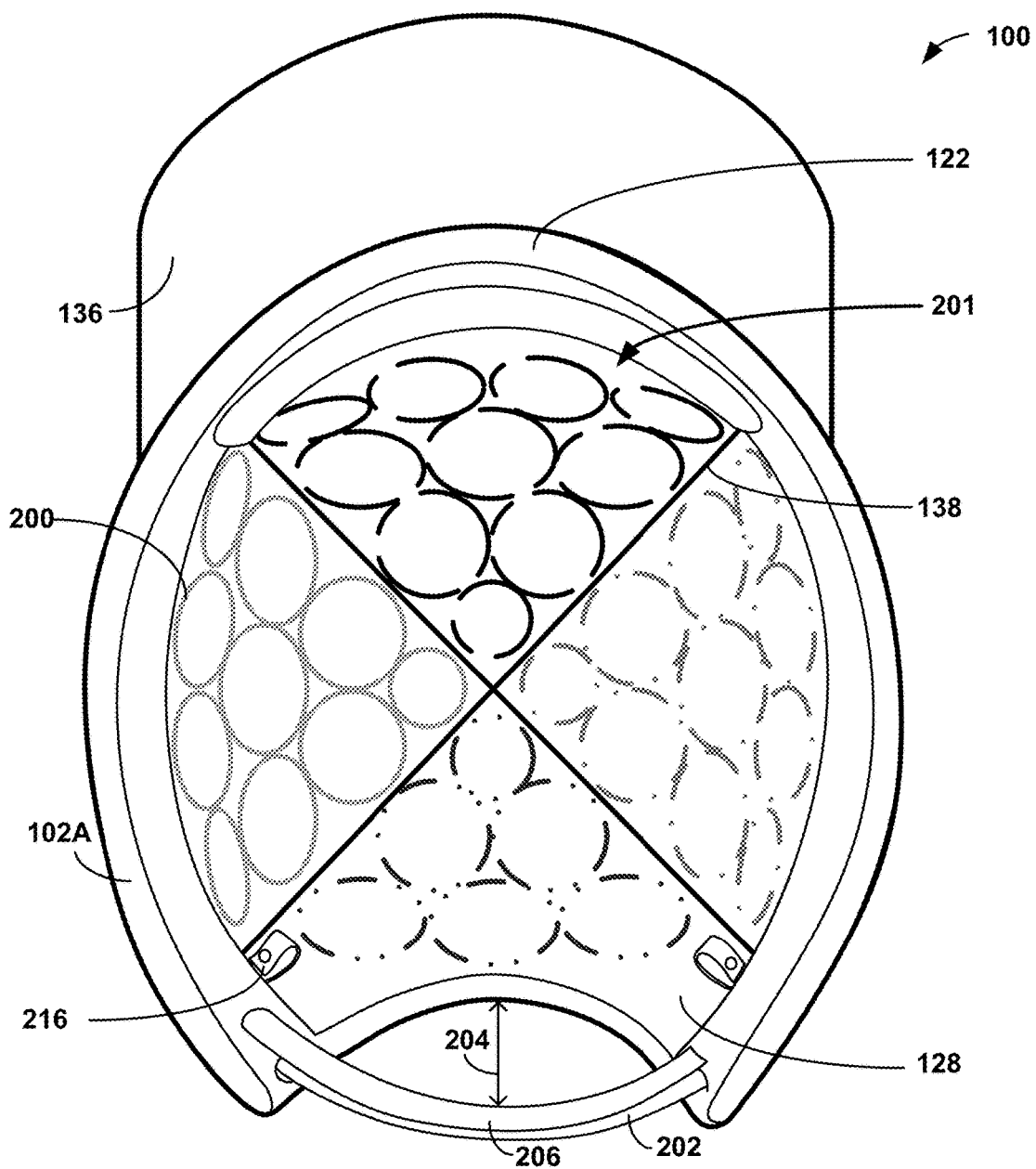
FIGS. 7A, 7B, and 7C are conceptual diagrams illustrating a bottom view of the securing member and flexible body of the wearable medical device of FIG. 4A along with a first, second, and third example adjustment mechanism for the securing member, respectively.

The bore 176 of coils 118 may also facilitate determining the location on the flexible body to place pin 188 and attach bracket 172 to the pin 188. For example, while the patient is wearing the wearable medical device and flexible body is disposed over the scalp, a user may position coil 118 over the external surface of flexible body. With feedback provided by recharging device 103, for example, regarding the correct alignment of coil 118 to the secondary coil of the IMD 14 under coil 118, the user may insert a marker, pen, pin, or other marking device through the to place a mark or create a small hole in the flexible body FIG. 7A depicts a conceptual diagram of mapping 201 on second major surface 128 of flexible body 110. Mapping 201 may include visual indications on second major surface 128 that correlate to a plurality of predetermined locations at which recharge coil contains 118 may be secured. For example, as depicted in FIG. 7A, mapping 201 may include circular indicators 200A-200D (collectively, "indicators 200"). In some examples, each of the plurality of circular indicators 200 may include a unique identifier such as a number, letter, or the like to identify each of the indicators 200. Further, as depicted in FIG. 7A, in some examples indicators 200 may look visually different in different quadrants of second major surface 128 as divided by seams 138 of flexible body 110. For example, indicators 200 of different quadrants may be colored differently, or may define relatively different shapes, or may be may be "drawn" on second major surface 128 with relatively different lines as depicted in FIG. 7A. Altering an appearance of indicators 200 across second major surface may improve an ability of a user to identify to utilize the selected indicator 200 and therein the selected predetermined location. The location identified by the circular indicators 200 of the map may be used by the patient to identify the correct location to re-attach a bracket or other fixation member used to attach recharge coils to wearable medical device 101.

Wearable medical device 101 may include securing member 102A, which may be substantially similar to securing member 102 with the exception of any differences described herein. In some examples, wearable medical device 101 may include adjustment mechanism that may functionally adjust a circumferential length of securing member 102A, therein adjusting a fit of wearable medical device 101 on head 12 of a respective patient. The adjustment mechanism may be located at a posterior section 124 of wearable medical device 101. For example, as depicted in FIG. 7A, portion 202 of securing member 102A may extend out from flexible body 110. Further, flexible body 110 may extend out distance 204 from portion 202 of securing member 102A, therein enabling securing member 102A to increase or reduce a circumferential length of securing member 102A.

Adjustment mechanism may include hook and loop strap 206 that is circumferentially aligned with portion 202 of securing member 102. Portion 202 of securing member 102 may also have a mating hook and loop strip, such that depending upon a length of hook and loop strap 206 that is mated with respective hook and loop strip of portion 202, a circumferential length of securing member 102 may be changed.

Figure 7B:
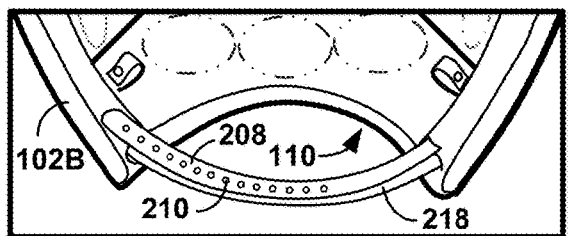
Figure 7C:
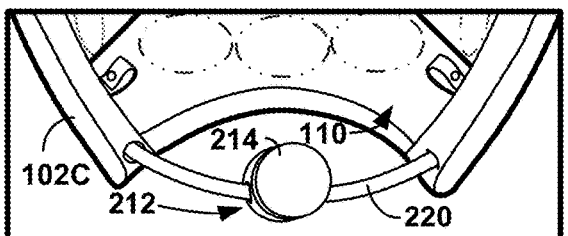

FIGS. 7B and 7C depict conceptual diagrams of posterior 124 of wearable medical device 101 with different example adjustment mechanisms. For example, FIG. 7B depicts mating strap 208 that defines a plurality of holes 210. Holes 210 may correspond to differing circumferential lengths of securing member 102B, which may be substantially similar to securing member 102A with the exception of any differences described herein. Portion 218 of securing member 102B may define one or more prongs or pins (not depicted) that are configured to extend out from securing member 102 to be securely received by holes 210. By adjusting or modifying holes 210 through which pins of portion 218 of securing member 102B are extending, wearable medical device 101 may functionally alter an internal circumferential length of securing member 102B.

For another example, FIG. 7C depicts click wheel 212 that is configured to increase or decrease a circumferential length of securing member 102C, which may be substantially similar to securing members 102A, 102B with the exception of any differences described herein. For example, when rotatable or movable portion 214 of click wheel 212 is turned in a first direction, click wheel 212 may collect and internally secure a length of portion 220 of securing member 102C, therein reducing a length securing member 102C (e.g., by storing an associated amount of portion 220 of securing member 102C within click wheel 212). Similarly, when rotatable or movable portion 214 of click wheel 212 is turned in a second and opposite direction, click wheel 212 may release and "output" a length of portion 220 of securing member 102C, therein increasing the overall circumferential length of securing member 102C by the released amount.

In some examples, wearable medical device 101 may include one or more clips 216 configured to securing cables 120 at one or more locations adjacent second major surface 128. Clips 216 may be movable, such that cables 120 may be secured at different relative locations along wearable medical device 101. Clips 216 may be configured to secure cables 120 to securing member 102 and/or flexible body 110. Utilizing clips 216 to secure cables 120 to different areas of charging device 100 may increase a comfort of wearable medical device 101 as well as avoiding cables 120 "kinking" as cables 120 are routed between power source compartment 116 and charging coil containers 118.

Figure 8B:
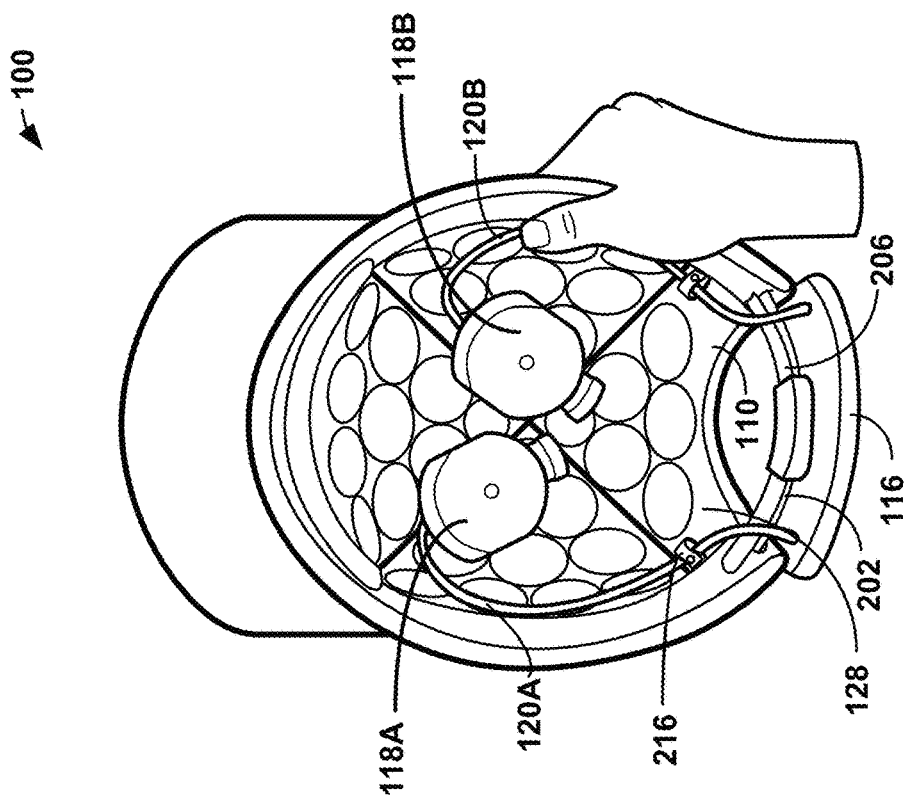
FIGS. 8A and 8B are conceptual diagrams illustrating a bottom view of the wearable medical device of FIG. 4A in a partially configured and fully configured state, respectively.
Figure 8A:
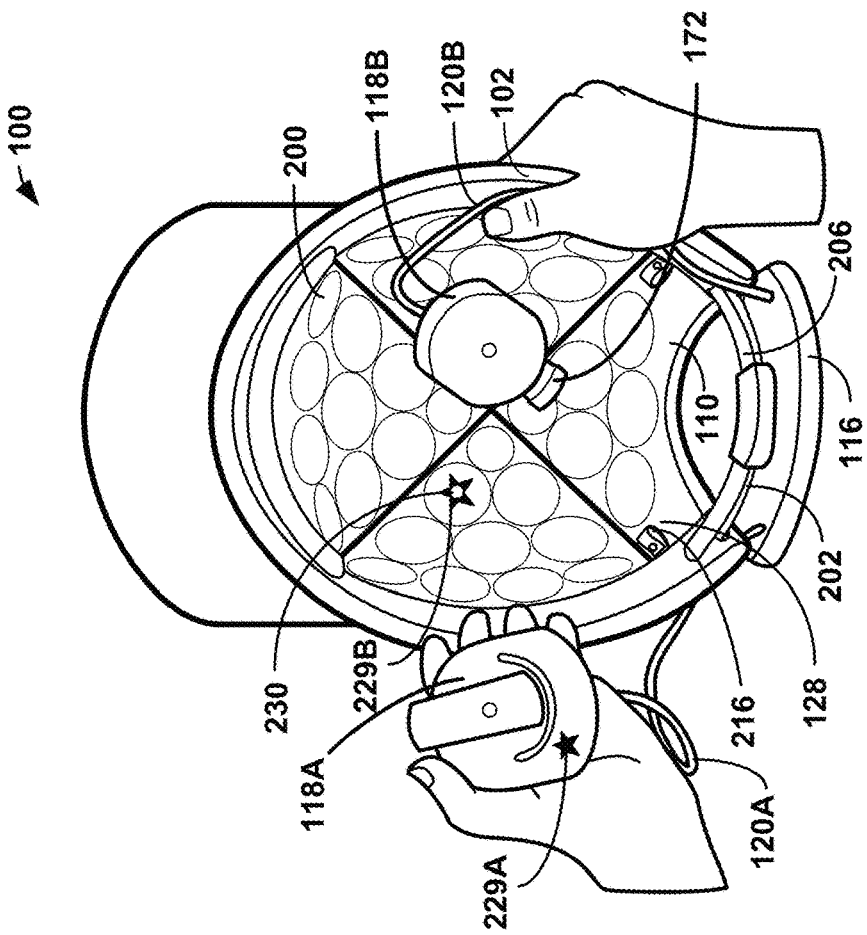

FIGS. 8A and 8B depict conceptual diagrams of charging system 100 as charging coil containers 118 are secured to second major surface 128 of flexible body 110. Though FIGS. 8A and 8B depict hook and loop strap 206 adjustment mechanism for purposes of illustration, it is to be understood that in other examples other adjustment mechanisms may be used consistent with this disclosure. Further, indicators 200 are depicted without visual differences of color or line in FIGS. 8A and 8B for purposes of clarity, though it is to be understood that in other examples indicators 200 may include many different colors or line types across different indicators.

FIG. 8A depicts power source compartment 116 secured to portion 202 of securing member 102 and hook and loop strap 206 and one recharge coil container 118B secured to second major surface 128 of flexible body 110. Put differently, bracket 172 may be secured to second major surface 128 of flexible body 110 as a result of pin 188 extending through second major surface 128 (not depicted) while recharge coil container 118B is secured to bracket 172. As depicted in FIG. 8A, cables 120 of recharging device 103 may be unsecured as cables 120 extend from power source compartment 116 to recharge coil container 118B. Piercing member 196 may have already created hole 230 through which another pin 188 may extend to secure to another bracket 172 to which recharge coil container 118A is secured.

In some examples, one or both coil containers 118 may contain marker 229A that indicates a location on flexible body 110 at which the respective container 118 is to be located. For example, coil container 118A includes marker 229A that matches marker 229B on flexible body 110. While only one indicator 200 is depicted with marker 229B in FIG. 8A for purposes of clarity, in some examples each indicator may have a respective marker 229B. Marker 229B on flexible body 110 may be unique to indicator 200, such that each indicator 200 may have a relative unique marker 229B so that a user may remember which indicator 200 coil container 118A is to be secured to. Though marker 229A on coil container 118A is depicted as substantially identical to marker 229B on flexible body 110 for purposes of illustration, in other examples one marker 229A may be different than other marker 229B. Though markers 229A, 229B are depicted as geometric shapes (stars) in FIG. 8A for purposes of illustration, markers 229A may be any alphanumeric symbol or visual identifier consistent with the disclosure herein.

FIG. 8B depicts recharge coil container 118A as secured to second major surface 128 of flexible body 110. Recharge coil container 118A may be secured to flexible body 110 through pin 188 extending through hole 230 (not depicted) to be received by bracket 172 secured to recharge coil container 118A. As depicted in FIG. 8B, cables 120 may be secured to recharging device 103 through the use of one or more clips 216. In some examples, each cable 120 may be secured by at least one clip 216.

Figure 9B:
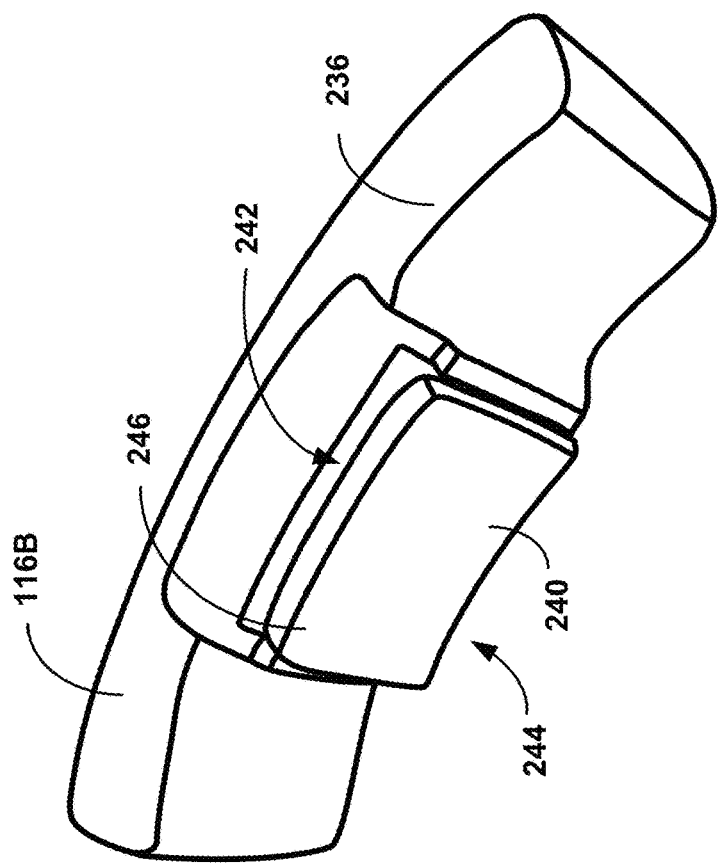
FIGS. 9A and 9B are conceptual diagrams illustrating a perspective views of a power unit for the recharging device of FIG. 4A with different securing mechanisms.
Figure 9A:
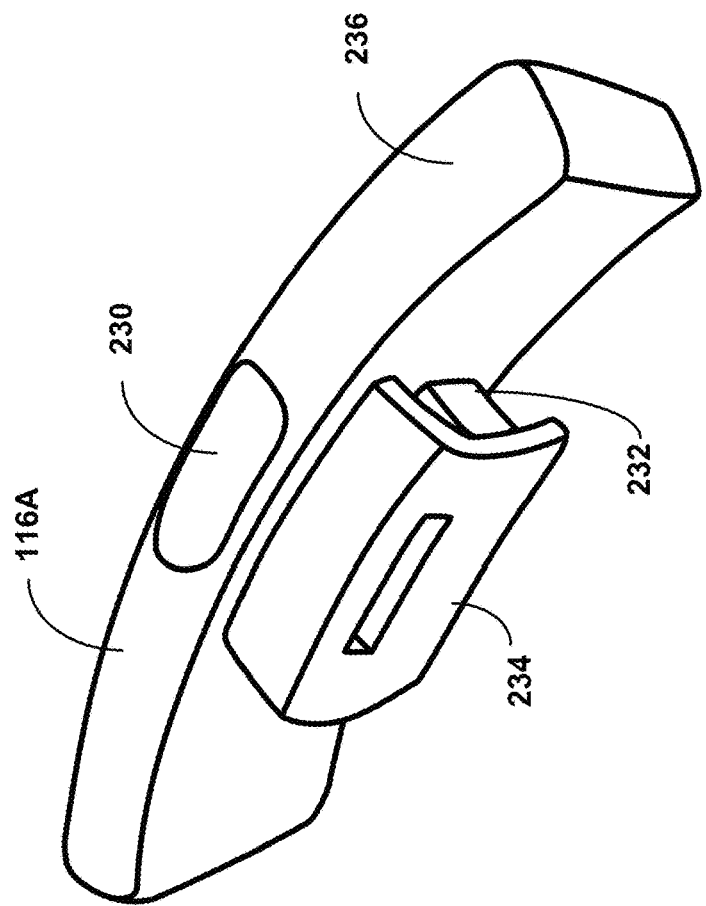

FIGS. 9A and 9B depict conceptual diagrams of power source compartment 116A, 116B with different securing mechanisms. For example, power source compartment 116A may include button 230 that releases block 232 that pushes into clip 234. When button 230 is depressed, block 232 may move back toward central housing 236 of power source compartment 116A. In this way, an operator may secure power source compartment 116A to securing member 102, for example, but pressing button 230 and maneuvering securing member 102 between clip 234 and power source central housing 236.

Alternatively, power source compartment 116B may include a clip. For example, power source compartment 116B includes cavity 242 into which pivot member 240 may pivot. Pivot member 240 may pivot such that a gap appears between pivot member 240 and central house 236 of power source compartment 116B near bottom 244 of power source compartment 116B. A person may press into top portion 246 of pivot member 240 to make gap appear near bottom 244 of power source compartment 116B. Once pressed, a person may maneuver securing member 102 into gap between pivot member 240 and central housing 236 of power source compartment 116B.

While wearable medical device 101 of FIGS. 4A-9B is depicted as primarily a billed cap, wearable medical device 101 may be constructed into different shapes while still securing recharging devices (e.g., recharging device 103) to the head of a patient. For example, FIGS. 10A-31C depicts various conceptual diagrams of example wearable medical device, and recharging devices in some examples, that include example securing members, example bodies, example power sources, example recharge coils, and example leads connecting the power sources and leads. Recharge coils of the following recharging devices may be shaped according to recharge coils 80, 82, 84, 86 of FIGS. 3A-3D. These recharge coils may be encased in a relatively rigid or flexible housing, wherein some suitable rigid materials for the housing include, without limitation, Acrylonitrile butadiene styrene (ABS), Polyvinyl chloride (PVC), polycarbonate, high-density polyethylene (HDPE), Polyether ether ketone (PEEK), Polyethylene terephthalate (PET), and polypropylene, and some suitable flexible materials for the housing include, without limitation, silicone rubber, and thermoplastic elastomer.

FIGS. 10A-10C depict conceptual diagram illustrating perspective views of wearable medical device 300 in the form of a cap for mounting to head 12 of patient, on an exterior side of scalp 16 of the patient. Wearable medical device 300 may include securing member 302 that is substantially similar to securing member 102 with exception to any differences described herein. Securing member 302 may extend around head 12 in a generally horizontal plane (that is, across forehead 106 of patient, alongside both ears, and across the posterior portion of scalp 16 adjacent the neck of the patient—as illustrated in FIGS. 10A-10C). In some examples, securing member 302 may include a small band that extends around the perimeter of wearable medical device 300. In other examples, securing member 302 may also include a relatively flexible material that is configured to fit over head 12 of patient and conform to at least a portion of each of the left anterior, right anterior, left posterior, and right posterior quadrants LAQ, RAQ, RPQ, LPQ (e.g., of FIG. 1) of scalp 16 of the patient. In other examples, wearable medical device 300 includes flexible body 310 configured to conform to scalp 16 by extending between securing member 302. FIG. 10A-10C further illustrates wearable medical device 300 including a plurality of holding features 304 attached to flexible body 310, wherein each holding feature 304 is configured to hold one of recharging coil container 318. Recharging coil container 318 may be substantially similar to recharging coil container 118. The plurality of holding features 304 may include at least one feature 304 located in each quadrant of scalp 16 of the patient when wearable medical device 300 is mounted to head 12 of patient, for example, holding feature 304A located in the left anterior quadrant, holding feature 304B located in the right anterior quadrant, holding feature 304C located in the right posterior quadrant, and holding feature 304D located in the left posterior quadrant.

Thus, the patient can choose the appropriate holding feature 304 into which a respective recharging coil container 318 may be inserted to correspond with the location of the implant site of the patient's medical electrical system when wearable medical device 300 is mounted to head 12. With further reference to FIGS. 10A-10C, another holding feature 306 is shown included in wearable medical device 300. Holding feature 306 may be configured to hold power source compartment 316. Holding features 304, 306 may be pockets formed between an inner layer 313A and an outer layer 313B of flexible body 310. Holding features 304, 306 may be configured to be accessible from inner layer 313B. Alternatively, holding features 304, 306 may be configured to be accessible from outer layer 313A. In some examples, the holding features of any of the examples herein may alternatively or further comprise loop-and-hook features such as VELCRO™ brand hook-and-loop features, snaps, hooks, elastic or other stretchable bands, buttons, zippers, or any other type of holding features. Wearable medical device 300 may be formed from a polyester/Spandex blend, and/or Lycra, and/or cotton, so that securing member 302 and flexible body 310 are configured conform to the exterior side of scalp 16 of the patient to maintain a stable position of recharge coil container 318.

Figure 11A:
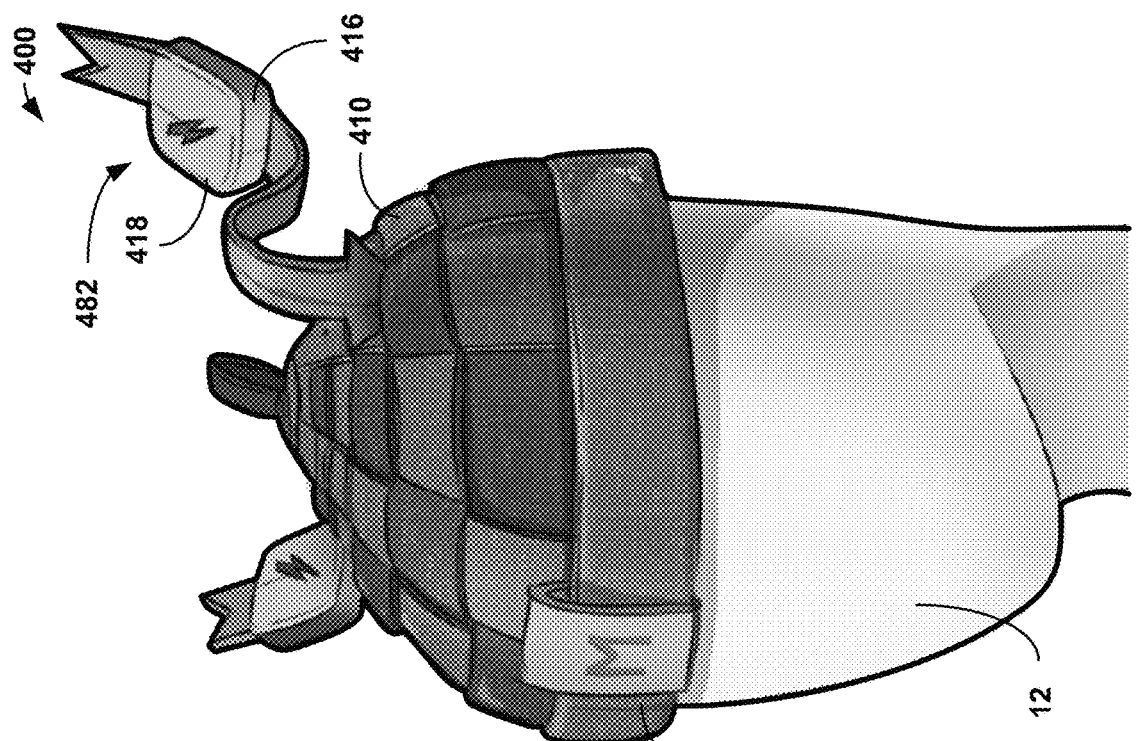
FIGS. 11A, 11B, and 11C are conceptual diagrams illustrating an example wearable medical device that may be used to recharge a power source of the IMD of FIG. 1A.
Figure 11B:
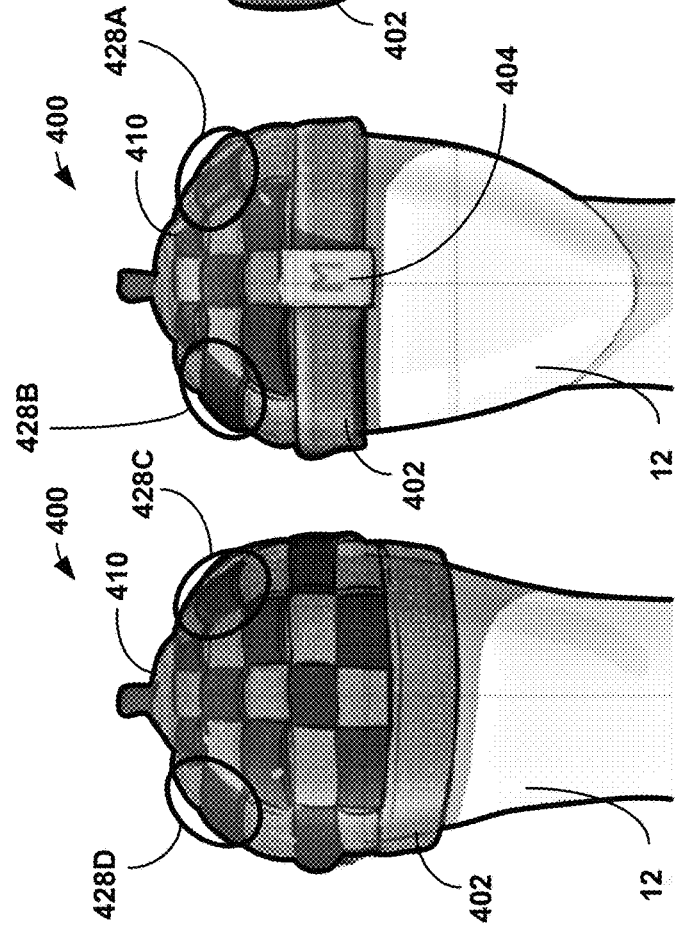
Figure 11C:
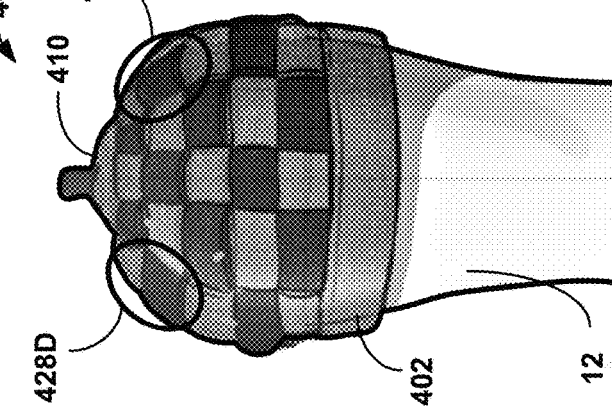
Figure 12C:
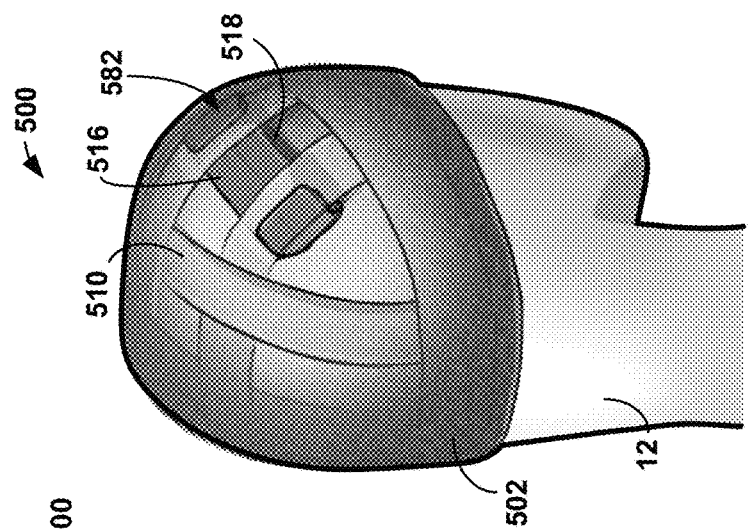
FIGS. 12A, 12B, 12C, and 12D are conceptual diagrams illustrating an example wearable medical device that may be used to recharge a power source of the IMD of FIG. 1A.
Figure 12B:
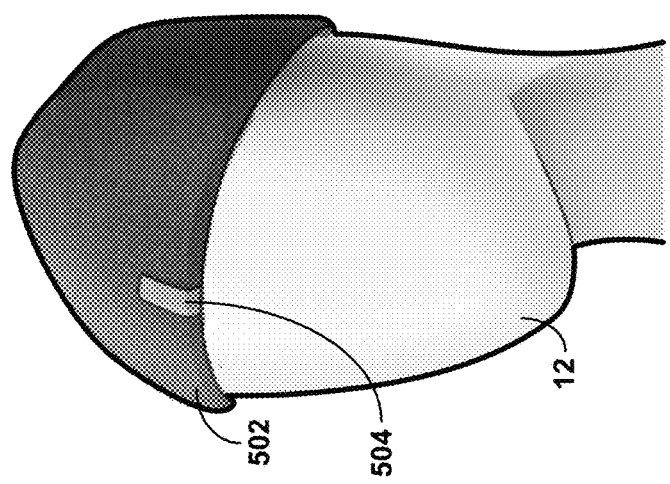
Figure 12D:
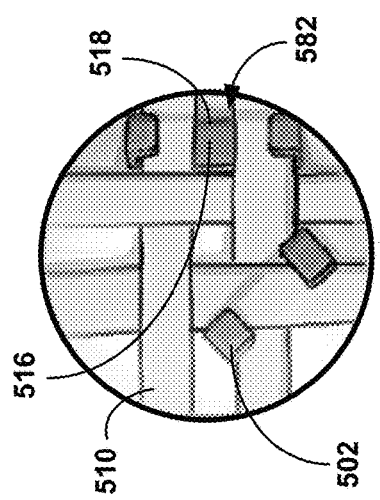
Figure 12A:
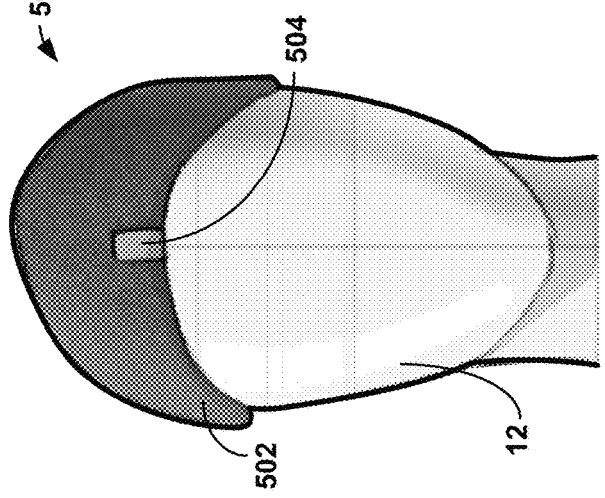

FIGS. 11A-11C includes various views of wearable medical device 400. Wearable medical devices 400 may include recharging units 482 into which recharge coil containers 418 (which are substantially similar to recharge coil containers 118, 318 except for differences described herein) and power source compartment 416 (which are substantially similar to power source compartments 116, 316 except for differences described herein) are integrated. For example, a first side of recharging unit 482 which is oriented toward scalp 16 may contain recharge coil container 418 and therein one of coils 80, 82, 84, 86, while the other side of recharging unit 482 may contain power source compartment 416. These recharging units 482 may include a relatively rigid or flexible housing, wherein some suitable rigid materials for the housing include, without limitation, ABS, PVC, polycarbonate, HDPE, PEEK, PET, and polypropylene, and some suitable flexible materials for the housing include, without limitation, silicone rubber, and thermoplastic elastomer.

FIGS. 11A-11C illustrates securing member 402. Securing member 402 may be substantially similar to securing member 102, 302 with the exception of any differences described herein. Securing member 402 may be formed in part by a head band for mounting to a head 12 of the patient, on an exterior side of scalp 16 of the patient, so that securing member 402 band may extend around head 12 in a generally horizontal plane, and along each of the left anterior, right anterior, left posterior, and right posterior quadrants LAQ, RAQ, RPQ, LPQ (FIG. 1) of scalp 16 of the patient. FIGS. 11A-11C further illustrates recharging device 400 including flexible body 410. Flexible body 410 may be substantially similar to flexible bodies 110, 310 with the exception of any differences described herein. Flexible body 410 may be formed by a woven latticework of flexible strips attached to securing member 402, wherein the latticework defines a plurality of pockets or holding features 428. According to some examples, securing member 410 and flexible body 410 of wearable medical device 400 are made from an elasticized material, such as a polyester/Spandex blend, and/or Lycra, and/or cotton. Each holding feature 428 may be configured to hold one of charging units 482 therein, and the plurality includes at least one located in each quadrant of scalp 16 of the patient when securing member 402 is mounted to head 12 of the patient.

For example, holding feature 428A is located in the left anterior quadrant, holding feature 428B located in the right anterior quadrant, holding feature 428C located in the right posterior quadrant, and holding feature 428D located in the left posterior quadrant. Thus, the patient can choose the appropriate holding feature 428, in which to insert each charging unit 482 so that the held location of each charge unit 482 corresponds to the location of each IMD 14 implant site. An orientation indicator 404 is shown mounted to securing member 402 so that once the patient has selected the appropriate holding feature(s) 428, recharging device 400 can be donned in the proper orientation corresponding to the selected holding features 428 for each successive charging session.

FIGS. 12A-12D depict conceptual diagrams illustrating various views of wearable medical device 500, which may be substantially similar to wearable medical device 100, 300, or 400 with the exception of any differences described herein. Wearable medical devices 500 may include recharging units 582 into which recharge coil containers 518 (which are substantially similar to recharge coil containers 118, 318, and 418 except for differences described herein) and power source compartment 516 (which are substantially similar to power source compartments 116, 316, and 416 except for differences described herein) are integrated. For example, a first side of recharging unit 582 which is oriented toward scalp 16 may contain recharge coil container 518 and therein one of coils 80, 82, 84, 86, while the other side of recharging unit 582 may contain power source compartment 516.

FIGS. 12A-12D illustrates wearable medical device 500 including securing member 502 in the form of a cap for mounting to head 12 of the patient. Securing member 502 may be configured to extend around and conform to head 12 on an exterior side of scalp 16 of the patient along each of the left anterior, right anterior, left posterior, and right posterior quadrants (FIG. 1) of scalp 16 of the patient. Securing member 502 may be an outer layer of wearable medical device 500, while flexible body 510 is functionally an inner liner of wearable medical device 500. Flexible body 510 may be made up of a latticework of flexible strips that forms a plurality of holding features to engage hooked ends 502 of each charge module 582 at any selected location along the latticework. In this way, charge module(s) 582 may be held in a pocket between securing member 502 and flexible body 510. Like wearable medical device 400, wearable medical device 500 includes orientation indicator 504 so that wearable medical device 500 can be donned in the proper orientation corresponding to the selected location of each charge module 582 for each successive charging session. According to some examples, flexible body 510 may be made from ABS, PVC, polycarbonate, HDPE, PEEK, PET, or polypropylene, and securing member 502 may be made from a polyester/Spandex blend.

Figure 13C:
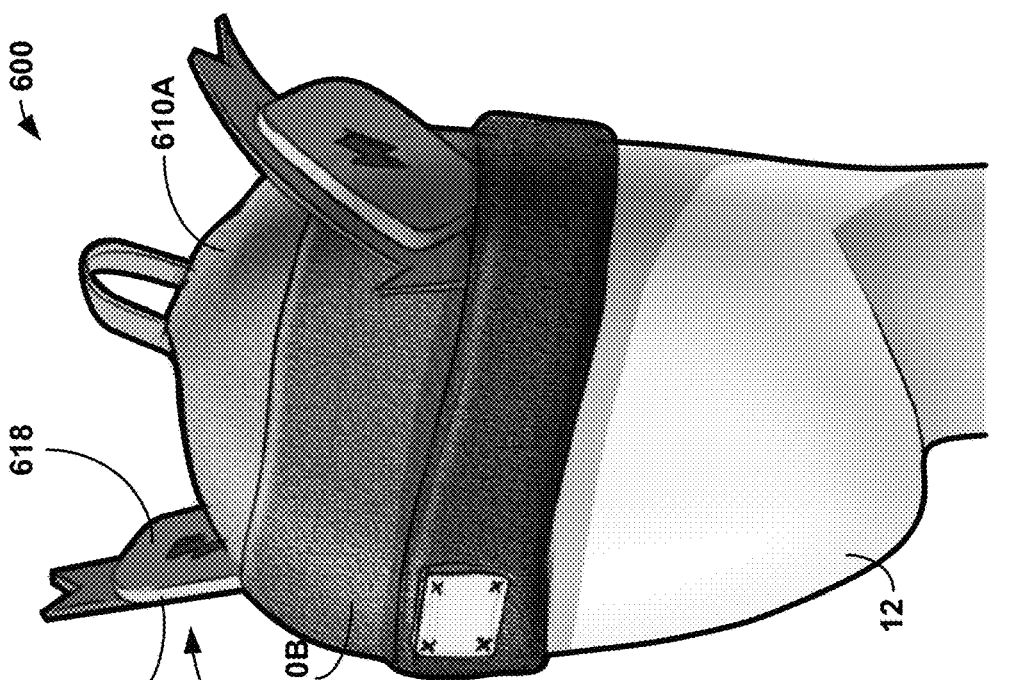
FIGS. 13A, 13B, and 13C are conceptual diagrams illustrating an example wearable medical device that may be used to recharge a power source of the IMD of FIG. 1A.
Figure 13B:
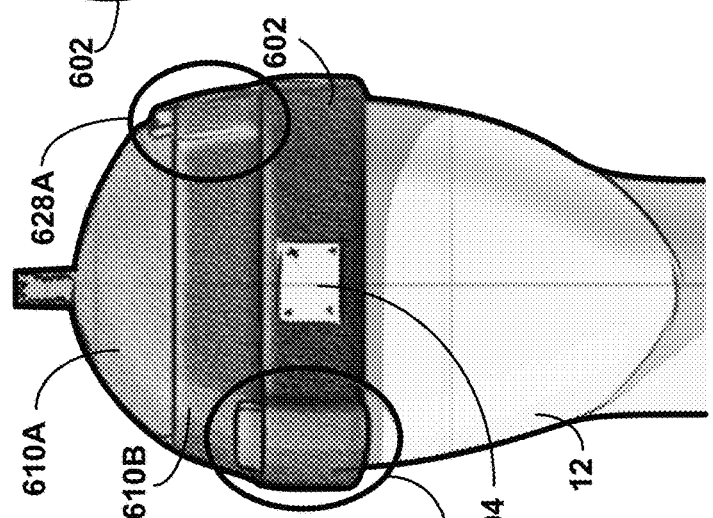
Figure 13A:
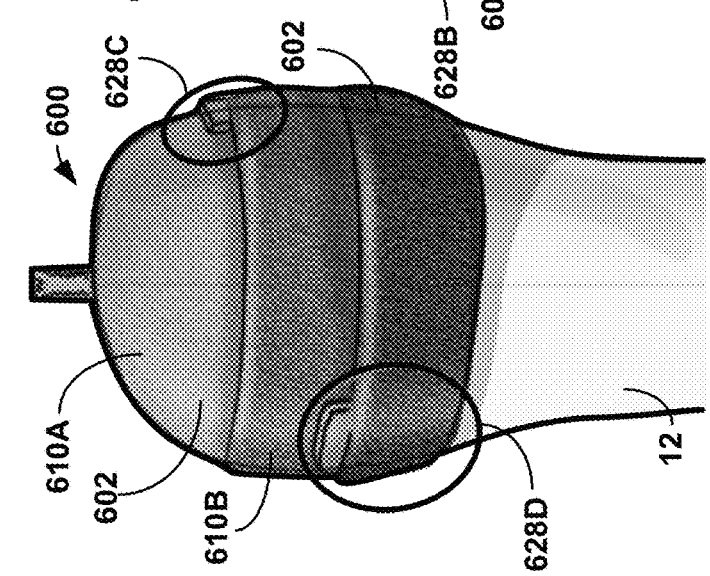

FIGS. 13A-13C depict conceptual diagrams illustrating various views of wearable medical device 600, which may be substantially similar to wearable medical device 100, 300, 400, and 500 with the exception of any differences described herein. Wearable medical devices 600 may include recharging units 682 into which recharge coil containers 618 (which are substantially similar to recharge coil containers 118, 318, 418, and 518 except for differences described herein) and power source compartment 616 (which are substantially similar to power source compartments 116, 316, 416, and 516 except for differences described herein) are integrated. For example, a first side of recharging unit 682 which is oriented toward scalp 16 may contain recharge coil container 618 and therein one of coils 80, 82, 84, 86, while the other side of recharging unit 682 may contain power source compartment 616.

FIGS. 13A-13C illustrates wearable medical device 600 including securing member 602 (which may be substantially similar to securing member 102, 302, 402, and 502 except for differences described herein). Securing member 602 may be formed in part by a head band configured to mounting to head 12 of the patient on an exterior side of scalp 16. As such, securing member 602 may be configured to extend around the head in a generally horizontal plane as mounted to head 12 along each of the left anterior, right anterior, left posterior, and right posterior quadrants (FIG. 1) of scalp 16 of the patient.

FIGS. 13A-13C further illustrates flexible body 610 of wearable medical device 600. Flexible body 610 may be a cap that is attached to securing member 602 and is configured to extend between securing member 602. Flexible body 610 may include an inner layer 610A and an outer layer 610B between which a pocket or group of pockets are formed 360 degrees around the cap perimeter, to provide a plurality of holding features for charge unit 682. Thus, the patient can choose the appropriate location(s) around the perimeter of wearable medical device 600 between inner layer 610A and outer layer 610B of flexible body 610 in which to insert each charge module 682 so that the held location of each charge module 682 corresponds to the location of each IMD 14 implant site. Outer layer 610B of flexible body 610 may further extend radially within securing member 602, between which another set of one or more pockets are formed that extend 360 degrees around the perimeter of securing member 602 to provide another plurality of holding features for charge module 682.

FIGS. 13A-13C illustrates a plurality of charge units 682 held by recharging device 600 when securing member 602 is mounted to head 12 of the patient. For example, FIGS. 13A-13C depicts charge units 682 as secured to head 12 of patient in the left anterior quadrant as secured by holding feature 628A, in the right anterior quadrant as secured by a holding feature 628B, in the right posterior quadrant as secured by a holding feature 628C, and in the left posterior quadrant as secured by holding feature 628D. Recharging device 600 may include orientation indicator 604, which may be substantially similar to orientation indicator 404 and 504. According to some examples, securing member 602 and flexible body 610 of wearable medical device 600 are made from an elasticized material, such as a polyester/Spandex blend.

FIGS. 14A-14E depict conceptual diagrams illustrating various views of wearable medical device 700, which may be substantially similar to recharging device 100, 300, 400, 500, and 600 with the exception of any differences described herein. Wearable medical devices 700 may include recharging units 782 into which recharge coil containers 718 (which are substantially similar to recharge coil containers 118, 318, 418, 518, and 618 except for differences described herein) and power source compartment 716 (which are substantially similar to power source compartments 116, 316, 416, 516, and 616 except for differences described herein) are integrated. For example, a first side of recharging unit 782 which is configured to be oriented toward scalp 16 may contain recharge coil container 718 and therein one of coils 80, 82, 84, 86, while the other side of recharging unit 782 may contain power source compartment 716.

FIGS. 14A-14D depict wearable medical device 700 as including a securing member 702 in the form of a cap for mounting to head 12 of the patient on an exterior side of scalp 16 of the patient. Securing member 702 may extend around the head in a generally horizontal plane (that is, across the patient's forehead, alongside both ears, and across the posterior portion of the scalp adjacent the patient's neck, as depicted in FIGS. 14A-14E). Wearable medical device 700 may substantially not include a flexible body as used herein, but rather securing member 702 may itself extend across at least a portion of each of the left anterior, right anterior, left posterior, and right posterior quadrants (FIG. 1) of scalp 16 of the patient. FIGS. 14A-14E further illustrates securing member 702 as defining a plurality of holding features 728, wherein each holding feature 728 is a recess formed in an outer surface of securing member 702. In some embodiments, the recesses defining holding features 728 may extend all the way through to an inner surface of securing member 702 to form through-holes. According to the illustrated embodiment, each holding feature 728 has a hexagonal shape corresponding to that of charge module 782. Holding features 728 may be configured to secure charge module 782 using a press fit or a snap fit or the like. The plurality of holding features 728 includes at least one feature 728 located in each quadrant of scalp 16 of the patient when securing member 728 is mounted to head 12 of the patient.

For example, as mounted to head, wearable medical device 700 may define holding feature 728A located in the left anterior quadrant, holding feature 728B located in the right anterior quadrant, and holding feature 728C located in the left posterior quadrant. Thus, the patient can choose the appropriate holding feature 728 in which to insert charge module 782, to correspond with the location of IMD 14 implant site. As a result of this functionality, recharging device 700 may increase an amount of which recharge coils 80, 82, 84, 86 are securely aligned with secondary coils of IMD 14 when recharging device 700 is secured to head 12. According to some examples, wearable medical device 700 may be fabricated from a sturdy and relatively lightweight foam, for example, a reinforced expanded polystyrene.

FIGS. 15A-15D depict conceptual diagrams illustrating various views of wearable medical device 800, which may be substantially similar to recharging device 100, 300, 400, 500, 600, and 700 with the exception of any differences described herein. Wearable medical device 800 may include securing member 802. Securing member 802 may include a flexible cap that is configured to be mounted to head 12 of the patient on an exterior side of scalp 16 of the patient. Wearable medical device 800 may substantially not include a flexible body as used herein, but rather securing member 802 may be configured to itself extend around head 12 in a generally horizontal plane (that is, across the patient's forehead, alongside both ears, and across the posterior portion of the scalp adjacent the patient's neck along each of the left anterior, right anterior, left posterior, and right posterior quadrants (FIG. 1) of scalp 16 of the patient.

Wearable medical device 800 may include holding features 828 of headgear 510. Securing member 802 may define at least one holding feature 828 on either side of midline 804 of wearable medical device 800, where midline 804 extends from a forehead of the patient substantially straight back to posterior of head 12. Securing member 802 may define one holding feature 828 on the left side of wearable medical device 800 and one holding feature 828 on the right side. Holding features 828 may be pockets formed between inner and outer layers of securing member 802. Holding features may be configured to securely receive coils 80, 82, 84, 86 within coil containers and coupled to power source compartments, and all components secured within.

FIGS. 15A-15D illustrates securing member 802 being divided into left portion 802L and a right portion 802R. Left portion 802L may be configured to conform to left anterior and posterior quadrants of scalp 16, while right portion 802R is configured to conform to right anterior and posterior quadrants of scalp 16 of the patient. In some examples, both left portion 802L and right portion 802R have a superior perimeter edge free to move away from and toward midline 804 plane of head 12 of the patient when securing member cap 513 is mounted to the head, for example, per arrow 806. Thus, the patient may adjust the position of one or both of the securely received recharging coils. Wearable medical device 800 is preferably formed from an elasticized material, such as Neoprene, so that securing member cap 802 will conform to the exterior side of scalp 16 of the patient to maintain a stable position of the held recharging coils. Furthermore, the held recharging coils may be cushioned by a flexible foam layer that extends alongside within holding features 828.

Figure 16B:
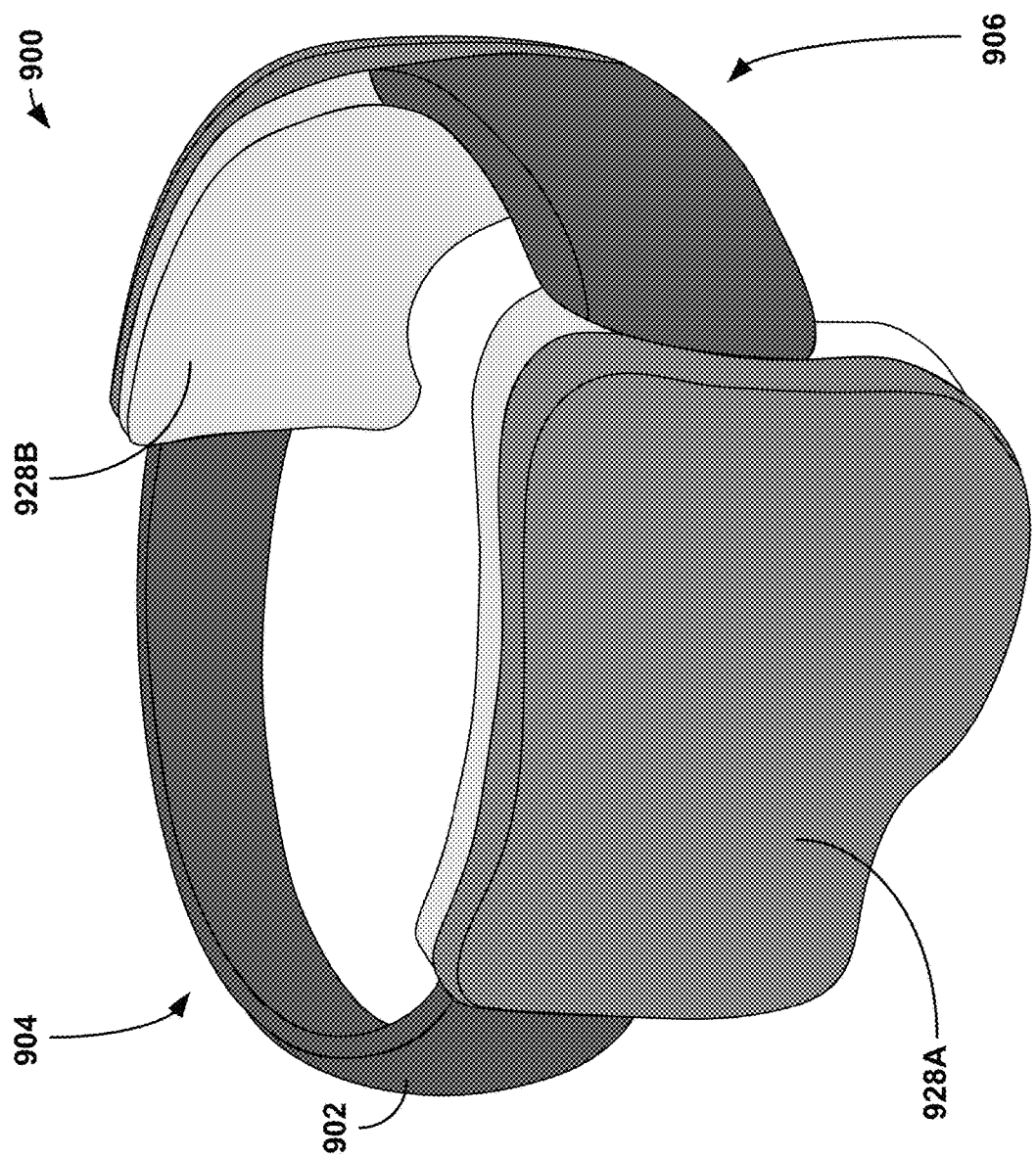
FIGS. 16A and 16B are conceptual diagrams illustrating an example wearable medical device that may be used to recharge a power source of the IMD of FIG. 1A.
Figure 16A:
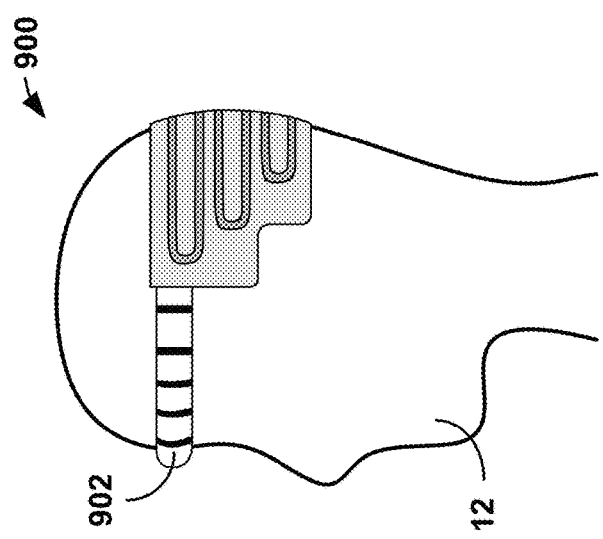
Figure 24B:
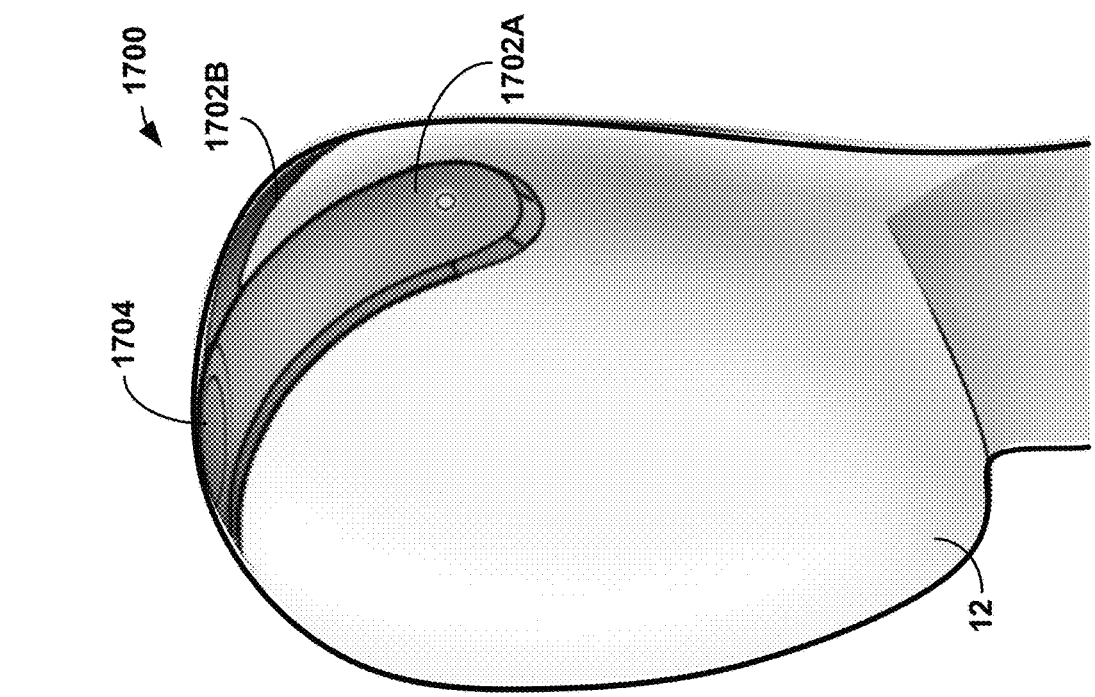
FIGS. 24A, 24B, 24C, and 24D are conceptual diagrams illustrating an example wearable medical device that may be used to recharge a power source of the IMD of FIG. 1A.
Figure 24D:
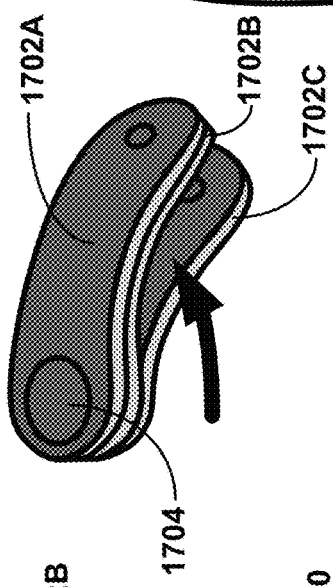
Figure 24C:
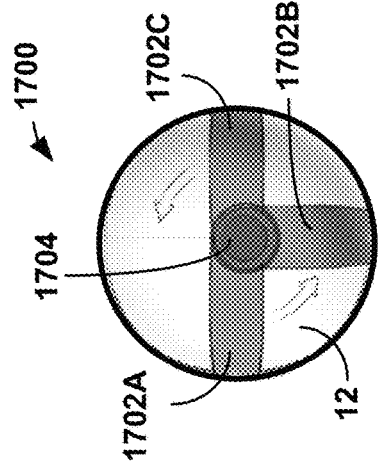
Figure 24A:
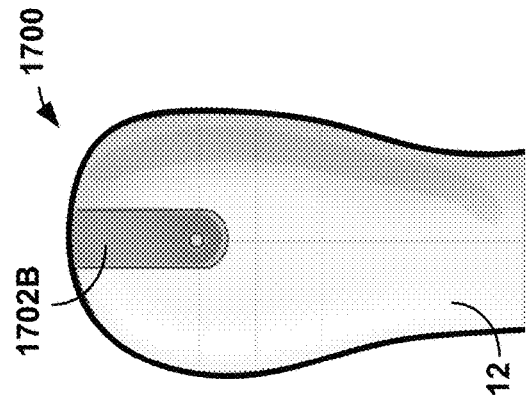
Figure 25H:
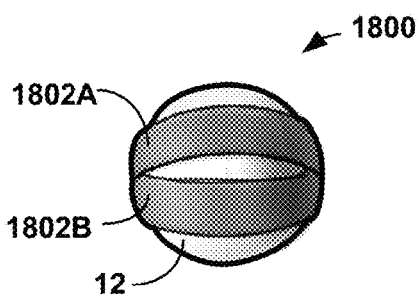
FIGS. 25A, 25B, 25C, 25D, 25E, 25F, 25G, and 25H are conceptual diagrams illustrating an example wearable medical device that may be used to recharge a power source of the IMD of FIG. 1A.
Figure 25G:
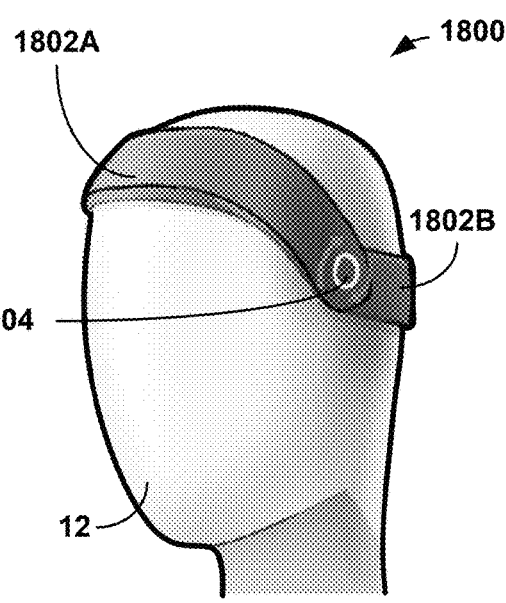
Figures 25E, 25F:
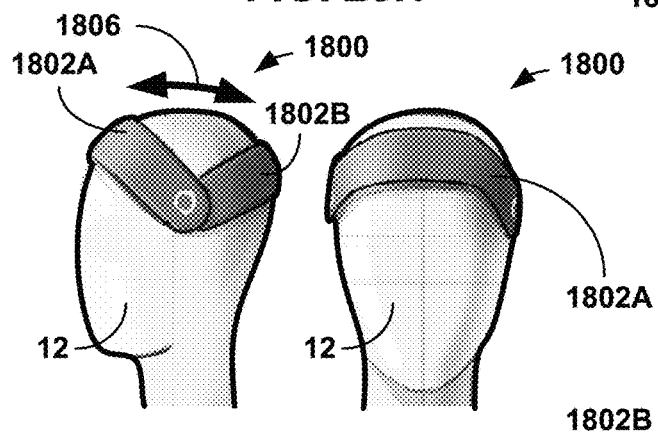
Figure 25D:
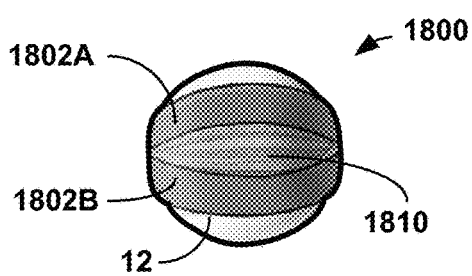
Figure 25C:
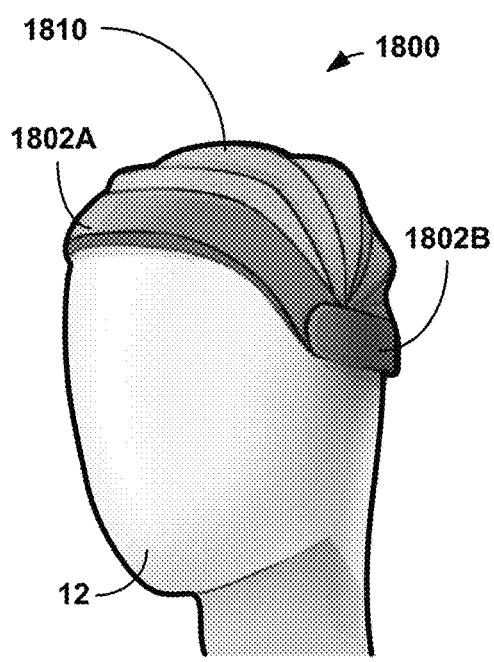
Figures 25A, 25B:
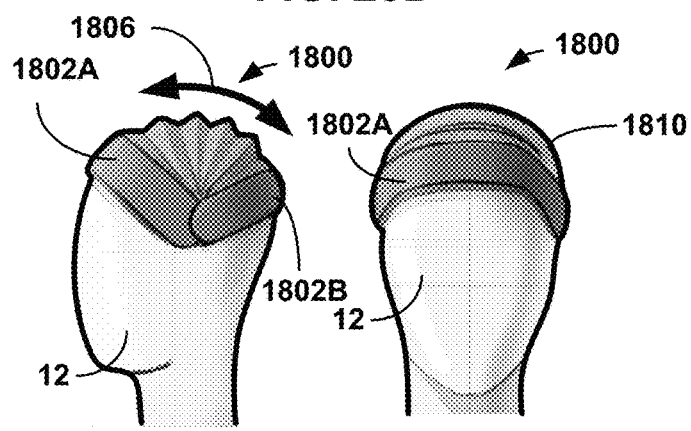

FIGS. 16A-16B depict conceptual diagrams illustrating various views of wearable medical device 900, which may be substantially similar to wearable medical device 100, 300, 400, 500, 600, 700, and 800 with the exception of any differences described herein. Wearable medical device 900 includes securing member 902, which, when mounted to head 12 of the patient, extends around the head in a generally horizontal plane and along each of the left anterior, right anterior, left posterior, and right posterior quadrants LAQ, RAQ, RPQ, LPQ (FIG. 1) of scalp 16 of the patient. Wearable medical device 900 includes at least two holding features 928. For example, recharging device 900 may include right posterior pad 928B and a left posterior pad 928A. Both left posterior pad 928A and right posterior pad 928B may be attached to securing member 902. In some examples, pads 928A, 928B may be flexible and cushioned. Further pads 928A, 928B may define pockets formed between inner and outer layers thereof. These pockets may be configured to hold recharging coils therein, for example, any of the above described coils 80, 82, 84, 86 (FIGS. 3B-D). According to some examples, pads 928A, 928B may be formed from one or more of the following materials: ABS, PVC, polycarbonate, HDPE, PEEK, PET, polypropylene, silicone rubber, and thermoplastic elastomer. A power source compartment and other components stored within (e.g., as depicted in FIG. 5) may be integrated with one or both of the recharging coils. These charging assemblies may be securely received within the corresponding pad 928A, 928B. Alternately, some portions of the power source compartment (e.g., as depicted in FIG. 5) unit may be received within or mounted on securing member 502. In some examples, anterior portion 904 of securing member 902 is formed from an elasticized material, such as a polyester/Spandex blend, and/or Lycra, and/or cotton, and posterior portion 906 of securing member 902 is formed from a relative rigid, but conformable, material, such as one or more of ABS, PVC, polycarbonate, HDPE, PEEK, PET, polypropylene, silicone rubber, and thermoplastic elastomer.

FIGS. 17A-17H depict conceptual diagrams illustrating various views of wearable medical device 1000, which may be substantially similar to wearable medical device 100, 300, 400, 500, 600, 700, 800, and 900 with the exception of any differences described herein. Wearable medical device 1000 may include recharging units 1082 into which recharge coil containers 1018 (which may be substantially similar to recharge coil containers 118, 318, 418, 518, 618, and 718 except for differences described herein) and power source compartment 1016 (which may be substantially similar to power source compartments 116, 316, 416, 516, 616, and 716 except for differences described herein) are integrated. For example, a first side of recharging unit 1082 which is configured to be oriented toward scalp 16 may contain recharge coil container 1018 and therein one of coils 80, 82, 84, 86, while the other side of recharging unit 1082 may contain power source compartment 1016 and any components stored within power source compartment 1016 (e.g., components of FIG. 5).

FIGS. 17A-17H depict wearable medical device 1000 with alternative securing members 1002A or 1002B that each, when mounted to head 12 of the patient, extends around head 12 in a generally horizontal plane and along each of the left anterior, right anterior, left posterior, and right posterior quadrants (FIG. 1) of scalp 16 of the patient. Securing member 1002A is shown being configured to extend around an entire perimeter of head 12 of the patient, while securing member 1002B is shown being configured to extend around just a portion of the perimeter of head 12 of the patient. FIGS. 17A-17H further illustrates multiple holding features 1004 of wearable medical device 1000 formed by flexible rails, which have opposing, left and right ends attached to respective securing members 1002A, 1002B. Holding features 1004 may extend in an arc superior to respective securing members 1002A, 1002B to span left and right quadrants of scalp 16 when the respective securing member 1002A, 1002B is mounted to head 12.

In some examples, charge modules 1082 may include a bracket, such as bracket 1012 of FIG. 17H. Brackets may be configured to enable holding features 1004 to securely receive charge units 1082. In some examples, brackets may receive charge units 1082 in sliding engagement therewith, so that the patient may slide, per arrow 1008 of FIG. 17C, respective charge units 1082A into a selected position to correspond with IMD 14 implant location. In some examples, as depicted, a cross-sectional shape of holding feature rails 1004 may be substantially being round or flat. In other examples, holding features 1004 may define other cross-sectional shapes that are configured to engage with the brackets of charge modules 1082. In some examples, the ends of each holding feature 1004 are attached with pivot joints to a respective securing member 1002A, 1002B so the patient can make further anterior/posterior adjustments, per arrow 1006 of FIG. 17B. In some examples, securing members 1002A, 1002B and holding feature rails 1004 are formed from a relatively resilient plastic, such as ABS, PVC, polycarbonate, HDPE, PEEK, PET, or polypropylene.

FIGS. 18A-18D depict conceptual diagrams illustrating various views of wearable medical device 1100, which may be substantially similar to recharging device 100, 300, 400, 500, 600, 700, 800, 900, and 1000 with the exception of any differences described herein. Wearable medical device 1100 may include recharging units 1182 into which recharge coil containers 1118 (which may be substantially similar to recharge coil containers 118, 318, 418, 518, 618, 718, and 1018 except for differences described herein) and power source compartment 1116 (which may be substantially similar to power source compartments 116, 316, 416, 516, 616, 716, and 1016 except for differences described herein) are integrated. For example, a first side of recharging unit 1182 which is configured to be oriented toward scalp 16 may contain recharge coil container 1118 and therein one of coils 80, 82, 84, 86, while the other side of recharging unit 1182 may contain power source compartment 1116 and any components stored within power source compartment 1116 (e.g., components of FIG. 5).

Wearable medical device 1100 includes securing member 1102 which is configured to extend around an entire perimeter of head 12 of the patient in a generally horizontal plane. Securing member 1102 is further configured to cross at least some of each the left anterior, right anterior, left posterior, and right posterior quadrants (FIG. 1) of scalp 16 of the patient as mounted to patient. Wearable medical device 1100 further includes flexible body rails 1110A, 1110B. Flexible body rails 1110A, 1110B may include two flexible rail that are configured to extends in an arc superior to securing member 1102 to span left and right quadrants of scalp 16 of the patient when wearable medical device 1100 is mounted to head 12. Charge units 1182 may be configured to mount to one or both of flexible body rails 1110A, 1110B.

In some examples, securing member 1102 may include one or more engagement zones 1104A, 1104B. Engagement zone 1104A, 1104B may be configured to extend along one side of head 12. For example, engagement zone 1104A extends along the left posterior and anterior quadrants of scalp 16 of the patient, while engagement zone 1104B extends along the right posterior and anterior quadrants of scalp 16 of the patient. Engagement zones may be formed by a hook and loop strip and may be configured to receive a corresponding mating hook and loop strip of flexible body rail 1110A. In this way, the patient may adjust the orientation of the span of flexible body rail 1110A, per arrow 1106. Further, a patient may slide respective charge units 1182 along a length of a respective flexible body rail 1110A, 1110B before securing charge units 1182 to the respective flexible body rail 1110A, 1110B at a location that corresponds to IMD 14 implant location.

In some examples flexible body rail 1110B may be fixedly secured to securing member 1102. For example, flexible body rail 1110B may include a first end attached to securing member 1102 at an anterior location and a second end attached to securing member 1102 at a posterior location. In this way, flexible body rail 1110B may be configured to generally aligned with the midline plane (FIG. 1) of head 12 of the patient when securing member 1102 is mounted to head 12 of the patient. In some examples both flexible body rails 1110A, 1110B may be connected at a pivot joint 1108. Pivot joint 1108 may be configured to enable flexible body rail 1110A to rotate according to arrow 1106 relative to flexible body rail 1110B. In some examples, securing member 1102 and flexible body rails 1110A, 1110B may be formed from one or more of: ABS, PVC, polycarbonate, HDPE, PEEK, PET, and polypropylene.

FIGS. 19A-19D depict conceptual diagrams illustrating various views of wearable medical device 1200, which may be substantially similar to wearable medical device 100, 300, 400, 500, 600, 700, 800, 900, 1000, and 1100 with the exception of any differences described herein. Wearable medical device 1200 may include recharging units 1282 into which recharge coil containers 1218 (which may be substantially similar to recharge coil containers 118, 318, 418, 518, 618, 718, 1018, and 1118 except for differences described herein) and power source compartment 1216 (which may be substantially similar to power source compartments 116, 316, 416, 516, 616, 716, 1016, and 1116 except for differences described herein) are integrated. For example, a first side of recharging unit 1282 which is configured to be oriented toward scalp 16 may contain recharge coil container 1218 and therein one of coils 80, 82, 84, 86, while the other side of recharging unit 1282 may contain power source compartment 1216 and any components stored within power source compartment 1216 (e.g., components of FIG. 5).

Wearable medical device 1200 includes securing member 1202 formed by a flexible headband, which, when mounted to head 12 of the patient, extends around an entire perimeter of head 12 of the patient in a generally horizontal plane along each of the left anterior, right anterior, left posterior, and right posterior quadrants (FIG. 1) of scalp 16 of the patient. Securing member 1202 may define holding features 1228 that are configured to securely receive charge units 1282. Holding features 1228 may define an aperture configured to securely receive charge unit 1282. to hold charge module 482 in an aperture thereof. Holding feature 1228 may be configured to slideably engage with securing member 1202 for movement relative thereto in the generally horizontal plane, per arrow 1204. Holding feature 1228 may be formed from a relatively hard plastic, for example, ABS, PVC, polycarbonate, HDPE, PEEK, PET, or polypropylene. Securing member headband 1202 from an elasticized material, such as a polyester/Spandex blend, and/or Lycra, and/or cotton.

FIGS. 20A-20H depict conceptual diagrams illustrating various views of wearable medical device 1300, which may be substantially similar to wearable medical device 100, 300, 400, 500, 600, 700, 800, 900, 1000, 1100, and 1200 with the exception of any differences described herein. Wearable medical device 1300 includes securing member 1302 formed by a flexible headband, which, when mounted to head 12 of the patient, extends around an entire perimeter of head 12 of the patient in a generally horizontal plane along each of the left anterior, right anterior, left posterior, and right posterior quadrants (FIG. 1) of scalp 16 of the patient. Wearable medical device 1300 includes flexible body 1310 that includes one or more resilient bands. Recharging coils 80, 82, 84, 86, and/or recharging units may be mounted to bands of flexible body 1310. The bulk of band of flexible body 1310 may be pre-formed in an arc to span left and right quadrants of scalp 16 of the patient, or anterior and posterior quadrants of scalp 16 of the patient. Flexible body 1310 may be formed from ABS, PVC, polycarbonate, HDPE, PEEK, PET, or polypropylene.

Bands of flexible body 1310 may be movable relative to securing member 1302. For example, each of first and second ends 1302-1, 1302-2 of each band of flexible body 1310 may be releasably secured to securing member 1302 via one or more engagement features 1304 of securing member 1302. For example, engagement features 1304 may include a recess defined on an internal surface of securing member 1302 that may receive protrusions of first and second ends 1302-1, 1302-2, for example, via a snap fit. Securing member 1302 may include a plurality of engagement features 1304 generally evenly dispersed all along securing member 1302 (and therein dispersed across all quadrants of scalp 16 when charging device 1300 is mounted on head 12).

In some examples, flexible body 1310 may include two or more bands that are configured to extend between securing member 1302. For example, as depicted in FIG. 20A, wearable medical device 1300 includes first rail of flexible body 1310A and second rail of flexible body 1310B. In such examples, one rail of flexible body 1310A may be configured to be moved relative to securing member 1302, while the other rail of flexible body 1310B may be configured to be relative stationary relative to securing member 1302. For example, stationary band of flexible body 1310B may extends in an arc from a first end attached to securing member 1302 at an anterior location to a second end attached to securing member 1302 at a posterior location. In this way, an arc of relatively stationary band of flexible body 1310B may be generally aligned with the midline plane of head 12 (FIG. 1) when securing member 1302 is mounted to head 12 of the patient. Similarly, in some examples, as depicted in FIG. 20D, wearable medical device 1300 may include one relatively stationary band of flexible body 1310B along with two moveable bands of flexible body 1310A, 1310C.

FIGS. 21A-21F depict conceptual diagrams illustrating various views of wearable medical device 1400, which may be substantially similar to recharging device 100, 300, 400, 500, 600, 700, 800, 900, 1000, 1100, 1200 and 1300 with the exception of any differences described herein. Wearable medical device 1400 includes securing member 1402 formed by a flexible headband, which, when mounted to head 12 of the patient, extends around an entire perimeter of head 12 of the patient in a generally horizontal plane along each of the left anterior, right anterior, left posterior, and right posterior quadrants (FIG. 1) of scalp 16 of the patient. Wearable medical device 1400 includes flexible body 1410 that includes one or more resilient bands. Recharging coils 80, 82, 84, 86, and/or recharging units may be mounted to bands of flexible body 1410. The bulk of band of flexible body 1410 may be pre-formed in an arc to span left and right quadrants of scalp 16 of the patient, or anterior and posterior quadrants of scalp 16 of the patient. Flexible body 1410 may be formed from ABS, PVC, polycarbonate, HDPE, PEEK, PET, or polypropylene.

Bands of flexible body 1410 may be movable relative to securing member 1402. For example, each of first and second ends 1402-1, 1402-2 of each band of flexible body 1410 may be releasably secured to securing member 1402 via one or more engagement features 1404 of securing member 1402. For example, engagement features 1404 may include a recess defined on an internal surface of securing member 1402 that may receive protrusions 1406 of first and second ends 1402-1, 1402-2, for example, via a snap fit. Securing member 1402 may include a plurality of engagement features 1404 generally evenly dispersed all along securing member 1402 (and therein dispersed across all quadrants of scalp 16 when wearable medical device 1400 is mounted on head 12).

Flexible body 1410 may include two or more bands that are configured to extend between securing member 1402. Rail of flexible body 1410A may be configured to be secured to securing member 1402 at a plurality of locations such that rail of flexible body 1410A may functionally be moved relative to securing member 1402. Similarly, the other rail of flexible body 1410B may be configured to be secured to securing member 1402 at only one or relatively fewer locations along securing member 1302. Bands of flexible body 1410 may be secured together by a pivot joint 1408, so that bands of flexible body 1410 can be rotated relative to one another, per arrows 1412. For example, stationary band of flexible body 1410B may be configured to only be secured to securing member 1402 such that stationary band of flexible body 1410B extends in an arc from a first end attached to securing member 1402 at an anterior location to a second end attached to securing member 1402 at a posterior location (e.g., to be generally aligned with the midline plane of head as depicted in FIG. 21C). In other examples, all or many rails of flexible body 1410 are configured to be secured to securing member 1402 at a plurality of locations, similar to band of flexible body 1410A. Securing member 1402 may be formed from an elasticized material, such as a polyester/Spandex blend, and/or Lycra, and/or cotton.

FIGS. 22A-22C depict conceptual diagrams illustrating various views of wearable medical device 1500, which may be substantially similar to wearable medical device 100, 300, 400, 500, 600, 700, 800, 900, 1000, 1100, 1200, 1300, and 1400 with the exception of any differences described herein. Wearable medical device 1500 includes securing member 1502 formed by a flexible headband, which, when mounted to head 12 of the patient, extends around an entire perimeter of head 12 of the patient in a generally horizontal plane along each of the left anterior, right anterior, left posterior, and right posterior quadrants (FIG. 1) of scalp 16 of the patient. Wearable medical device 1500 includes two panels of flexible body 1510A, 1510B. Recharging coils 80, 82, 84, 86, and/or recharging units may be mounted to panels of flexible body 1510. Flexible body 1510 may be formed from ABS, PVC, polycarbonate, HDPE, PEEK, PET, or polypropylene.

Panels of flexible body 1510A, 1510B may be movable relative to securing member 1502. For example, each panel of flexible body 1510 may be configured to move per arrow 1504 to approach or move away from midline 1506. Panels of flexible body 1410 may be relatively stiff, such that once moved to a position relative to midline 1506 the panels of flexible body may stay in their relative position as mounted on head 14. Securing member 1402 may be formed from an elasticized material, such as a polyester/Spandex blend, and/or Lycra, and/or cotton.

FIGS. 23A-23D depict conceptual diagrams illustrating various views of wearable medical device 1600, which may be substantially similar to wearable medical device 100, 300, 400, 500, 600, 700, 800, 900, 1000, 1100, 1200, 1300, 1400, and 1500 with the exception of any differences described herein. Wearable medical device 1600 includes a securing member 1602 for mounting to head 12 of the patient on an exterior side of scalp 16. Securing member 1602 includes resilient band 1602A and ear hook 1602B attached to a first end of band 1602A.

Wearable medical device 1600 further includes conformable member 1604. Conformable member 1604 may include one or more charging coil 80, 82, 84, 86, as well as one or more components of power source compartment (e.g., components of FIG. 5). Conformable member 1604 may be attached to second end of securing member band 1602A. In some examples, conformable member 1604 may be configured to at least one of the quadrants of scalp 16 of the patient when securing member 1602 is mounted to head 12 of the patient.

In some examples, securing member band 1602A is movable relative to ear hook 1602B. In this way, securing member band 1602A may be moved relative to scalp 16 in order to move conformable member 1604 relative to scalp 16. In some examples, securing member band 1604 may extend at least partially over head 12 of the patient in an arc along a generally vertical plane with an inward tension to generally conform and fit snug to the exterior side of scalp 16 when securing member 1602 is mounted to head 12.

FIGS. 24A-24D depict conceptual diagrams illustrating various views of wearable medical device 1700, which may be substantially similar to wearable medical device 100, 300, 400, 500, 600, 700, 800, 900, 1000, 1100, 1200, 1300, 1400, 1500, and 1600 with the exception of any differences described herein. Wearable medical device 1700 may include securing members 1702A, 1702B, 1702C (collectively "securing members 1702"). Securing members 1702 may be joined together at pivot junction 1704. Recharging coils 80, 82, 84, 86 and/or charge units may be secured to securing members 1702. Securing members 1702 may be predominantly formed from one or more of ABS, PVC, polycarbonate, HDPE, PEEK, PET, polypropylene, silicone rubber, and thermoplastic elastomer.

In some examples, each of securing members 1702 may be movable and conformable to any one the quadrants of scalp 16 of the patient. For example, pivot joint 1704 may be configured to rest on a top portion of head 12 when wearable medical device 1700 is mounted to head 12, after which each of securing members 1702 may be configured to extend down one side of head 12 in an arc along a generally vertical plane. In this way, securing members 1702 may secure wearable medical device 1700 to head 12 of the patient. Further, as a result of pivot joint 1704 enabling securing members 1702 to move relative to one another, a wearable medical device 1700 may be adjusted to position one or more recharging coils at each of the location(s) corresponding to the IMD 14 implant site(s).

FIGS. 25A-25H depict conceptual diagrams illustrating various views of wearable medical device 1800, which may be substantially similar to wearable medical device 100, 300, 400, 500, 600, 700, 800, 900, 1000, 1100, 1200, 1300, 1400, 1500, 1600, and 1700 with the exception of any differences described herein. Wearable medical device 1800 may include securing members 1802A, 1802B (collectively, "securing members 1802"). Each of securing members 1802 may have two ends, and each end may be secured to another end of another securing member 1802 pivot junction 1804. Recharging coils 80, 82, 84, 86 and/or components of charge units (e.g., as depicted in FIG. 5) may be secured to or housed within securing members 1802. In some examples, each securing member 1802 that includes a recharging coil may also include some or all components of a control unit integrated into the respective securing member 1802. In other examples, one control unit may control multiple coils integrated into or otherwise secured to multiple securing members 1802. Securing members 1802 may be predominantly formed from one or more of ABS, PVC, polycarbonate, HDPE, PEEK, PET, and polypropylene.

In some examples, each of securing members 1802 may be movable and conformable to any one the quadrants of scalp 16 of the patient. For example, pivot joint 1804 may be configured to be located near ears of head 12 of patient, while securing members 1802 extend over head 12 of the patient in an arc along a generally horizontal plane to secure wearable medical device 1800 to head 12 of the patient. The patient may move securing members 1802 relative to one another, per arrow 1806, to adjust locations of the recharging coils thereof to correspond with implant sites. In some examples, flexible housing 1810 may extend between securing members 1802 as securing members 1802 flex along arrow 1806. Flexible housing 1810 may define an accordion structure that compresses and expands in response to the flexure of securing members 1802.

Figure 26B:
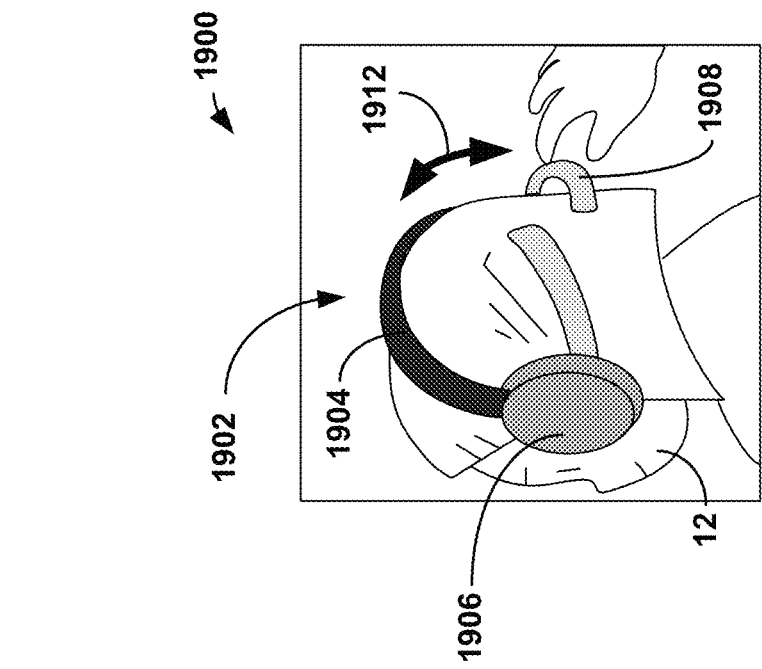
FIGS. 26A and 26B are conceptual diagrams illustrating an example wearable medical device that may be used to recharge a power source of the IMD of FIG. 1A.
Figure 26A:
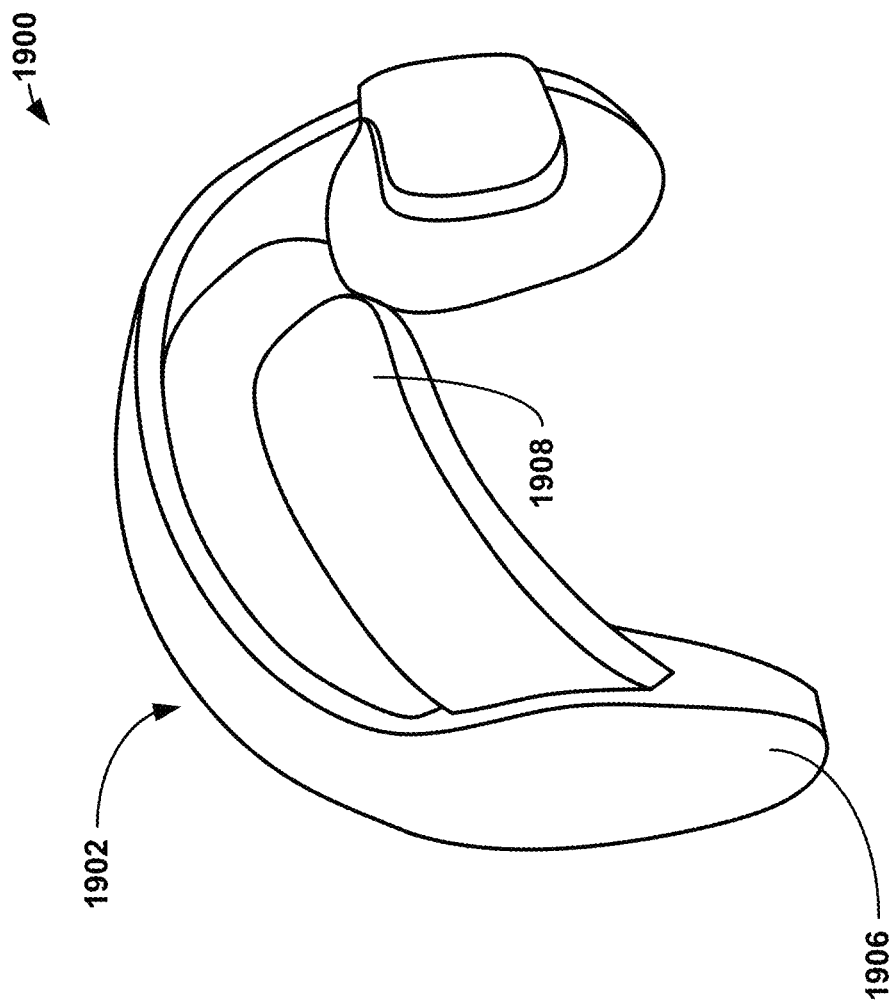
Figure 27C:
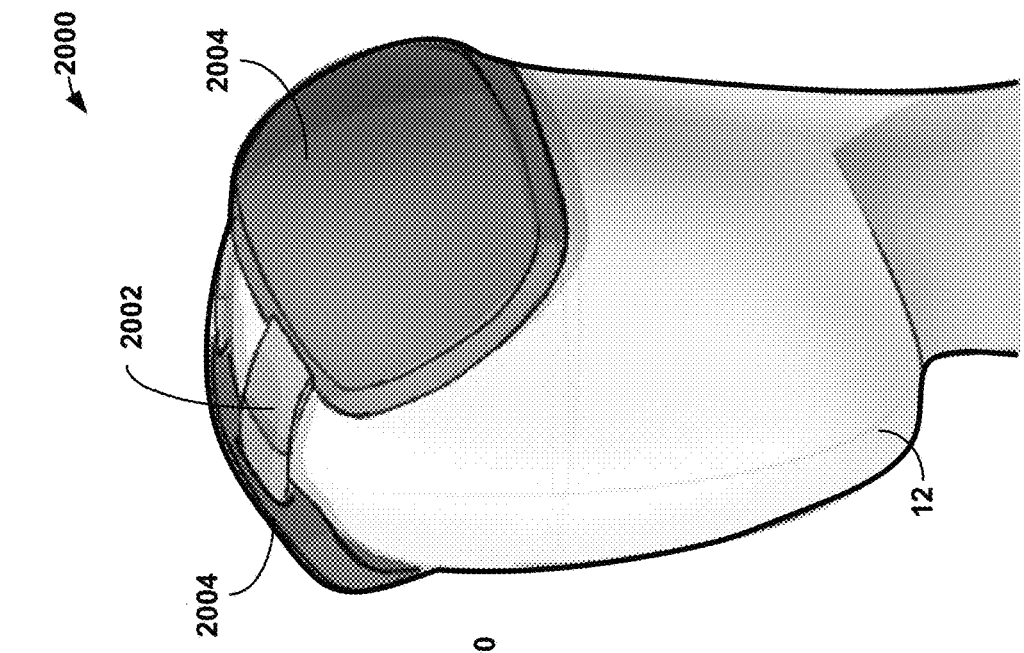
FIGS. 27A, 27B, 27C, and 27D are conceptual diagrams illustrating an example wearable medical device that may be used to recharge a power source of the IMD of FIG. 1A.
Figure 27B:
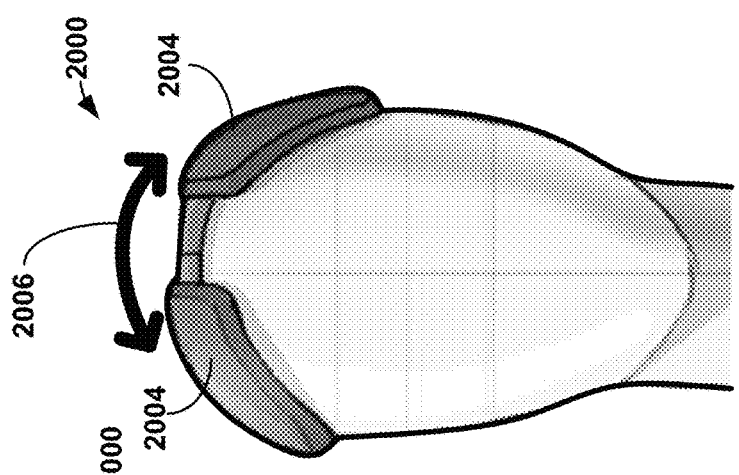
Figure 27D:
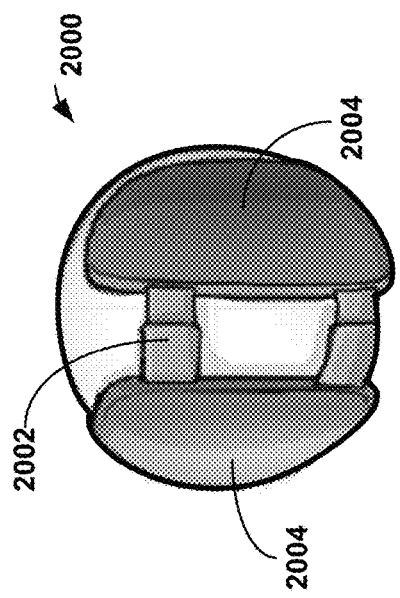
Figure 27A:
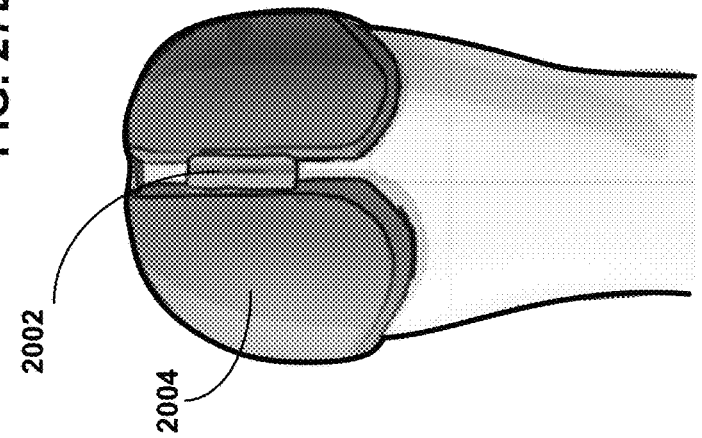

FIGS. 26A-26B depict conceptual diagrams illustrating various views of wearable medical device 1900, which may be substantially similar to recharging device 100, 300, 400, 500, 600, 700, 800, 900, 1000, 1100, 1200, 1300, 1400, 1500, 1600, 1700, and 1800 with the exception of any differences described herein. Wearable medical device 1900 may include securing member 1902. Securing member 1902 may include resilient band 1904 and a pair of terminating pads 1906 secured to each end of resilient band 1904. Pads 1906 are configured to press against ears of head 12 while resilient band 1904 extends over head 12. Wearable medical device 1900 may include conformable members 1908 that extend from pads 1906. Conformable members 1908 may be attached to securing member 1902 via a hidden internal pivot joint that enables conformable members 1908 to pivot relative to pads 1906. Conformable members 1908 may be secured to pads 1906 such that conformable members 1908 extending in an arc away from pads 1906. For example, one of the conformable members 1908 may define an arc range that spans the right posterior quadrant of scalp 16 of the patient, and the other of the conformable members 1908 defines an arc range that spans the left posterior quadrant of scalp 16 of the patient.

Recharging coils 80, 82, 84, 86 and/or components of charge units (e.g., as depicted in FIG. 5) may be secured to or housed within conformable members 1908. In some examples, each of conformable member 1908 may include both a recharging coil and also some or all components of a charge unit in the respective conformable member 1908. In other examples, one charge unit may control multiple coils integrated into or otherwise secured to multiple conformable members 1908. In some examples, conformable members may predominantly be formed from one or more of ABS, PVC, polycarbonate, HDPE, PEEK, PET, polypropylene, silicone rubber, and thermoplastic elastomer.

FIGS. 27A-27D depict conceptual diagrams illustrating various views of wearable medical device 2000, which may be substantially similar to wearable medical device 100, 300, 400, 500, 600, 700, 800, 900, 1000, 1100, 1200, 1300, 1400, 1500, 1600, 1700, 1800, and 1900 with the exception of any differences described herein. Wearable medical device 2000 may include two conformable members 2004 attached to opposite ends of two securing members 2002. Securing members 2002 may each include adjustable resilient bands that are configured to allow movement of conformable members 2004 relative thereto, per arrow 2006. As depicted, securing member 2002 are configured to extend in an arc in a generally vertical plane are shown over head 12 when mounted to head 12 of the patient. Further, when wearable medical device 2000 is mounted to head 12, one of conformable members 2004 is configured to conform to one or both right quadrants of scalp 16 of the patient, while the other of conformable members 2004 is configured to conform to one of both left quadrants of scalp 16 of the patient.

In some examples, each conformable member 2004 is relatively flexible and cushioned. For example, each of conformable members 2004 may be formed from a silicone rubber or a thermoplastic elastomer. Conformable members 2004 may define a pocket between inner and outer layers thereof. This pocket defined by each of conformable members 2004 may be configured to hold one or more recharging coils therein, for example, any of the above described components of control unit (e.g., as in FIG. 5).

FIGS. 28A-28E depict conceptual diagrams illustrating various views of wearable medical device 2100, which may be substantially similar to wearable medical device 100, 300, 400, 500, 600, 700, 800, 900, 1000, 1100, 1200, 1300, 1400, 1500, 1600, 1700, 1800, 1900, and 2000 with the exception of any differences described herein. Wearable medical device 2100 may include a plurality of recharging coils 80, 82, 84, 86 mounted between inner and outer layers of a covering that is sized to cover a portion of each quadrants of scalp 16. Wearable medical device 2100 may include securing member 2102, which may itself include a stretchable cap. Securing member 2102 may be made of Neoprene or the like. Flexible body 2110 may extend out away from securing member 2102 to define a plurality of pockets. For example, securing member 2102 may substantially extend across most or all of scalp 16, substantially contacting and conforming to scalp 16 as securing member 2102 does so. Flexible body 2110 may extend radially away from securing member 2102 to define pockets between itself and securing member 2102.

One or more pockets as created by securing member 2102 and flexible body 2110 may be configured to hold coils 80, 82, 84, 86 and or recharging components (e.g., as in FIG. 5). Each pocket as defined by securing member 2102 and flexible body 2110 may be centered over a different quadrant (LAQ, RAQ, RPQ, LPQ) of scalp 16, substantially covering that quadrant. is shown located for coverage of each quadrant.

Wearable medical device 2100 may include including docking fob 2104 that is configured for attachment of electronic charging unit 2182. Charging unit 2182 may include circuitry configured to control charging coils, such as circuitry and components of FIG. 5. Once attached to docking fob 2104, charging unit 2182 may be electrically coupled with each recharging coil secured within pockets defined by securing member 2102 and flexible body 2110. control unit 2185 thereto for coupling with the recharging coils of headgear 910.

FIGS. 29A-29E depict conceptual diagrams illustrating various views of wearable medical device 2200, which may be substantially similar to wearable medical device 100, 300, 400, 500, 600, 700, 800, 900, 1000, 1100, 1200, 1300, 1400, 1500, 1600, 1700, 1800, 1900, 2000, and 2100 with the exception of any differences described herein. Wearable medical device 2200 may include a plurality of recharging coils 80, 82, 84, 86 mounted between inner and outer layers of a covering that is sized to cover a portion of each quadrants of scalp 16. Wearable medical device 2200 may include securing member 2202, which may itself include a helmet in which recharging coils 80, 82, 84, 86 are embedded and to which an electronic recharge control unit 2282 is mounted. Electrical recharge control unit 2282 may include components of a power source compartment as described herein (e.g., as depicted in FIG. 5). Securing member 2202 may be formed from one of more of ABS, PVC, polycarbonate, HDPE, PEEK, PET, polypropylene, silicone rubber, and thermoplastic elastomer.

Wearable medical device 2200 may include size adjustment member 2204. Size adjustment member 2204 may be configured to modify an internal size of securing member 2202 using a mechanism such as a twist mechanism. Size adjustment member 2204 may be secured to wearable medical device 2200 at a posterior inferior edge of securing member 2202. In some examples, recharge control unit 2282 may be configured to detect the location of one or more cranially mounted IMDs 14. In response to detecting a location of IMDs 14, control unit 2282 may identify and activate (e.g., send current to) recharging coils that are aligned with these IMDS 14.

FIGS. 30A-30D depict conceptual diagrams illustrating various views of wearable medical device 2300, which may be substantially similar to wearable medical device 100, 300, 400, 500, 600, 700, 800, 900, 1000, 1100, 1200, 1300, 1400, 1500, 1600, 1700, 1800, 1900, 2000, 2100, and 2200 with the exception of any differences described herein. Wearable medical device 2300 may include securing member 2302, which may be include a cap configured to reach down to a neck of the patient. Securing member 2302 may be configured to integrate recharging coils 80, 82, 84, 86, between an inner and outer layer of securing member 2302. In some examples, securing member 2302 may include a plurality of charging coils embedded across securing member 2302, such that charging coils would be distributed among all quadrants of scalp 16 when wearable medical device 2300 is mounted to head 12 of patient.

Wearable medical device 2300 may include collar member 2304 secured to securing member 2302. Collar member 2304 may be attached to a posterior inferior edge of securing member 2302. Collar member 2304 may contain an electronic recharge control unit that contains components configured to control recharging coils (e.g., components of FIG. 5). Securing member 2302 may be formed from one or more of polyester, Spandex, cotton, and Lycra.

Figure 31A:
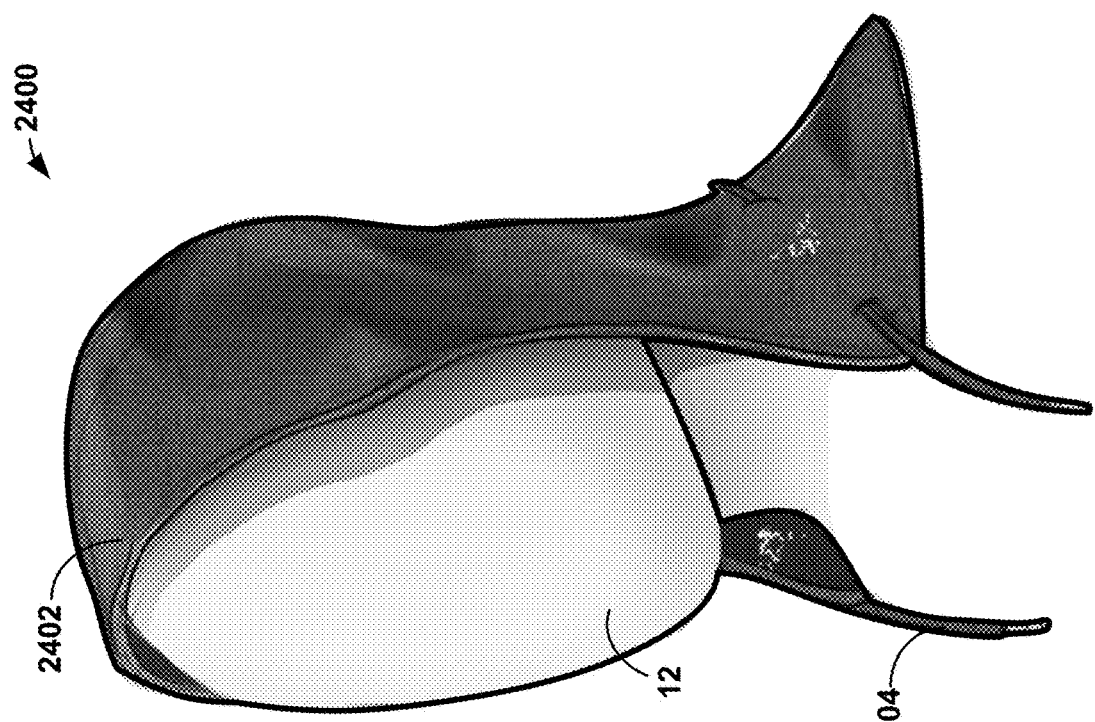
FIGS. 31A, 31B, and 31C are conceptual diagrams illustrating an example wearable medical device that may be used to recharge a power source of the IMD of FIG. 1A.
Figure 31B:
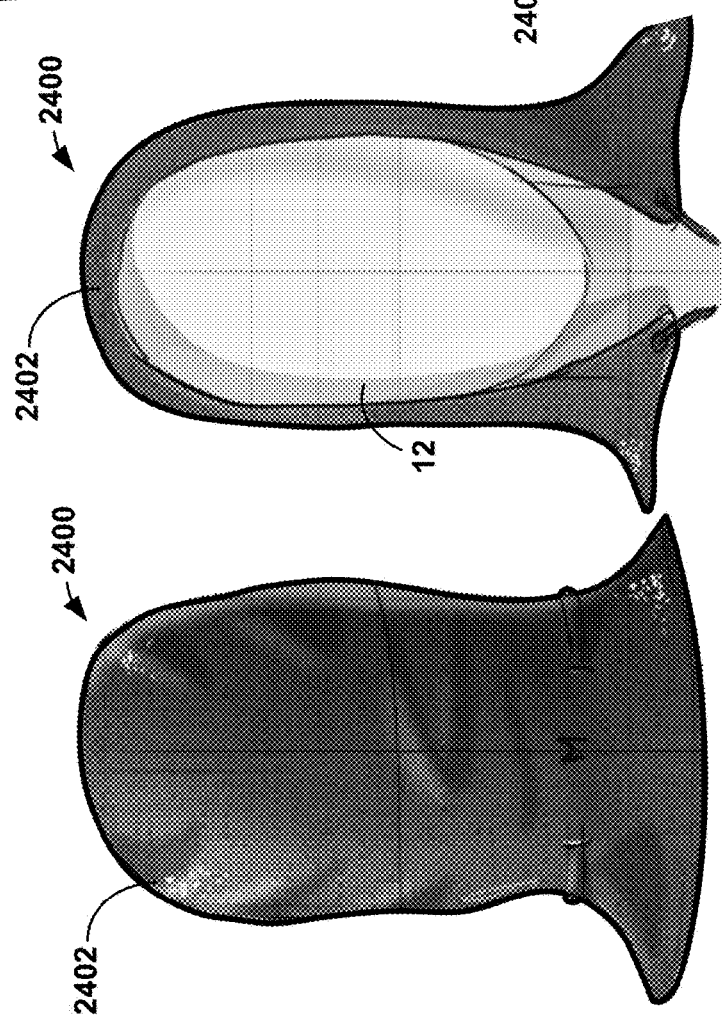
Figure 31C:
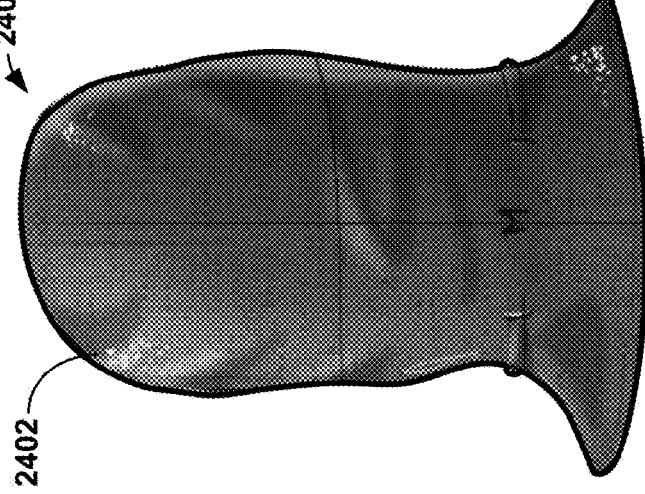
Figure 32B:
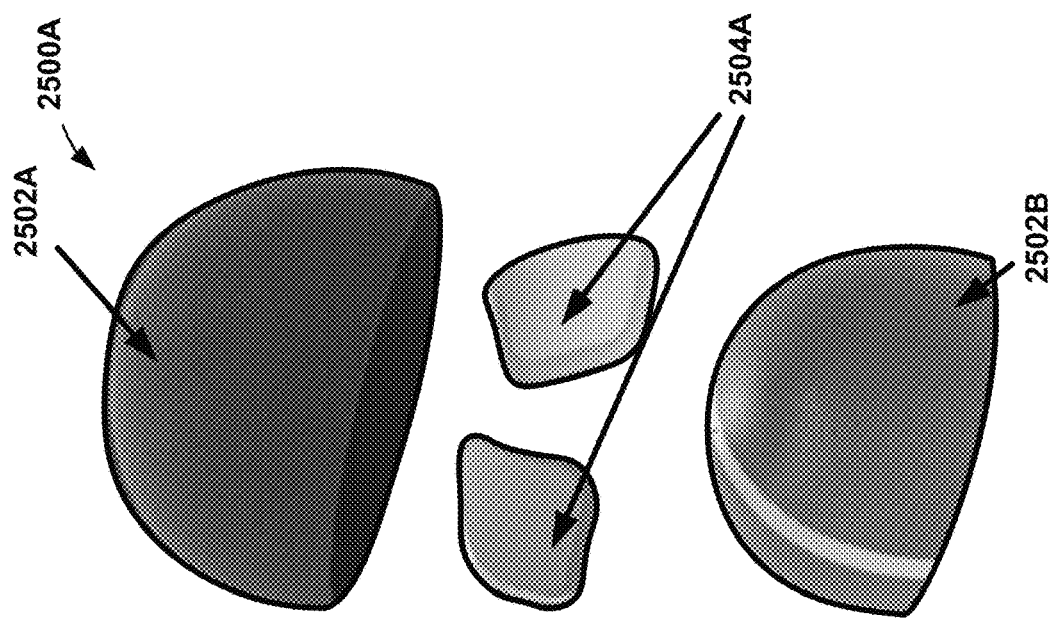
FIGS. 32A and 32B are conceptual diagrams illustrating a first and second example recharge module that may be used with any of the example wearable medical devices of FIGS. 4A-31C.
Figure 32A:
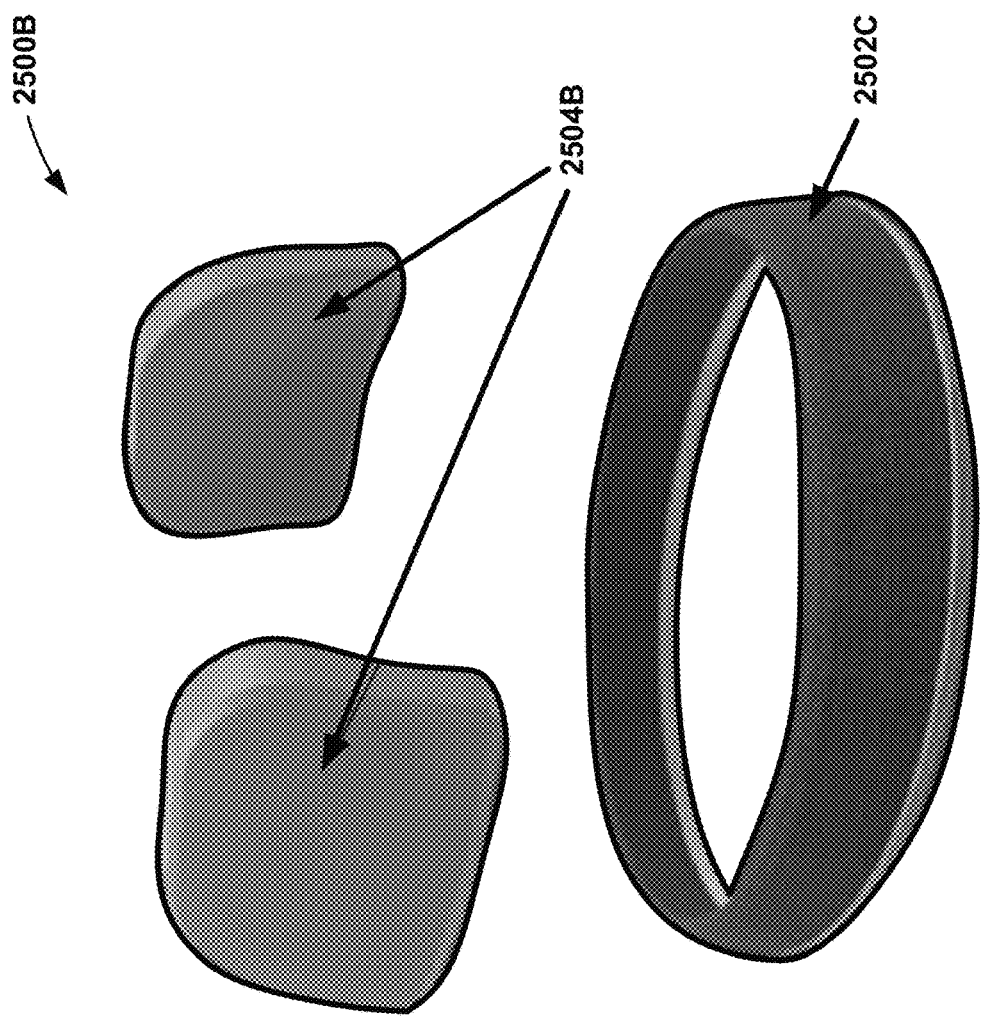

FIGS. 31A-31C depict conceptual diagrams illustrating various views of wearable medical device 2400, which may be substantially similar to recharging device 100, 300, 400, 500, 600, 700, 800, 900, 1000, 1100, 1200, 1300, 1400, 1500, 1600, 1700, 1800, 1900, 2000, 2100, 2200, and 2300 with the exception of any differences described herein. Wearable medical device 2400 may include securing member 2402, which may be include a hood configured to drape over scalp 16 and reach down to a neck of the patient. Securing member 2402 may be configured to integrate recharging coils 80, 82, 84, 86, between an inner and outer layer of securing member 2402. In some examples, securing member 2402 may include a plurality of charging coils embedded across securing member 2402, such that charging coils would be distributed among all quadrants of scalp 16 when wearable medical device 2400 is mounted to head 12 of patient.

Wearable medical device 2400 may include tassels 2404 secured to securing member 2402. Tassels 2404 may be attached near a posterior inferior edge of securing member 2402. Tassels 2404 may be configured to tighten or loosen securing member 2402. In some examples, wearable medical device 2400 may be integrated into a sweatshirt, where securing member 2402 is functionally the hood of the sweatshirt. Securing member 2402 may be formed from one or more of polyester, Spandex, cotton, and Lycra.

FIGS. 32A-34C 32B depict conceptual diagrams illustrating perspective views of recharge assemblies 2500A, 2500B, 2500C that include securing members 2502A, 2502B, 2502C, 2502D, 2502E (collectively "securing members 2502") of conformable caps 2502A, 2502B, 2502D, 2502E and elastic head band 2502C and associated charge modules 2504A, 2504B, 2504C, 2504D (collectively "charge modules 2504"). Each securing member 2502 may be formed from any of the aforementioned suitable materials and is configured to conform to at least a portion of each of a left anterior quadrant, a left posterior quadrant, a right posterior quadrant, and a right anterior quadrant of scalp 16 when the respective securing member 2502 is mounted to head 12. Further, each securing member 2502 includes attachment means distributed throughout for the attachment of one or more charge modules 2504 at or near power source compartment and relevant power source and recharging circuitry (e.g., power management circuit 162 and rechargeable power source 158 of FIG. 5) is located within securing members 2502. For example, as depicted in FIGS. 34A-34C, securing members 2502E may include Velcro near a location with the power source and power management circuit for the securing members 2502E, such that a respective charge module 2504D may be directly attached to the respective securing member 2502E. In another example as depicted in FIGS. 33A-33C, securing member 2502D may include a magnetic element configured to magnetically hold one of charging modules 2504C to a location adjacent the power source and power management circuit housing of securing member 2502D. Charging modules 2504 may work substantially similar to recharging device 103 described herein, such that charging modules 2504 may be used to recharge power sources of IMDs 14 as depicted in FIG. 33.

In the foregoing detailed description, the invention has been described with reference to specific embodiments. However, it may be appreciated that various modifications and changes can be made without departing from the scope of the invention as set forth in the appended claims. Furthermore, various combinations of elements described above in conjunction with the specific embodiments, are within the scope of the present invention, for example, according to the appended claims This disclosure is primary directed to specific systems and methods related to wearable medical devices for securing recharging coils to a head of a patient. However, one or more aspects of this disclosure may also be applicable to other types of wearable medical devices that may be secured to other areas of a patient. For example, aspects of this disclosure may be applicable to a sleeve that may be used to secure one or more charging coils at one or more locations that are aligned with one or more IMDs located at a patient's side, or at a subclavical location, or the like.

The following examples describe various examples and combinations contemplated and discussed herein.

Example 1

A wearable medical system comprising: a flexible body configured to cover at least a portion of each of a left anterior quadrant, a left posterior quadrant, a right posterior quadrant, and a right anterior quadrant of a scalp of a head of a patient; a securing member connected to the flexible body, the securing member configured to extend around a circumference of the head and stabilize the flexible body with respect to the scalp of the patient; and a fixation member configured to mount to a location of the flexible body, the fixation member configured to couple the flexible body to a recharge coil configured to recharge an implantable power source of a cranially-mountable implantable medical device.

Example 2

The wearable medical system of example 1, further comprising: an external power source secured to at least one of the flexible body or the securing member; the recharge coil removably secured to a first surface of the flexible body, the recharge coil configured to transmit energy from the power source to recharge the implantable power source of the cranially-mountable implantable medical device; and a cable coupling the external power source to the recharge coil.

Example 3

The wearable medical system of example 1, wherein: the fixation member is a first fixation member; the location is a first location; the recharge coil is a first recharge coil; the implantable power source is a first implantable power source; and the cranially-mountable implantable medical device is a first cranially-mounted implantable medical device, further comprising: a second fixation member configured to mount to a second location of the flexible body, the second fixation member configured to couple the flexible body to a second recharge coil configured to recharge an second implantable power source of a second cranially-mountable implantable medical device.

Example 4

The wearable medical system of example 3, further comprising: an external power source secured to at least one of the flexible body or the securing member; the first recharge coil removably secured to a first surface of the flexible body, the first recharge coil configured to transmit energy from the power source to recharge the first implantable power source of the first cranially-mountable implantable medical device; the second recharge coil removably secured to a second surface of the flexible body, the second recharge coil configured to transmit energy from the power source to recharge the second implantable power source of the second cranially-mountable implantable medical device; and one or more cables configured to couple the external power source to the first and second recharge coils.

Example 5

The wearable medical system of either example 3 or 4, wherein the first recharge coil and the second recharge coil are configured to simultaneously transmit energy from the power source to recharge both the implantable power source of the first cranially-mountable implantable medical device and the second implantable power source of the second cranially-mountable implantable medical device.

Example 6

The wearable medical system of any of examples 3-5, wherein: the first fixation member is secured to the first surface of the flexible body at a third location adjacent the first location such that the first recharge coil will be aligned with a first implanted recharge coil of the first cranially-mountable implantable medical system when coupled to the first fixation member; and the second fixation member is secured to the first surface of the flexible body at a fourth location adjacent the second location such that the second recharge coils will be aligned with a second implanted recharge coil of the second cranially-mountable implantable medical system when coupled to the second fixation member.

Example 7

The wearable medical system of any of examples 3-5, wherein: the flexible body comprises a map identifying a plurality of locations; both the first location and the second location are in the plurality of locations; the first recharge coil includes a first identifying that identifies the first location; and the second recharge coil includes a second identifying that identifies the second location.

Example 8

The wearable medical system of any of examples 3-7, wherein the one or more cables are removably couplable to the first and second recharge coils.

Example 9

The wearable medical system of example 1, further comprising: a first external power source secured to at least one of the flexible body or the securing member; the first recharge coil removably secured to a first surface of the flexible body, the first recharge coil configured to transmit energy from the first power source to recharge the first implantable power source of the first cranially-mountable implantable medical device; a second external power source secured to at least one of the flexible body or the securing member; the second recharge coil removably secured to a second surface of the flexible body, the second recharge coil configured to transmit energy from the second power source to recharge the second implantable power source of the second cranially-mountable implantable medical device.

Example 10

The wearable medical system of any of examples 1-9, wherein the securing member comprises a band that is relatively more rigid than the flexible body.

Example 11

The wearable medical system of any of examples 1-10, wherein the flexible body comprises a map identifying a plurality of locations, wherein the location is one of the plurality of locations.

Example 12

The wearable medical system of any of examples 1-11, further comprising a bill that is configured to extend radially out from the flexible body, wherein the bill is connected to the flexible body along at least a portion of the left anterior quadrant and the right anterior quadrant.

Example 13

The wearable medical system of any of examples 1-12, wherein the flexible body includes at least two seams that are configured to secure a shape of the flexible body when covering at least a portion of the scalp by extending substantially straight across the flexible body between the securing member, wherein a first seam of the least two seams extends from the left anterior quadrant to the right posterior quadrant and a second seam of the least two seams extends from the right anterior quadrant to the left posterior quadrant.

Example 14

The wearable medical system of any of examples 1-13, wherein the securing member comprises an adjustable mechanism configured to adjust a circumference of the securing member.

Example 15

The wearable medical system of example 14, wherein the securing member comprises a click wheel configured to increase the circumference of the securing member when the click wheel is turned in a first direction and configured to decrease the circumference when the click wheel is turned in a second direction opposite the first direction.

Example 16

The wearable medical system of example 15, wherein the securing member includes a band with overlapping ends, wherein an adjustable amount of overlap between the overlapping ends defines the circumference of the securing member.

Example 17

The wearable medical system of any of examples 1-16, wherein the power source comprises an attachment mechanism configured to attach the power source to the securing member adjacent the left posterior quadrant and the right posterior quadrant.

Example 18

The wearable medical system of any of examples 1-17, further comprising a curved housing configured to house the external power source, wherein the curved housing defines a first main surface configured to interface with the scalp and a second main surface that is on an opposite side of the curved housing of the first main surface, where the first main surface and the second main surface define substantially similar curvatures that approximate a curvature of a back of the head of the patient.

Example 19

The wearable medical system of any of examples 1-18, further comprising a curved container that is configured to house the recharge coil, wherein the curved container defines a concave main surface that approximates a curvature of the scalp of the patient and is configured to interface with the scalp of the patient.

Example 20

The wearable medical system of example 19, wherein the main surface is a first main surface, wherein the curved container defines a second main surface that is on an opposite side of the curved container of the first main surface and approximates the curvature of the scalp of the patient, wherein the second main surface defines a ridge that extends out away from the second main surface, wherein the flexible body includes a first surface configured to contact the scalp and a second surface that is on an opposite side of the flexible body relative to the first surface, wherein the fixation member includes: an attachment assembly for securing the curved housing for the recharge coil to the flexible body, the attachment assembly including: a bracket defining a recess and a channel configured to receive the ridge of the second main surface to securely attach the bracket to the curved container; and a pin configured to extend through a hole in the flexible body from the second surface of the flexible body past the first surface of the flexible body into the recess of the bracket to be securely received by the bracket, the pin including a plate configured to press against the second surface of the flexible body when the pin is received by the recess of the bracket.

Example 21

The wearable medical system of example 20, wherein the curved container includes a bore that extends through the curved container and is centered within the ridge, wherein the bore is configured to receive the recess of the bracket when the bracket is securely attached to the curved container, where the bore is configured to accept a marking pen to enable positioning of the curved housing over the cranially-mountable implantable medical device to visibly mark the location on the first main surface flexible body.

Example 22

The wearable medical system of either example 20 or 21, further comprising a piercing element configured to be removably coupled to the pin, the piercing element including a piercing tip configured to pierce the flexible body from the first surface through to the second surface to create the hole in the flexible body.

Example 23

A wearable medical system, comprising: a flexible body configured to cover at least a portion of each of a left anterior quadrant, a left posterior quadrant, a right posterior quadrant, and a right anterior quadrant of a scalp of a head of a patient; a securing member connected to the flexible body, the securing member configured to extend around a circumference of the head and stabilize the flexible body with respect to the scalp of the patient; an external power source secured to at least one of the flexible body or the securing member; a first recharge coil removably configured to transmit energy from the power source to recharge a first implantable power source of a first cranially-mountable implantable medical device; a second recharge coil removably configured to transmit energy from the power source to recharge a second implantable power source of a second cranially-mountable implantable medical device; one or more cables coupling the external power source to the first and second recharge coils; a first fixation member configured to mount to a first location of the flexible body, the first fixation member configured to securely attach the first recharge coil to the flexible body; and a second fixation member configured to mount to a second location of the flexible body, the second fixation member configured to securely attach the second recharge coil to the flexible body.

Example 24

The wearable medical system of example 23, wherein the securing member comprises a band that is relatively more rigid than the flexible body.

Example 25

The wearable medical system of either example 23 or 24, wherein the flexible body comprises a map identifying a plurality of locations, wherein the location is one of the plurality of locations.

Example 26

The wearable medical system of any of examples 23-25, further comprising a bill that is configured to extend radially out from the flexible body, wherein the bill is connected to the flexible body along at least a portion of the left anterior quadrant and the right anterior quadrant.

Example 27

The wearable medical system of any of examples 23-26, wherein the flexible body includes at least two seams that are configured to secure a shape of the flexible body when covering at least a portion of the scalp by extending substantially straight across the flexible body between the securing member, wherein a first seam of the least two seams extends from the left anterior quadrant to the right posterior quadrant and a second seam of the least two seams extends from the right anterior quadrant to the left posterior quadrant.

Example 28

The wearable medical system of any of examples 23-27, wherein the securing member comprises an adjustable mechanism configured to adjust a circumference of the securing member.

Example 29

The wearable medical system of any of examples 23-28, further comprising a curved housing configured to house the external power source, wherein the curved housing defines a first main surface configured to interface with the scalp and a second main surface that is on an opposite side of the curved housing of the first main surface, where the first main surface and the second main surface define substantially similar curvatures that approximate a curvature of the scalp of the patient.

Example 30

The wearable medical system of any of examples 23-29, further comprising a first and second curved container that are configured to house the first and second recharge coils, wherein each of the first and second curved containers defined a concave first main surface that approximates a curvature of the scalp and a second main surface that approximates a curvature of the scalp, the first main surface configured to interface with the scalp of the patient and the second main surface on an opposite side of the respective curved container of the first main surface, wherein the second main surface defines a ridge that extends out away from the second main surface, wherein the flexible body includes a first surface configured to contact the scalp and a second surface that is on an opposite side of the flexible body relative to the first surface, the wearable medical system further comprising: a first and second attachment assembly for securing the first and second curved housing for the first and second recharge coil to the flexible body, each attachment assembly including: a bracket defining a recess and a channel configured to receive the ridge of the second main surface to securely attach the bracket to the curved container; and a pin configured to extend through a hole in the flexible body from the second surface of the flexible body past the first surface of the flexible body into the recess of the bracket to be securely received by the bracket, the pin including a plate configured to press against the second surface of the flexible body when the pin is received by the recess of the bracket.

Example 31

A wearable medical system, comprising: a curved container that is configured to house a recharge coil and defines a concave first main surface and a convex second main surface that each approximate a curvature of a scalp of a head of a patient, the first main surface configured to interface with the scalp of the patient and the second main surface is on an opposite side of the curved container of the first main surface, wherein the second main surface defines a ridge that extends out away from the second main surface and a bore that extends through the curved container; a bracket defining a cylindrical recess configured to be received by the bore and a channel that is configured to receive the ridge of the second main surface to securely attach the bracket to the curved container; and a pin configured to extend into the cylindrical recess of the bracket to be securely received by the bracket, the pin including a plate configured to press a mouth of the cylindrical recess when the pin is received by the recess of the bracket.

Example 32

The wearable medical device of example 31, further comprising a recharge coil housed within the curved container that is configured to transmit energy to recharge an implantable power source of a cranially-mountable implantable medical device.

Example 33

The wearable medical device of example 32, further comprising: a curved housing configured to house an external power source, wherein the curved housing defines a first main surface configured to interface with the scalp and a second main surface that is on an opposite side of the curved housing of the first main surface, where the first main surface and the second main surface define substantially similar curvatures that approximate a curvature of the scalp of the patient; and a cable coupling the external power source to the recharge coil.

Example 34

The wearable medical device of example 33, further comprising processing circuitry configured to cause the recharge coil to transmit energy from the external power source to recharge the implantable power source of the cranially-mountable implantable medical device.

Example 35

The wearable medical device of example 31, wherein the curved container is a first curved container and the bracket is a first bracket and the pin is a first pin, further comprising: a second curved container that is substantially similar to the first curved container; a second bracket that is substantially similar to the first bracket; a second pin that is substantially similar to the first pin; a first recharge coil housed within the first curved container that is configured to transmit energy to recharge a first implantable power source of a first cranially-mountable implantable medical device; a second recharge coil housed within the second curved container that is configured to transmit energy to recharge a second implantable power source of a second cranially-mountable implantable medical device; a curved housing configured to house an external power source, wherein the curved housing defines a first main surface configured to interface with the scalp and a second main surface that is on an opposite side of the curved housing of the first main surface, where the first main surface and the second main surface define substantially similar curvatures that approximate a curvature of the scalp of the patient; and one or more cables coupling the external power source to the first and second recharge coils.

Example 36

The wearable medical device of example 35, further comprising processing circuitry configured to cause the first and second recharge coils to transmit energy from the external power source to recharge the first and second implantable power sources of the first and second cranially-mountable implantable medical devices.

Example 37

The wearable medical device of any of examples 1-35, further comprising telemetry circuitry configured to communicate with the cranially-mountable implantable medical device.

Example 38

A method of securing recharge coils at a location of the wearable medical devices of any of examples 1-37 according to the methods described herein.

Example 39

A method of assembling any of the wearable medical device of any of examples 1-37.

Example 40

A method of charging implantable power sources of one or more implantable medical devices using the wearable medical device of any of examples 1-37.

Example 41

Headgear for one or more recharging coils of an implantable medical system, the system comprising a power module, a control module, a recharge module, and a housing that contains all the modules, the housing being configured for implantation beneath a scalp of the patient, and the headgear comprising: a securing member for mounting to head of the patient, on an exterior side of the scalp, the securing member being configured to extend around the head, in a generally horizontal plane, and along each of a left anterior quadrant, a left posterior quadrant, a right posterior quadrant, and a right anterior quadrant of the scalp, and to generally conform to the exterior side of the scalp, when mounted to the head; and a plurality of holding features attached to the securing member, a first holding feature of the plurality being located along one or both of the left quadrants of the scalp, when the securing member is mounted to the head, and a second holding feature of the plurality being located along one or both of the right quadrants of the scalp when the securing member is mounted to the head, and each holding feature being configured to hold a recharging coil.

Example 42

The headgear of example 41, wherein: the securing member comprises a flexible cap having an inner layer, an outer layer; and each holding feature of the plurality comprises a pocket formed between the inner layer and outer layer of the cap.

Example 43

The headgear of example 42, wherein one or both of the inner and outer layers of the cap comprise a latticework of flexible strips.

Example 44

The headgear of any of examples 1-43, wherein the securing member comprises an inner layer and an outer layer; and each holding feature comprises a pocket between the inner layer and the outer layer.

Example 45

The headgear of any of examples 1-44, wherein: the securing member comprises a cap, and each holding feature comprises a recess formed in an outer surface of the cap.

Example 46

The headgear of any of examples 1-45, wherein: the securing member comprises a flexible cap divided into a left portion and a right portion, the left portion being conformable to the left anterior and posterior quadrants of the scalp, the right portion being conformable to the right anterior and posterior quadrants of the scalp, the left and right portions each having an inner layer and an outer layer, and the left and right portions each having a superior perimeter edge free to move away from and toward a midline plane of head of the patient, when the securing member is mounted to the head; and each holding feature comprises a pocket formed between the inner layer and the outer layer of the corresponding portion of the cap.

Example 47

The headgear of any of examples 1-46, wherein each holding feature comprises a flexible rail extending in an arc superior to the securing member, each rail having left and right ends attached to the securing member so that the arc of each rail spans left and right quadrants of the scalp, when the securing member is mounted to the head.

Example 48

The headgear of example 47, wherein each flexible rail is free to move in anterior and posterior directions.

Example 49

The headgear of any of examples 1-48, wherein the plurality of holding features are distributed along all of the quadrants of the scalp when the securing member is mounted to the head.

Example 50

The headgear of any of examples 1-49, further comprising: a right posterior pad and a left posterior pad, the left and right pads being attached to the securing member and extending inferior thereto, and each pad being flexible and cushioned and including an inner layer and an outer layer; and wherein each holding feature comprises a pocket formed between the inner and outer layer of one of the pads.

Example 51

A recharge assembly comprising the headgear of any of examples 41-50, and a charge module, the charge module comprising the recharging coil, an electronic recharge control unit coupled to the coil, and a housing containing the coil and control unit, the housing being configured to be held by each holding feature of the headgear.

Example 52

A recharge assembly comprising the headgear of any of examples 41-50 and a charge module, the charge module comprising the recharging coil, an electronic recharge control unit, and a lead coupling the coil to the control unit; and wherein the headgear further comprises another holding feature attached to the securing member, the other holding feature configured to hold the control unit of the charge module.

Example 53

Headgear for one or more recharging coils of an implantable medical electrical system, the system comprising a power module, a control module, a recharge module, and a housing that contains all the modules, the housing being configured for implantation beneath a scalp of the patient, and the headgear comprising: a securing member for mounting to head of the patient on an exterior side of the scalp, the securing member being configured to extend around the head, in a generally horizontal plane, and along each of a left anterior quadrant, a left posterior quadrant, a right posterior quadrant, and a right anterior quadrant of the scalp, and to generally conform to the exterior side of the scalp, when mounted to the head; and a holding feature being configured to hold an individual recharging coil and being moveably attached to the securing member for positioning in any one of the quadrants of the scalp, when the securing member is mounted to head of the patient.

Example 54

The headgear of example 53, wherein the holding feature is slideably engaged around the securing member for movement relative thereto in the generally horizontal plane.

Example 55

The headgear of either example 53 or 54, wherein: the securing member includes a left engagement zone and a right engagement zone, the left engagement zone extending along the left posterior quadrant and the left anterior quadrant of the scalp, when the securing member is mounted to head of the patient, the right engagement zone extending along the right posterior quadrant and the right anterior quadrant of the scalp, when the securing member is mounted to head of the patient; the holding feature comprises a flexible rail, the rail having a first end configured for reversible/releasable attachment anywhere along one of the securing member engagement zones, and a second end configured for reversible/releasable attachment anywhere along the other of the securing member engagement zones; and when each end of the holding feature rail is attached to the corresponding securing member engagement zone and the securing member is mounted to head of the patient, the rail extends in an arc superior to the securing member, the arc spanning left and right quadrants of the scalp.

Example 56

The headgear of example 55, wherein the holding feature is further configured to allow movement of a held recharging coil along a length thereof between the first and second ends.

Example 57

A recharge assembly comprising the headgear of any of examples 53-56, and a charge module, the charge module comprising the recharging coil, an electronic recharge control unit coupled to the coil, and a housing containing the coil and control unit, the housing being configured to be held by the holding feature of the headgear.

Example 58

Headgear for recharging an implantable medical electrical system, the system comprising a power module, a control module, a recharge module, and a housing that contains all the modules, the housing being configured for implantation beneath a scalp of the patient, and the headgear comprising: a securing member for mounting to head of the patient on an exterior side of the scalp, the securing member being configured to extend around the head, in a generally horizontal plane, and along each of a left anterior quadrant, a left posterior quadrant, a right posterior quadrant, and a right anterior quadrant of the scalp, and to generally conform to the exterior side of the scalp, when mounted to the head; and a resilient band attached to the securing member and having a recharging coil mounted therein, the band extending in an arc superior to the securing member and being moveable relative to the securing member, the arc spanning left and right quadrants of the scalp, or anterior and posterior quadrants of the scalp, when the securing member is mounted to head of the patient.

Example 59

The headgear of example 58, wherein: the securing member includes engagement features generally evenly dispersed along the left posterior quadrant, the left anterior quadrant, the right posterior quadrant and the right anterior quadrant of the scalp, when the securing member is mounted to head of the patient; and the band has a first end configured for reversible/releasable attachment with one or more of the securing member engagement features, and a second end configured for reversible/releasable attachment with another one or more the securing member engagement features.

Example 60

The headgear of example 58, wherein the band spans anterior and posterior quadrants of the scalp, when the securing member is mounted to head of the patient and is movable away from and toward a midline plane of head of the patient.

Example 61

The headgear of any of examples 58-60, wherein the band also has an electronic recharge control unit mounted therein, the control unit being coupled to the recharging coil.

Example 62

Headgear for recharging an implantable medical electrical system, the system comprising a power module, a control module, a recharge module, and a housing that contains all the modules, the housing being configured for implantation beneath a scalp of the patient, and the headgear comprising: a securing member for mounting to head of the patient on an exterior side of the scalp, the securing member comprising a resilient band configured to extend, from a first end thereof to a second end thereof, over head of the patient in an arc along a generally vertical plane, and to generally conform to the exterior side of the scalp, when mounted to the head; and at least one conformable member being attached to one or both of the first and second ends of the securing member band for conforming to at least one of a left anterior quadrant, a left posterior quadrant, a right posterior quadrant, and a right anterior quadrant of the scalp, when the securing member is mounted to head of the patient, each of the at least one conformable member having a recharging coil mounted therein.

Example 63

The headgear of example 62, wherein: the securing member further comprises an ear hook; the first end of the securing member band is attached to the ear hook so that the band is moveable relative to the ear hook; and the at least one conformable member comprises a single conformable member attached to the second end of the securing member band.

Example 64

The headgear of either example 62 of 63, wherein: the resilient band of the securing member has another recharging coil mounted therein; the at least one conformable member comprises a pair of resilient bands, each of the pair being movable relative to the securing member band; a first band of the pair extends from a first end thereof to a second end thereof in an arc, the first end of the first band being attached to the second end of the securing member band so that the first band is moveable relative to the securing member band, and the arc of the first band spanning any one of the quadrants of scalp of the patient, when the securing member is mounted to head of the patient; and a second band of the pair extends from a first end thereof to a second end thereof in an arc, the first end of the second band being attached to the second end of the securing member band and to the first end of the first band so that the second band is movable relative to the securing member band and to the first band, and the arc of the second band spanning any one of the quadrants of scalp of the patient, when the securing member is mounted to head of the patient.

Example 65

The headgear of any of examples 62-64, wherein the at least one conformable member comprises a single resilient band extending, from a first end thereof to a second end thereof, in an arc, the first end of the single resilient band being attached to the first end of the securing member band, the second end of the single resilient band being attached to the second end of the securing member band, the single resilient band being moveable relative to the securing member band, and the arc of the single resilient band spanning the left and right quadrants of the scalp, when the securing member is mounted to head of the patient.

Example 66

The headgear of any of examples 62-65, wherein: the at least one conformable member comprises a pair of resilient bands, each of the pair being movable relative to the securing member band; a first band of the pair extends from a first end thereof to a second end thereof in an arc, the first end of the first band being attached to the first end of the securing member band, and the arc of the first band spanning a left posterior quadrant of scalp of the patient, when the securing member is mounted to head of the patient; and a second band of the pair extends from a first end thereof to a second end thereof in an arc, the first end of the second band being attached to the second end of the securing member band, and the arc of the second band spanning a right posterior quadrant of scalp of the patient, when the securing member is mounted to head of the patient.

Example 67

The headgear of any of examples 62-66, wherein the at least one conformable member comprises a pair of cushioned pads, a first of the pair of pads being attached to the first end of the securing member band and conforming to one or both of the left quadrants of the scalp, when the securing member is mounted to head of the patient, a second of the pair of pads being attached to the second end of the securing member band and conforming to one or both of the right quadrants of the scalp, when the securing member is mounted to head of the patient.

Example 68

The headgear of any of examples 62-67, wherein each of the at least one conformable member also has an electronic recharge control unit mounted therein, each control unit being coupled to the corresponding recharging coil.

Example 69

Headgear for recharging an implantable medical electrical system, the system comprising a power module, a control module, a recharge module, and a housing that contains all the modules, the housing being configured for implantation beneath a scalp of the patient in a hollowed out area of the patient's skull, and the headgear comprising: a covering sized to cover, on an exterior side of the scalp, all of a left anterior quadrant, a left posterior quadrant, a right posterior quadrant, and a right anterior quadrant of the scalp, the covering including an inner layer and an outer layer; a plurality of recharging coils mounted between the inner and outer layers of the covering and distributed throughout; and an electronic recharge control unit coupled to each of the plurality of recharging coils.

Example 70

The headgear of example 69, further comprising a collar member attached to a posterior inferior edge of the covering, the collar member containing the electronic recharge control unit.

Example 71

A recharge assembly for an implantable medical electrical system, the system comprising a power module, a control module, a recharge module, and a housing that contains all the modules, the housing being configured for implantation beneath a scalp of the patient in a hollowed out area of the patient's skull, and the recharge assembly comprising: a securing member for mounting to head of the patient on an exterior side of the scalp, the securing member being conformable to a left anterior quadrant, a left posterior quadrant, a right posterior quadrant, and a right anterior quadrant of the scalp, when the securing member is mounted to the head, the securing member having attachment means distributed throughout; and a charge module comprising a recharging coil, an electronic recharge control unit coupled to the coil, and a housing containing the coil and the control unit, the housing including an attachment means configured to mate with the attachment means of the securing member at a selected location along any one of the quadrants of the scalp, when the securing member is mounted to the head.

Example 72

The assembly of example 71, wherein the attachment means of the securing member and of the charge module housing comprise magnetic elements.

Example 73

The assembly of example 71, wherein the attachment means of the securing member and the charge module housing comprise Velcro.

Example 74

A medical system, comprising: an implantable medical device; a recharger configured to charge a power source of the implantable medical device, the recharger comprising a charging coil; and headgear comprising: a securing member for mounting to head of the patient, on an exterior side of the scalp, the securing member being configured to extend around the head and along each of a left anterior quadrant, a left posterior quadrant, a right posterior quadrant, and a right anterior quadrant of the scalp, and to generally conform to the exterior side of the scalp, when mounted to the head; and a plurality of holding features attached to the securing member, a first holding feature of the plurality being located along one or both of the left quadrants of the scalp, when the securing member is mounted to the head, and a second holding feature of the plurality being located along one or both of the right quadrants of the scalp when the securing member is mounted to the head, and each holding feature being configured to hold the charging coil.

Example 75

The medical system of example 74, wherein: the securing member comprises a flexible cap having an inner layer, an outer layer; and each holding feature of the plurality comprises a pocket formed between the inner layer and outer layer of the cap.

Example 76

The medical system of example 75, wherein one or both of the inner and outer layers of the cap comprise a latticework of flexible strips.

Example 77

The medical system of example 74, wherein the securing member comprises an inner layer and an outer layer; and each holding feature comprises a pocket between the inner layer and the outer layer.

Example 78

The medical system of example 74, wherein: the securing member comprises a cap; and each holding feature comprises a recess formed in an outer surface of the cap.

Example 79

The medical system of example 74, wherein: the securing member comprises a flexible cap divided into a left portion and a right portion, the left portion being conformable to the left anterior and posterior quadrants of the scalp, the right portion being conformable to the right anterior and posterior quadrants of the scalp, the left and right portions each having an inner layer and an outer layer, and the left and right portions each having a superior perimeter edge free to move away from and toward a midline plane of head of the patient, when the securing member is mounted to the head; and each holding feature comprises a pocket formed between the inner layer and the outer layer of the corresponding portion of the cap.

Example 80

The medical system of example 74, wherein each holding feature comprises a flexible rail extending in an arc superior to the securing member, each rail having left and right ends attached to the securing member so that the arc of each rail spans left and right quadrants of the scalp, when the securing member is mounted to the head.

Example 81

The medical system of example 80, wherein each flexible rail is free to move in anterior and posterior directions.

Example 82

The medical system of any of examples 74-81, wherein the plurality of holding features are distributed along all of the quadrants of the scalp when the securing member is mounted to the head.

Example 83

The medical system of example 74, further comprising: a right posterior pad and a left posterior pad, the left and right pads being attached to the securing member and extending inferior thereto, and each pad being flexible and cushioned and including an inner layer and an outer layer; and wherein each holding feature comprises a pocket formed between the inner and outer layer of one of the pads.

Example 84

The medical system of any of examples 74-83, wherein the recharger further comprises a control unit that is separately housed from the charging coil, and wherein the headgear further comprises another holding feature attached to the securing member configured to hold the control unit of the recharger.

Example 85

The medical system of any of examples 74-84, wherein the medical device is configured to deliver deep brain stimulation therapy to a patient.

Example 86

A medical system, comprising: a recharger configured to charge a power source of an implantable medical device, the recharger comprising a charging coil; and headgear comprising: a securing member for mounting to head of the patient, on an exterior side of the scalp, the securing member being configured to extend around the head and to generally conform to the exterior side of the scalp, when mounted to the head; and a plurality of holding features attached to the securing member, a first holding feature of the plurality being located along one or both quadrants of the scalp, when the securing member is mounted to the head, and a second holding feature of the plurality being located along one or both of the right quadrants of the scalp when the securing member is mounted to the head, and each holding feature being configured to hold the charging coil.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry or any other equivalent circuitry. In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the terms "processor" or "processing circuitry" as used herein may refer to one or more of any of the foregoing structures or any other structure suitable for implementation of the techniques described herein. In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:
1. A wearable medical system comprising:
 a flexible body configured to cover at least a portion of each of a left anterior quadrant, a left posterior quadrant, a right posterior quadrant, and a right anterior quadrant of a scalp of a head of a patient, wherein the flexible body comprises a first surface and a second surface;
a securing member connected to the flexible body, the securing member configured to extend fully around a circumference of the head and stabilize the flexible body with respect to the scalp of the patient, wherein the securing member is more rigid than the flexible body; and
an attachment assembly configured to mount to a location of the flexible body, the attachment assembly configured to couple the flexible body to a recharge coil configured to recharge an implantable power source of a cranially-mountable implantable medical device, wherein the attachment assembly comprises:
a bracket defining a recess, wherein the bracket is configured to contact the first surface of the flexible body and couple with the recharge coil; and
a pin configured to extend through a hole in the flexible body and into the recess of the bracket to be securely received by the bracket, the pin including a plate configured to contact the second surface of the flexible body when the pin is received by the recess of the bracket.

2. The wearable medical system of claim 1, further comprising:
an external power source secured to at least one of the flexible body or the securing member;
the recharge coil removably secured to the first surface of the flexible body, the recharge coil configured to transmit energy from the power source to recharge the implantable power source of the cranially-mountable implantable medical device; and
a cable coupling the external power source to the recharge coil.

3. The wearable medical system of claim 1, wherein:
the attachment assembly is a first attachment assembly;
the location is a first location;
the recharge coil is a first recharge coil;
the implantable power source is a first implantable power source; and
the cranially-mountable implantable medical device is a first cranially-mounted implantable medical device, further comprising:
a second attachment assembly configured to mount to a second location of the flexible body, the second attachment assembly configured to couple the flexible body to a second recharge coil configured to recharge a second implantable power source of a second cranially-mountable implantable medical device.

4. The wearable medical system of claim 3, further comprising:
an external power source secured to at least one of the flexible body or the securing member;
the first recharge coil removably secured to the first surface of the flexible body, the first recharge coil configured to transmit energy from the power source to recharge the first implantable power source of the first cranially-mountable implantable medical device;
the second recharge coil removably secured to the first surface of the flexible body, the second recharge coil configured to transmit energy from the power source to recharge the second implantable power source of the second cranially-mountable implantable medical device; and
one or more cables configured to couple the external power source to the first and second recharge coils.

5. The wearable medical system of claim 3, wherein the first recharge coil and the second recharge coil are configured to simultaneously transmit energy from the power source to recharge both the implantable power source of the first cranially-mountable implantable medical device and the second implantable power source of the second cranially-mountable implantable medical device.

6. The wearable medical system of claim 3, wherein:
the first attachment assembly is secured to the first surface of the flexible body at a third location adjacent the first location such that the first recharge coil will be aligned with a first implanted recharge coil of the first cranially-mountable implantable medical system when coupled to the first attachment assembly; and
the second attachment assembly is secured to the first surface of the flexible body at a fourth location adjacent the second location such that the second recharge coils will be aligned with a second implanted recharge coil of the second cranially-mountable implantable medical system when coupled to the second attachment assembly.

7. The wearable medical system of claim 3, wherein:
the flexible body comprises a map identifying a plurality of locations;
both the first location and the second location are in the plurality of locations;
the first recharge coil includes a first identifying that identifies the first location; and
the second recharge coil includes a second identifying that identifies the second location.

8. The wearable medical system of claim 3, wherein the one or more cables are removably couplable to the first and second recharge coils.

9. The wearable medical system of claim 1, further comprising:
a first external power source secured to at least one of the flexible body or the securing member;
the first recharge coil removably secured to a first surface of the flexible body, the first recharge coil configured to transmit energy from the first power source to recharge the first implantable power source of the first cranially-mountable implantable medical device;
a second external power source secured to at least one of the flexible body or the securing member;
the second recharge coil removably secured to a second surface of the flexible body, the second recharge coil configured to transmit energy from the second power source to recharge the second implantable power source of the second cranially-mountable implantable medical device.

10. The wearable medical system of claim 1, wherein a material of the securing member comprises at least one of polyethylene, high-density polyethylene, or nylon.

11. The wearable medical system of claim 1, wherein the flexible body comprises a map identifying a plurality of locations, wherein the location is one of the plurality of locations.

12. The wearable medical system of claim 1, further comprising a bill that is configured to extend radially out from the flexible body, wherein the bill is connected to the flexible body along at least a portion of the left anterior quadrant and the right anterior quadrant.

13. The wearable medical system of claim 1, wherein the flexible body includes at least two seams that are configured to secure a shape of the flexible body when covering at least a portion of the scalp by extending substantially straight across the flexible body between the securing member, wherein a first seam of the least two seams extends from the left anterior quadrant to the right posterior quadrant and a second seam of the least two seams extends from the right anterior quadrant to the left posterior quadrant.

14. The wearable medical system of claim 1, wherein the securing member comprises an adjustable mechanism configured to adjust a circumference of the securing member.

15. The wearable medical system of claim 14, wherein the securing member comprises a click wheel configured to increase the circumference of the securing member when the click wheel is turned in a first direction and configured to decrease the circumference when the click wheel is turned in a second direction opposite the first direction.

16. The wearable medical system of claim 15, wherein the securing member includes a band with overlapping ends, wherein an adjustable amount of overlap between the overlapping ends defines the circumference of the securing member.

17. The wearable medical system of claim 1, wherein the power source comprises a power source attachment mechanism configured to attach the power source to the securing member adjacent the left posterior quadrant and the right posterior quadrant.

18. The wearable medical system of claim 1, further comprising a curved housing configured to house an external power source, wherein the curved housing defines a first main surface configured to interface with the scalp and a second main surface that is on an opposite side of the curved housing of the first main surface, where the first main surface and the second main surface define substantially similar curvatures that approximate a curvature of a back of the head of the patient.

19. The wearable medical system of claim 1, further comprising a curved container that is configured to house the recharge coil, wherein the curved container defines a concave main surface that approximates a curvature of the scalp of the patient and is configured to interface with the scalp of the patient.

20. The wearable medical system of claim 19, wherein the main surface is a first main surface, wherein the curved container defines a second main surface that is on an opposite side of the curved container of the first main surface and approximates the curvature of the scalp of the patient, wherein the second main surface defines a ridge that extends out away from the second main surface, wherein the flexible body includes a first surface configured to contact the scalp and a second surface that is on an opposite side of the flexible body relative to the first surface, wherein the attachment assembly is configured to secure the curved housing for the recharge coil to the flexible body,
wherein the bracket defines a channel configured to receive the ridge of the second main surface to securely attach the bracket to the curved container, and
wherein the pin is configured to extend through the hole in the flexible body from the second surface of the flexible body past the first surface of the flexible body into the recess of the bracket to be securely received by the bracket.

21. The wearable medical system of claim 20, wherein the curved container includes a bore that extends through the curved container and is centered within the ridge, wherein the bore is configured to receive the recess of the bracket when the bracket is securely attached to the curved container, where the bore is configured to accept a marking pen to enable positioning of the curved housing over the cranially-mountable implantable medical device to visibly mark the location on the first main surface flexible body.

22. The wearable medical system of claim 20 further comprising a piercing element configured to be removably coupled to the pin, the piercing element including a piercing tip configured to pierce the flexible body from the first surface through to the second surface to create the hole in the flexible body.

23. A wearable medical system, comprising:
a flexible body configured to cover at least a portion of each of a left anterior quadrant, a left posterior quadrant, a right posterior quadrant, and a right anterior quadrant of a scalp of a head of a patient, wherein the flexible body comprises a first surface and a second surface;
a securing member connected to the flexible body, the securing member configured to extend fully around a circumference of the head and stabilize the flexible body with respect to the scalp of the patient, wherein the securing member is more rigid than the flexible body;
an external power source secured to at least one of the flexible body or the securing member;
a first recharge coil removably configured to transmit energy from the power source to recharge a first implantable power source of a first cranially-mountable implantable medical device;
a second recharge coil removably configured to transmit energy from the power source to recharge a second implantable power source of a second cranially-mountable implantable medical device;
one or more cables coupling the external power source to the first and second recharge coils;
a first attachment assembly configured to mount to a first location of the flexible body, the first attachment assembly configured to securely attach the first recharge coil to the flexible body; and
a second attachment assembly configured to mount to a second location of the flexible body, the second attachment assembly configured to securely attach the second recharge coil to the flexible body, wherein each of the first attachment assembly and the second attachment assembly comprises:
a bracket defining a recess, wherein the bracket is configured to contact the inner surface of the flexible body and couple with the recharge coil; and
a pin configured to extend through a hole in the flexible body and into the recess of the bracket to be securely received by the bracket, the pin including a plate configured to contact the second surface of the flexible body when the pin is received by the recess of the bracket.

24. The wearable medical system of claim 23, wherein the securing member comprises a band that is relatively more rigid than the flexible body.

25. The wearable medical system of claim 23, wherein the flexible body comprises a map identifying a plurality of locations, wherein the location is one of the plurality of locations.

26. The wearable medical system of claim 23, further comprising a bill that is configured to extend radially out from the flexible body, wherein the bill is connected to the flexible body along at least a portion of the left anterior quadrant and the right anterior quadrant.

27. The wearable medical system of claim 23, wherein the flexible body includes at least two seams that are configured to secure a shape of the flexible body when covering at least a portion of the scalp by extending substantially straight across the flexible body between the securing member, wherein a first seam of the least two seams extends from the left anterior quadrant to the right posterior quadrant and a second seam of the least two seams extends from the right anterior quadrant to the left posterior quadrant.

28. The wearable medical system of claim 23, wherein the securing member comprises an adjustable mechanism configured to adjust a circumference of the securing member.

29. The wearable medical system of claim 23, further comprising a curved housing configured to house the external power source, wherein the curved housing defines a first main surface configured to interface with the scalp and a second main surface that is on an opposite side of the curved housing of the first main surface, where the first main surface and the second main surface define substantially similar curvatures that approximate a curvature of the scalp of the patient.

30. The wearable medical system of claim 23, further comprising a first and second curved container that are configured to house the first and second recharge coils, wherein each of the first and second curved containers defined a concave first main surface that approximates a curvature of the scalp and a second main surface that approximates a curvature of the scalp, the first main surface configured to interface with the scalp of the patient and the second main surface on an opposite side of the respective curved container of the first main surface, wherein the second main surface defines a ridge that extends out away from the second main surface, wherein the flexible body includes a first surface configured to contact the scalp and a second surface that is on an opposite side of the flexible body relative to the first surface, wherein both the first attachment assembly and the second attachment assembly are configured to secure the first and second curved housing for the first and second recharge coil to the flexible body, and wherein, for each of the first attachment assembly and the second attachment assembly:
   the bracket defines a channel configured to receive the ridge of the second main surface to securely attach the bracket to the curved container, and
   wherein the pin is configured to extend through the hole in the flexible body from the second surface of the flexible body past the first surface of the flexible body into the recess of the bracket to be securely received by the bracket.

31. A wearable medical system, comprising:
   a flexible body configured to cover at least a portion of each of a left anterior quadrant, a left posterior quadrant, a right posterior quadrant, and a right anterior quadrant of a scalp of a head of a patient, wherein the flexible body comprises an inner surface and an outer surface;
   a curved container that is configured to house a recharge coil and defines a concave first main surface and a convex second main surface that each approximate a curvature of a scalp of a head of a patient, the first main surface configured to interface with the scalp of the patient and the second main surface is on an opposite side of the curved container of the first main surface, wherein the second main surface defines a ridge that extends out away from the second main surface and a bore that extends through the curved container;
   a bracket defining a cylindrical recess configured to be received by the bore and a channel that is configured to receive the ridge of the second main surface to securely attach the bracket to the curved container, wherein the bracket is configured to contact the inner surface of the flexible body; and
   a pin configured to extend into the cylindrical recess of the bracket to be securely received by the bracket, the pin including a plate configured to contact the outer surface of the flexible body when the pin is received by the recess of the bracket.

32. The wearable medical device of claim 31, further comprising a recharge coil housed within the curved container that is configured to transmit energy to recharge an implantable power source of a cranially-mountable implantable medical device.

33. The wearable medical device of claim 32, further comprising:
   a curved housing configured to house an external power source, wherein the curved housing defines a first main surface configured to interface with the scalp and a second main surface that is on an opposite side of the curved housing of the first main surface, where the first main surface and the second main surface define substantially similar curvatures that approximate a curvature of the scalp of the patient; and
   a cable coupling the external power source to the recharge coil.

34. The wearable medical device of claim 33, further comprising processing circuitry configured to cause the recharge coil to transmit energy from the external power source to recharge the implantable power source of the cranially-mountable implantable medical device.

35. The wearable medical device of claim 31, wherein the curved container is a first curved container and the bracket is a first bracket and the pin is a first pin, further comprising:
   a second curved container that is substantially similar to the first curved container;
   a second bracket that is substantially similar to the first bracket;
   a second pin that is substantially similar to the first pin;
   a first recharge coil housed within the first curved container that is configured to transmit energy to recharge a first implantable power source of a first cranially-mountable implantable medical device;
   a second recharge coil housed within the second curved container that is configured to transmit energy to recharge a second implantable power source of a second cranially-mountable implantable medical device;
   a curved housing configured to house an external power source, wherein the curved housing defines a first main surface configured to interface with the scalp and a second main surface that is on an opposite side of the curved housing of the first main surface, where the first main surface and the second main surface define substantially similar curvatures that approximate a curvature of the scalp of the patient; and
   one or more cables coupling the external power source to the first and second recharge coils.

36. The wearable medical device of claim 35, further comprising processing circuitry configured to cause the first and second recharge coils to transmit energy from the external power source to recharge the first and second implantable power sources of the first and second cranially-mountable implantable medical devices.

* * * * *